(12) United States Patent
Alexander et al.

(10) Patent No.: US 10,045,842 B2
(45) Date of Patent: Aug. 14, 2018

(54) SYSTEMS, IMPLANTS, TOOLS, AND METHODS FOR TREATMENTS OF PELVIC CONDITIONS

(75) Inventors: James A. Alexander, Excelsior, MN (US); Kevin R. Arnal, Excelsior, MN (US); Jeffrey J. Childs, Eagan, MN (US); Chaouki A. Khamis, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 601 days.

(21) Appl. No.: 13/519,492

(22) PCT Filed: Dec. 30, 2010

(86) PCT No.: PCT/US2010/062577
§ 371 (c)(1),
(2), (4) Date: Jan. 3, 2013

(87) PCT Pub. No.: WO2011/082350
PCT Pub. Date: Jul. 7, 2011

(65) Prior Publication Data
US 2013/0109910 A1 May 2, 2013

Related U.S. Application Data

(60) Provisional application No. 61/291,188, filed on Dec. 30, 2009, provisional application No. 61/291,366, (Continued)

(51) Int. Cl.
*A61F 2/00* (2006.01)
*A61B 17/00* (2006.01)
(Continued)

(52) U.S. Cl.
CPC .......... *A61F 2/0063* (2013.01); *A61B 1/0051* (2013.01); *A61B 1/00082* (2013.01);
(Continued)

(58) Field of Classification Search
CPC ........................................... A61F 2/00–2/0095
(Continued)

(56) References Cited

U.S. PATENT DOCUMENTS 5,197,971 A 3/1993 Bonutti
5,254,106 A 10/1993 Feaster
(Continued)

FOREIGN PATENT DOCUMENTS

CN 101420909 4/2009
EP 0537573 4/1993
(Continued)

OTHER PUBLICATIONS

Canadian Office Action for Canadian Application No. 2,786,064, dated Aug. 10, 2017, 8 pages.
(Continued)

*Primary Examiner* — Catherine B Kuhlman
(74) *Attorney, Agent, or Firm* — Brake Hughes Bellermann LLP

(57) ABSTRACT

Described are various embodiments of surgical procedure systems, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue, devices and tools for transvaginally accessing a posterior region of pelvic anatomy, devices (including certain types of implants, anchors, and tools) for connecting
(Continued)

(e.g., adjustably) a vaginal apex to a region of sacral anatomy to provide support to the vaginal apex, and related methods.

13 Claims, 102 Drawing Sheets

Related U.S. Application Data filed on Dec. 31, 2009, provisional application No. 61/291,370, filed on Dec. 31, 2009, provisional application No. 61/291,373, filed on Dec. 31, 2009, provisional application No. 61/291,387, filed on Dec. 31, 2009, provisional application No. 61/291,462, filed on Dec. 31, 2009, provisional application No. 61/297,579, filed on Jan. 22, 2010.

(51) Int. Cl.
| | |
|---|---|
| *A61B 17/02* | (2006.01) |
| *A61B 17/04* | (2006.01) |
| *A61B 17/06* | (2006.01) |
| *A61B 17/068* | (2006.01) |
| *A61B 17/08* | (2006.01) |
| *A61B 17/10* | (2006.01) |
| *A61B 17/42* | (2006.01) |
| *A61B 1/00* | (2006.01) |
| *A61B 1/005* | (2006.01) |
| *A61B 1/06* | (2006.01) |
| *A61B 1/12* | (2006.01) |
| *A61B 1/32* | (2006.01) |
| *A61B 90/30* | (2016.01) |
| A61B 17/064 | (2006.01) |
| A61B 17/3203 | (2006.01) |
| A61B 17/3207 | (2006.01) |
| A61B 17/34 | (2006.01) |
| A61B 17/22 | (2006.01) |
| A61B 17/32 | (2006.01) |
| A61B 90/00 | (2016.01) |

(52) U.S. Cl.
CPC ...... *A61B 1/00087* (2013.01); *A61B 1/00094* (2013.01); *A61B 1/06* (2013.01); *A61B 1/12* (2013.01); *A61B 1/32* (2013.01); *A61B 17/00234* (2013.01); *A61B 17/0206* (2013.01); *A61B 17/0293* (2013.01); *A61B 17/0401* (2013.01); *A61B 17/0469* (2013.01); *A61B 17/068* (2013.01); *A61B 17/06109* (2013.01); *A61B 17/08* (2013.01); *A61B 17/10* (2013.01); *A61B 17/42* (2013.01); *A61B 90/30* (2016.02); *A61F 2/0045* (2013.01); *A61B 17/0643* (2013.01); *A61B 17/3203* (2013.01); *A61B 17/320725* (2013.01); *A61B 17/3439* (2013.01); *A61B 90/37* (2016.02); *A61B 2017/00278* (2013.01); *A61B 2017/00353* (2013.01); *A61B 2017/00805* (2013.01); *A61B 2017/00907* (2013.01); *A61B 2017/00986* (2013.01); *A61B 2017/0409* (2013.01); *A61B 2017/0417* (2013.01); *A61B 2017/0438* (2013.01); *A61B 2017/0464* (2013.01); *A61B 2017/0496* (2013.01); *A61B 2017/0641* (2013.01); *A61B 2017/0648* (2013.01); *A61B 2017/0649* (2013.01); *A61B 2017/06176* (2013.01); *A61B 2017/22061* (2013.01); *A61B 2017/320044* (2013.01); *A61B 2017/320048* (2013.01); *A61B 2090/306* (2016.02); *A61B 2090/3614* (2016.02)

(58) Field of Classification Search
USPC .................. 600/29–31, 37; 606/139–158
See application file for complete search history.

(56) References Cited

U.S. PATENT DOCUMENTS

| | | | |
|---|---|---|---|
| 2002/0028980 A1* | 3/2002 | Thierfelder et al. | 600/37 |
| 2006/0205995 A1 | 9/2006 | Browning | |
| 2006/0229596 A1* | 10/2006 | Weiser et al. | 606/37 |
| 2006/0276871 A1 | 12/2006 | Lamson et al. | |
| 2008/0125803 A1 | 5/2008 | Sadamasa | |
| 2008/0139878 A1* | 6/2008 | Van Der Weiden | 600/37 |
| 2008/0207988 A1 | 8/2008 | Hanes | |
| 2009/0312783 A1 | 12/2009 | Whayne et al. | |
| 2010/0081865 A1* | 4/2010 | Hamati | A61F 2/0045 |
| | | | 600/37 |
| 2010/0256442 A1 | 10/2010 | Ogdahl et al. | |
| 2010/0261955 A1* | 10/2010 | O'Hern | A61B 17/0401 |
| | | | 600/37 |
| 2011/0288368 A1* | 11/2011 | VanDeWeghe | A61B 17/06109 |
| | | | 600/30 |

FOREIGN PATENT DOCUMENTS

| | | | |
|---|---|---|---|
| JP | 2008526344 A | 7/2008 | |
| KR | 1020090021140 A | 2/2009 | |
| WO | WO 94/20026 | 9/1994 | |
| WO | WO 02/078552 | 10/2002 | |
| WO | 2006/108145 | 10/2006 | |
| WO | 2006/108145 A1 | 10/2006 | |
| WO | 2007/097994 | 8/2007 | |
| WO | WO 2007/149348 | 12/2007 | |
| WO | WO 2007/149555 | 12/2007 | |
| WO | WO 2007149555 A2 * | 12/2007 | ......... A61F 2/0045 |
| WO | WO 2010093421 A2 * | 8/2010 | ....... A61B 17/06109 |

OTHER PUBLICATIONS

Office Action for Korean Application No. 7019957/2012, dated Mar. 16, 2017, 14 pages.

\* cited by examiner

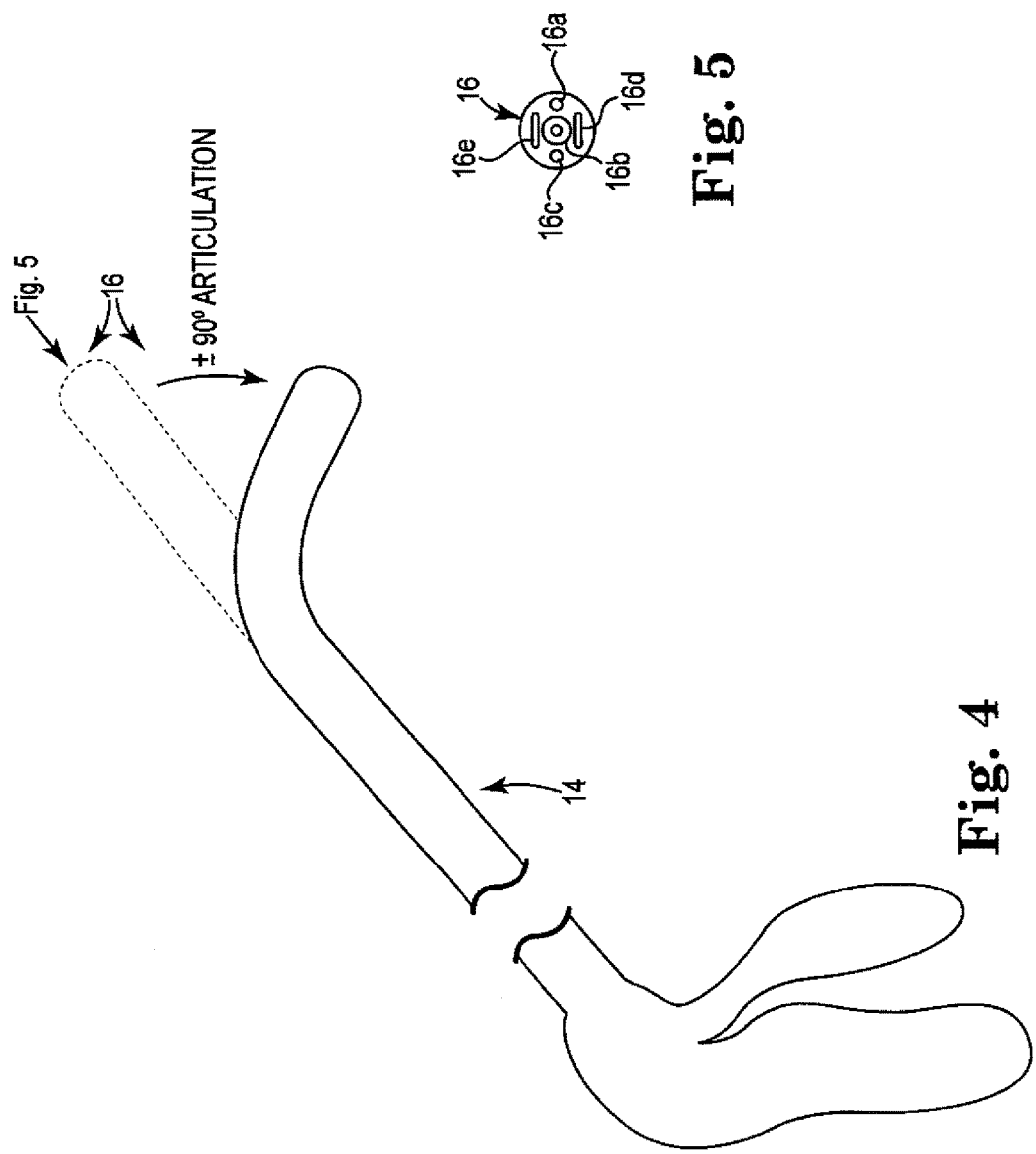

ANCHOR WITH INTEGRATED SUTURE

ANCHOR WITH INTEGRATED SUTURE AND MESH

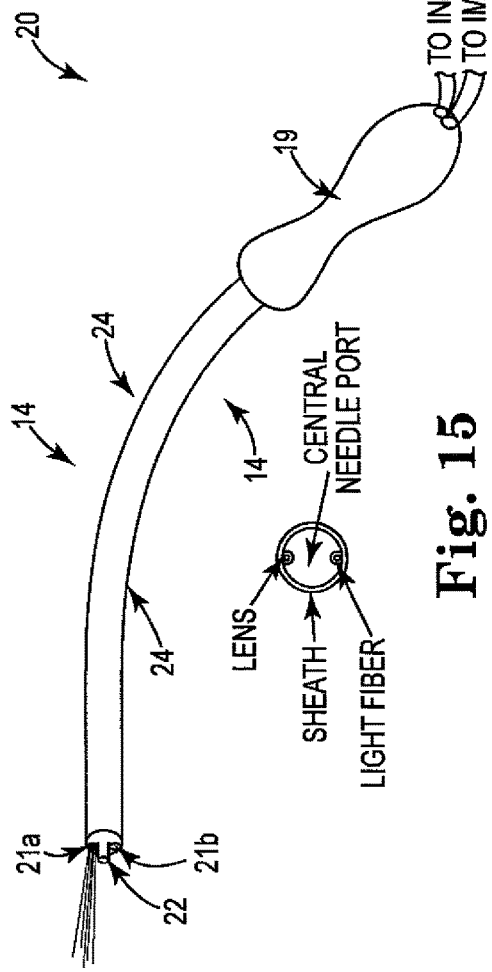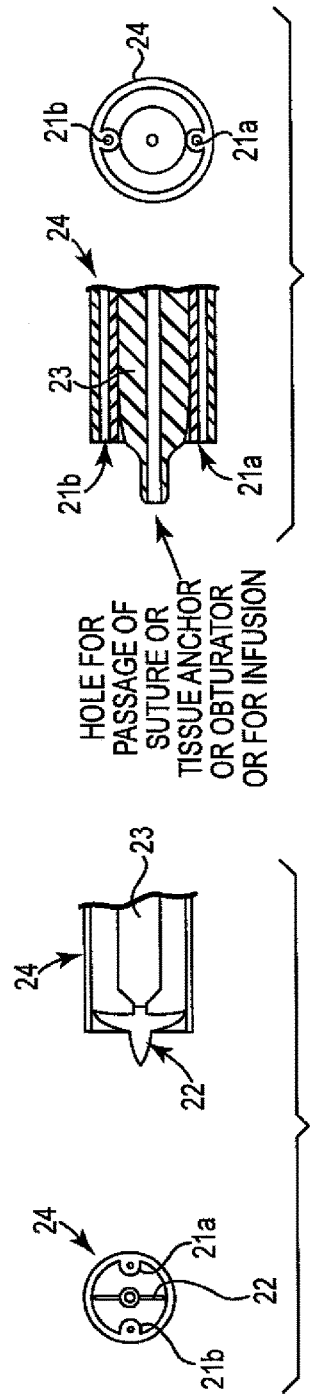

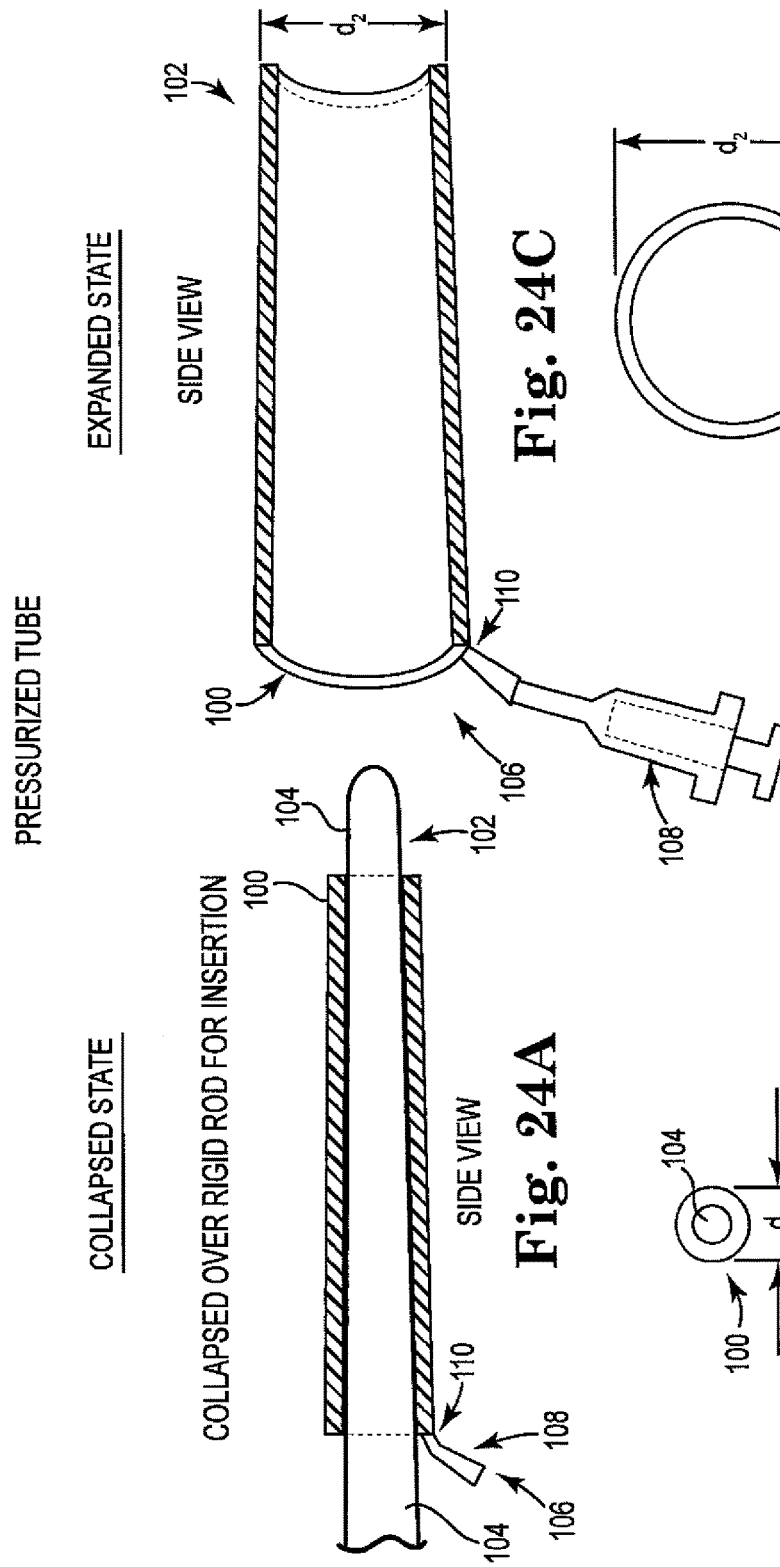

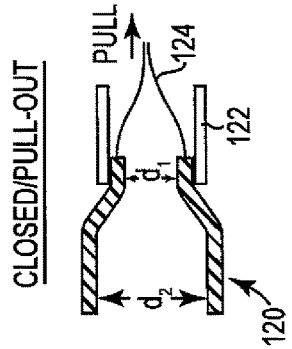
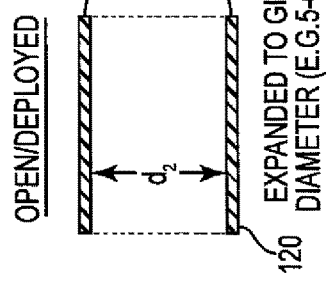
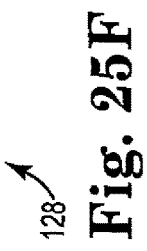
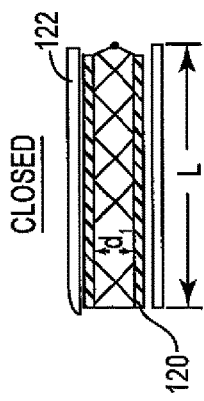
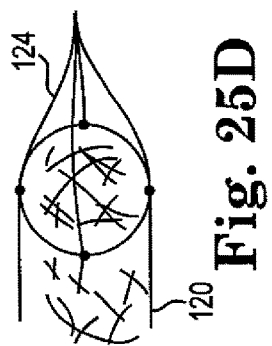
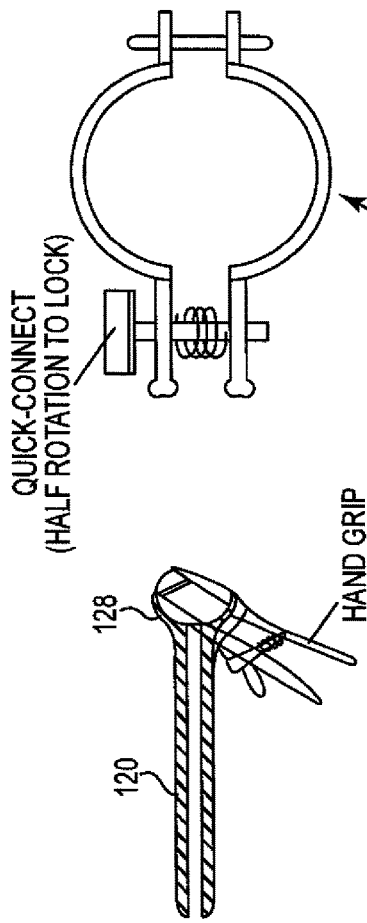

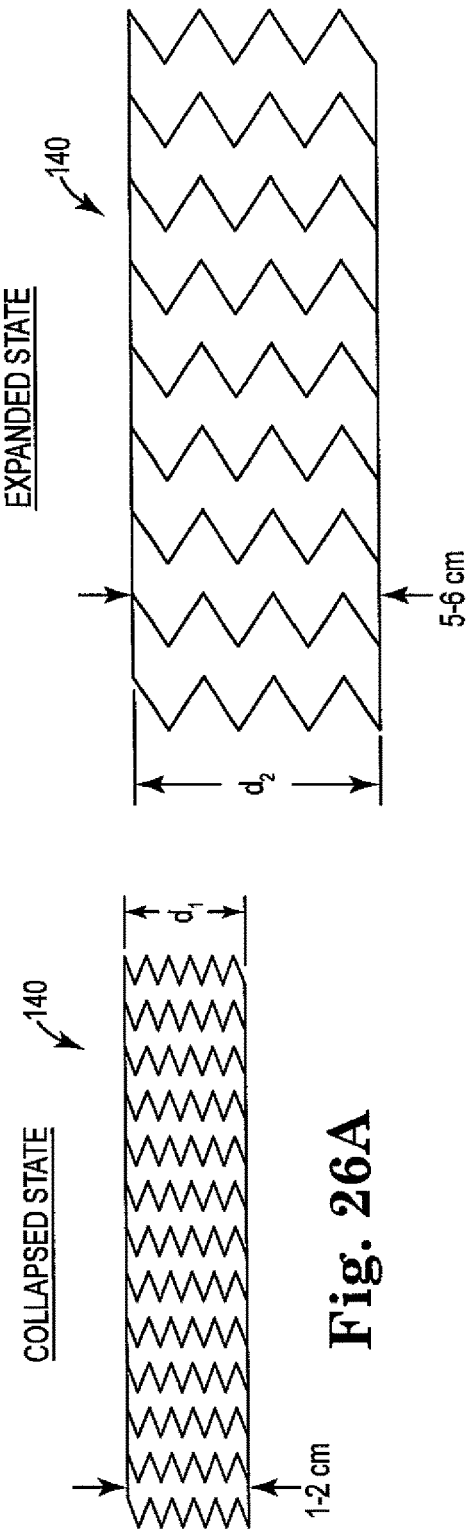

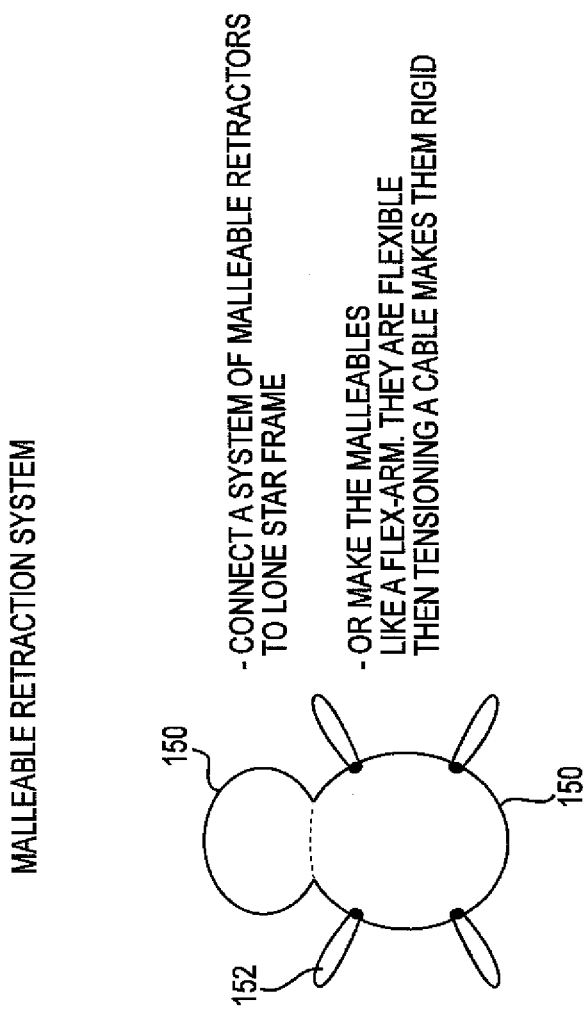

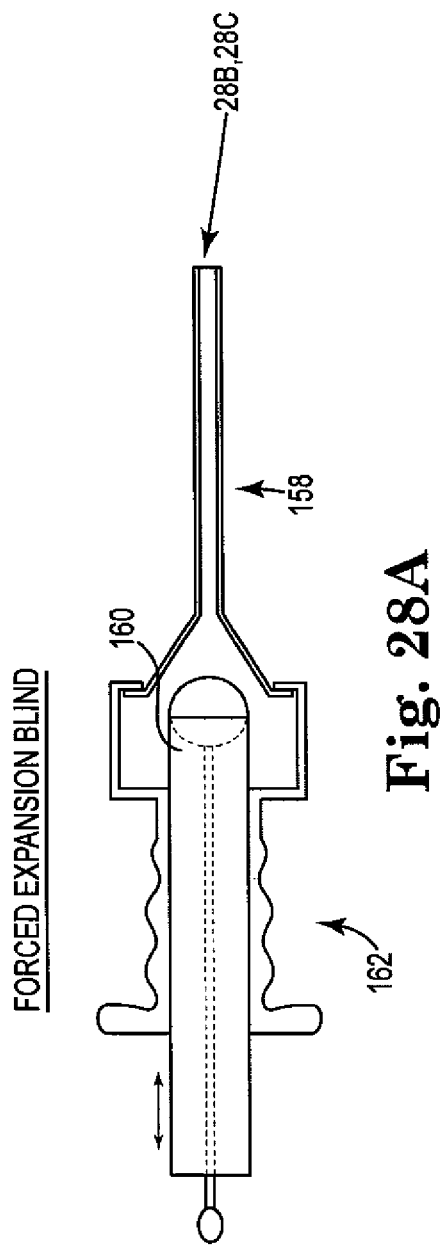
Fig. 28A
Fig. 28B
Fig. 28C

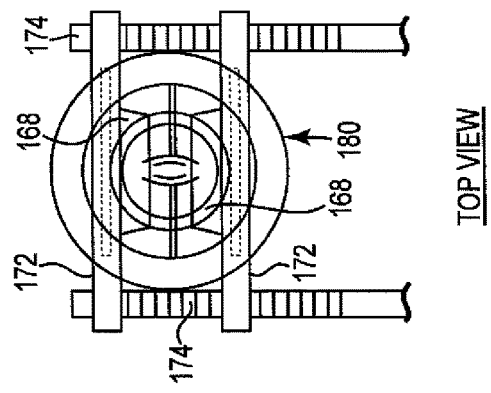
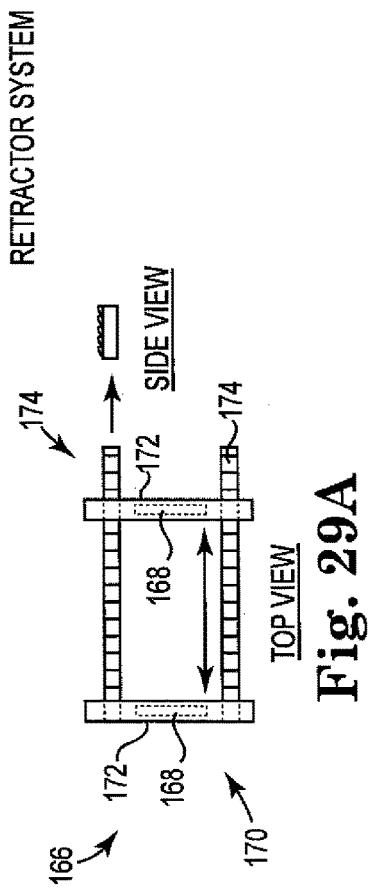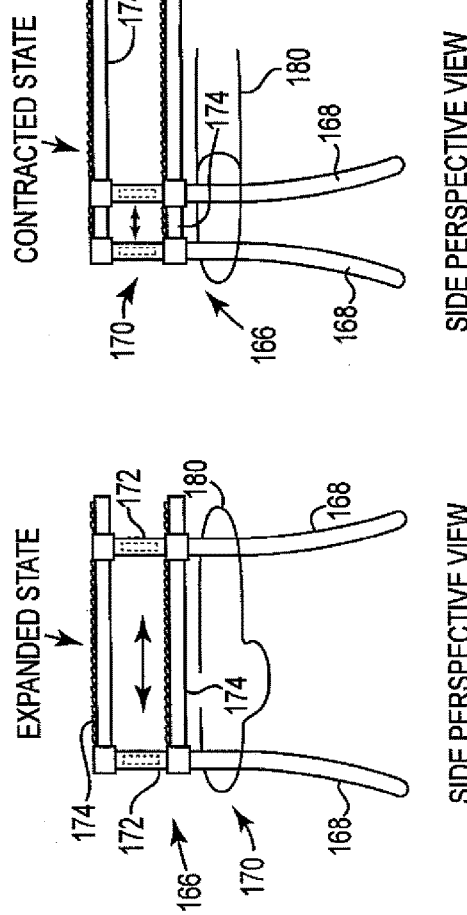
Fig. 29A  Fig. 29B  Fig. 29C  Fig. 29D

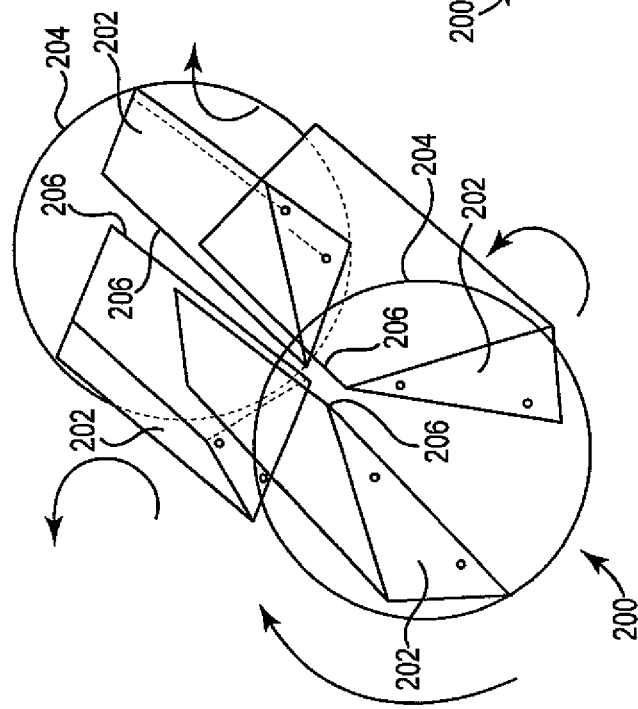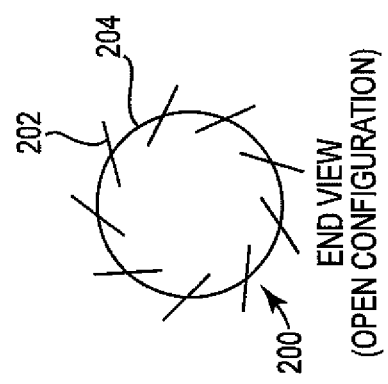
Fig. 31A  Fig. 31B  Fig. 31C

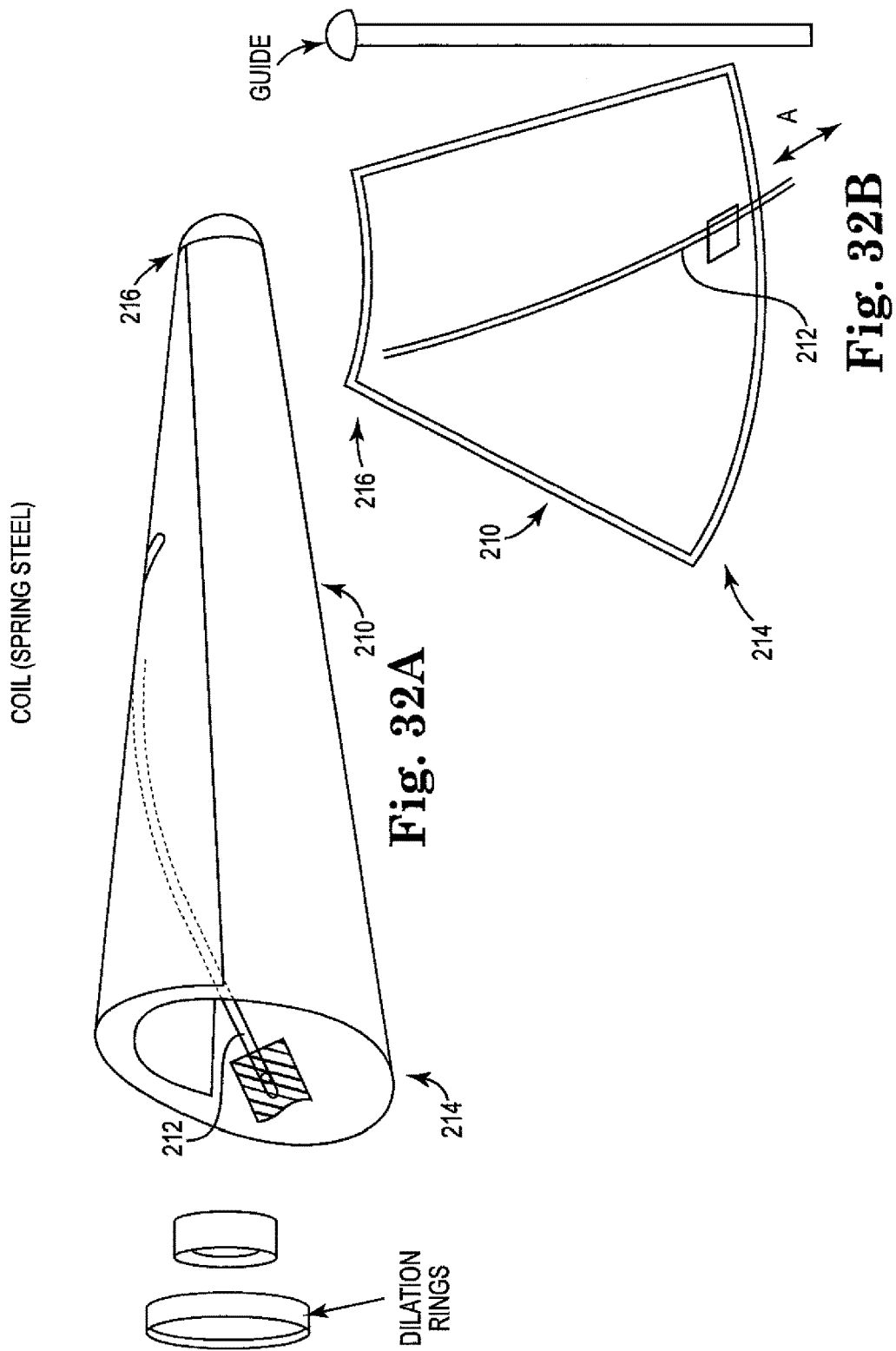

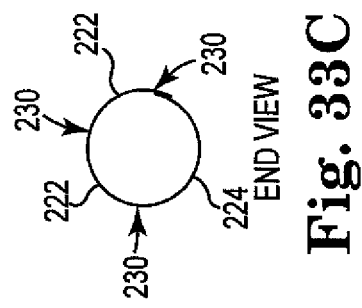
Fig. 33C
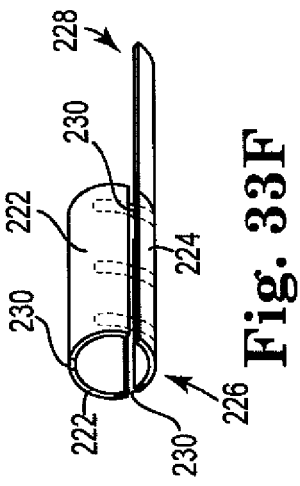
Fig. 33F
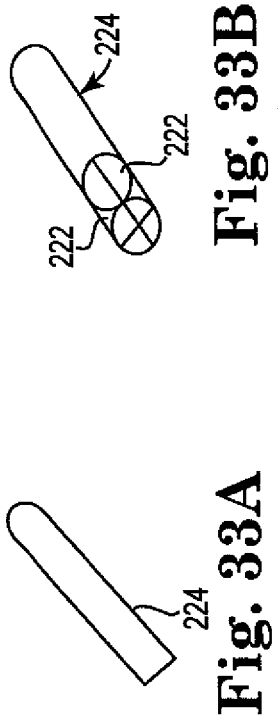
Fig. 33B
Fig. 33E
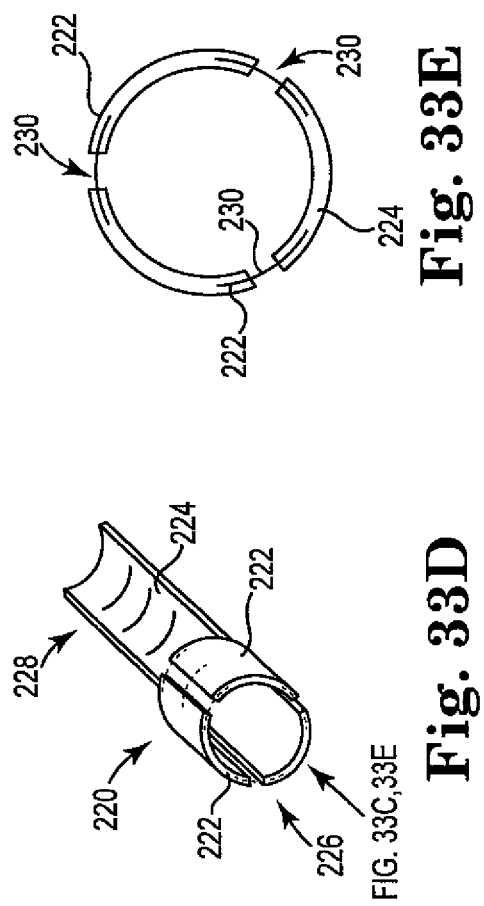
Fig. 33A
Fig. 33D CAN OPENER RETRACTOR, PRESSURE RETRACTOR WITH FUNNEL, RETRACTING BLIND
Fig. 34A
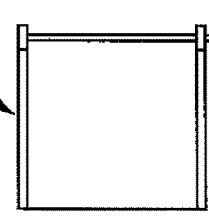
Fig. 34B
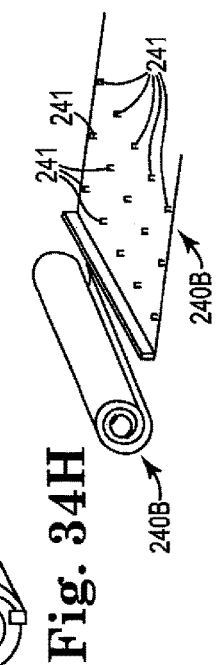
(TOP VIEW)
Fig. 34C
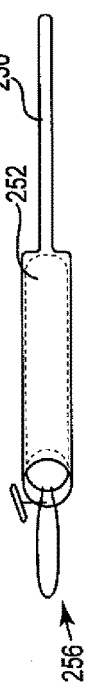
Fig. 34D
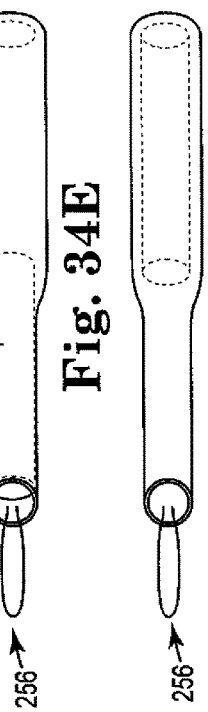
Fig. 34E
Fig. 34F
Fig. 34G
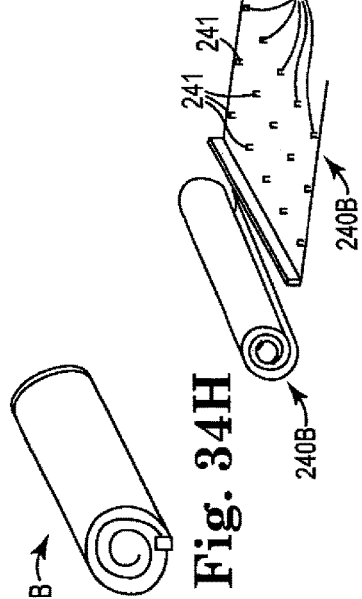
Fig. 34H
Fig. 34I
Fig. 34J

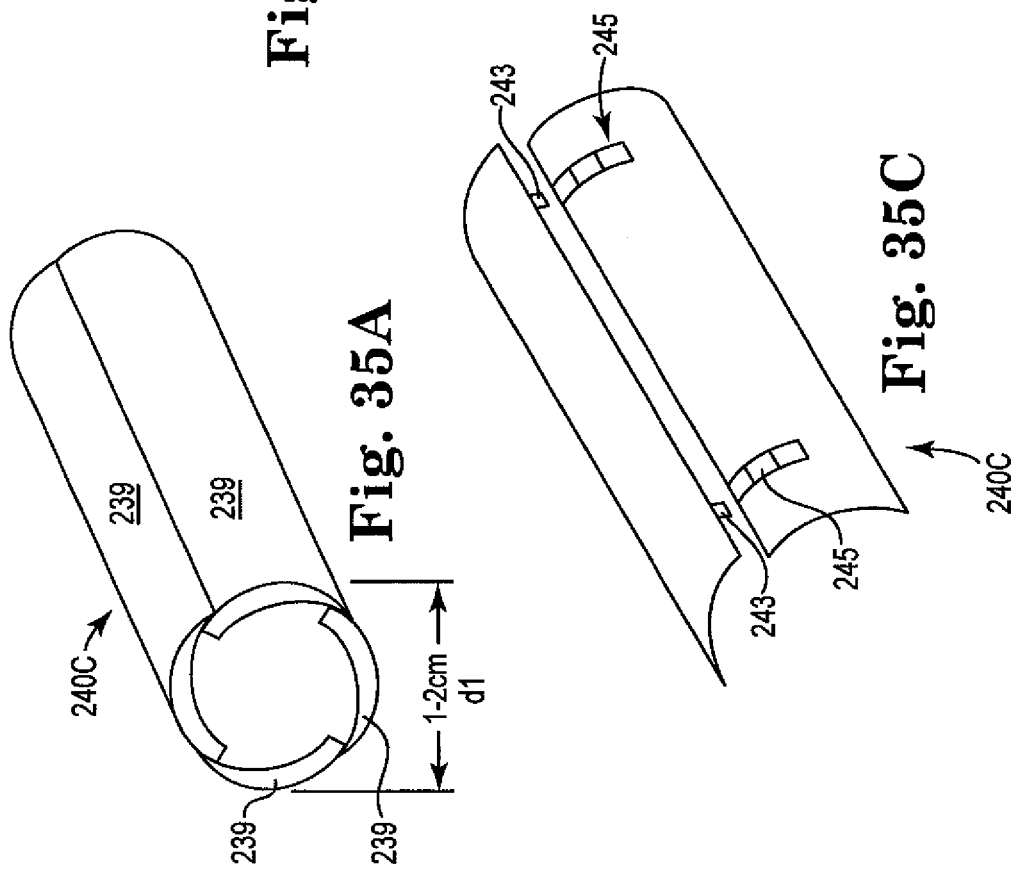

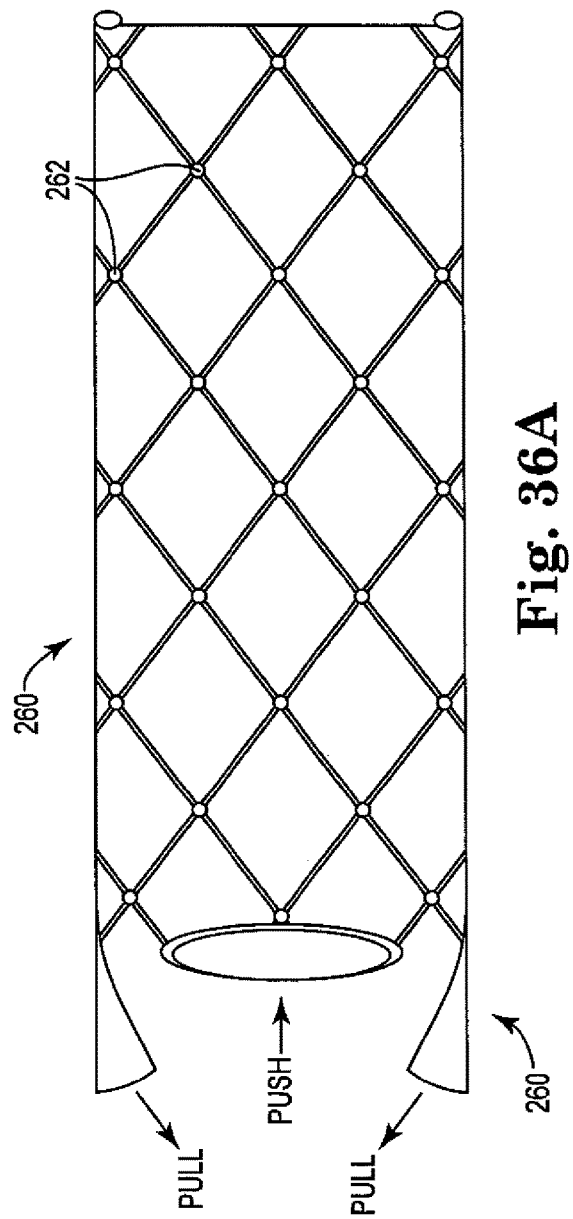
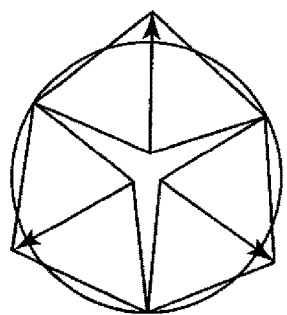
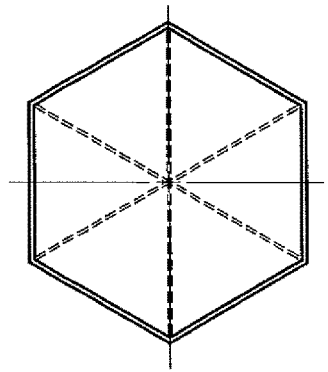
Fig. 36A
Fig. 36B
Fig. 36C

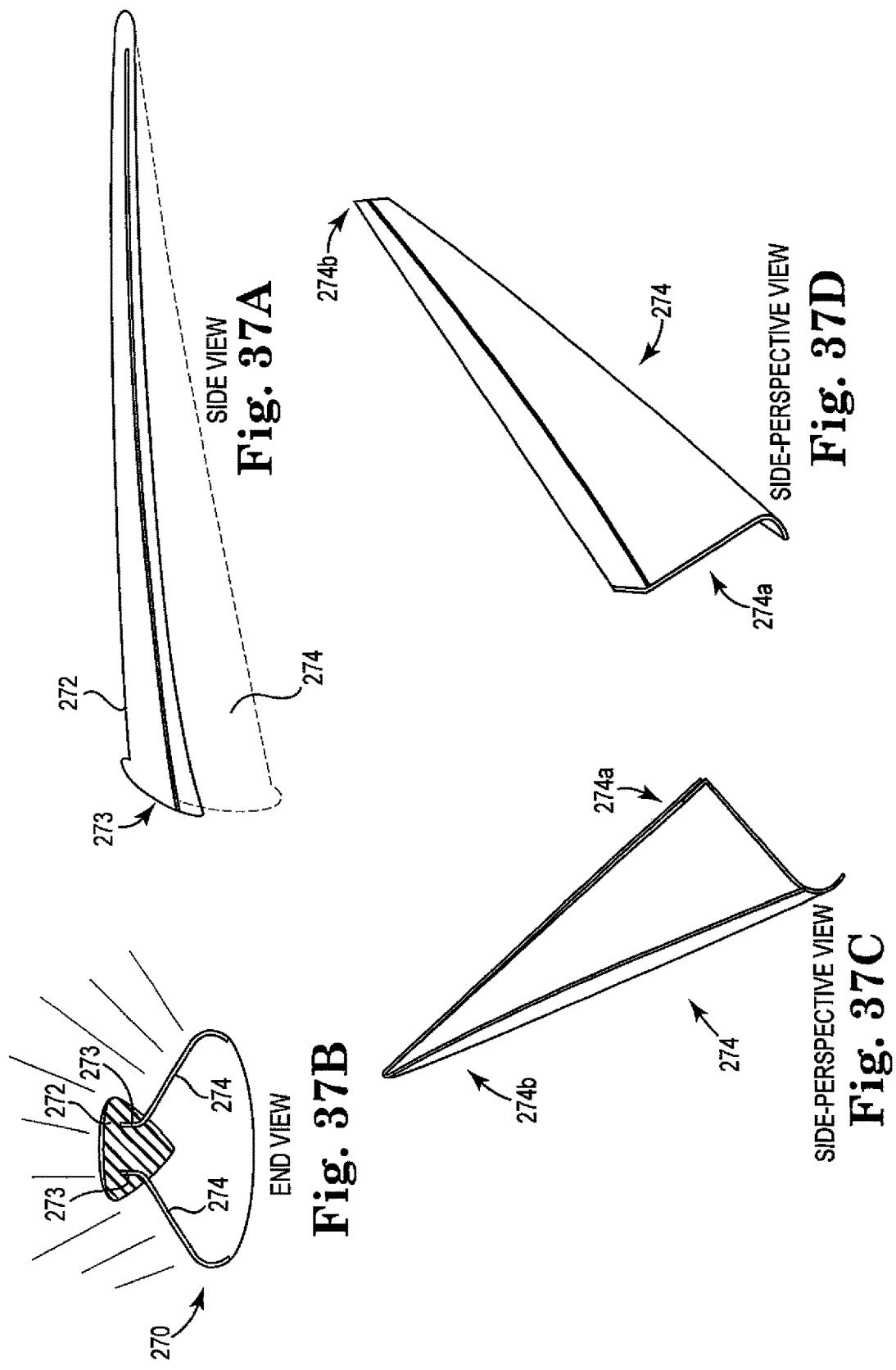

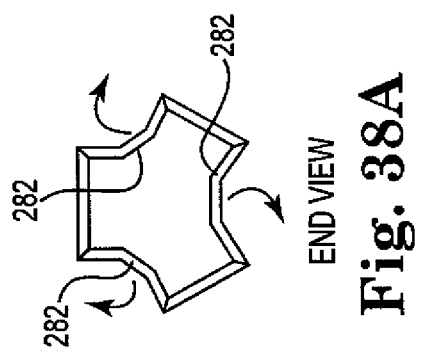
Fig. 38A END VIEW
282
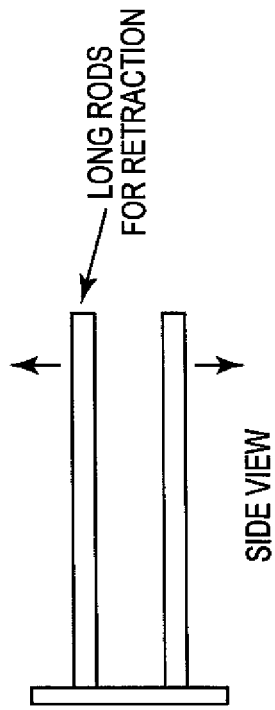
LONG RODS FOR RETRACTION
Fig. 38B SIDE VIEW

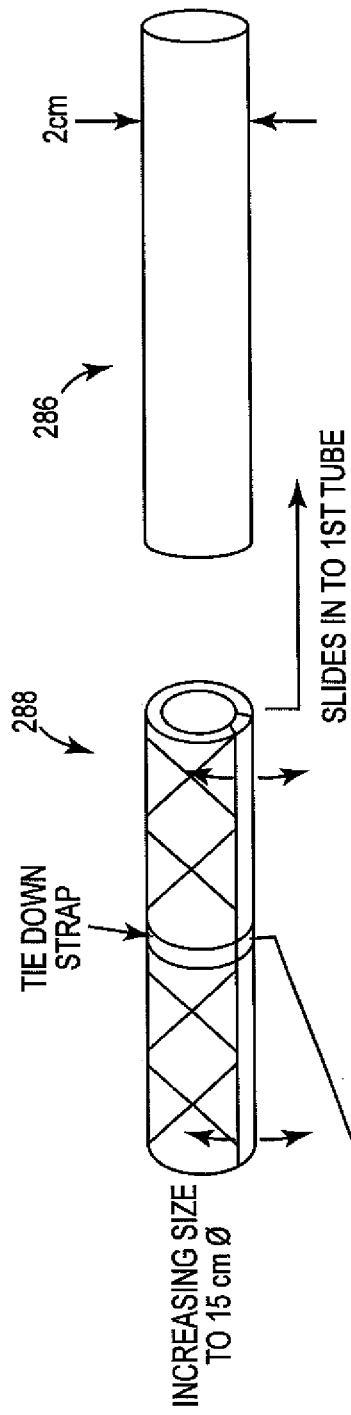

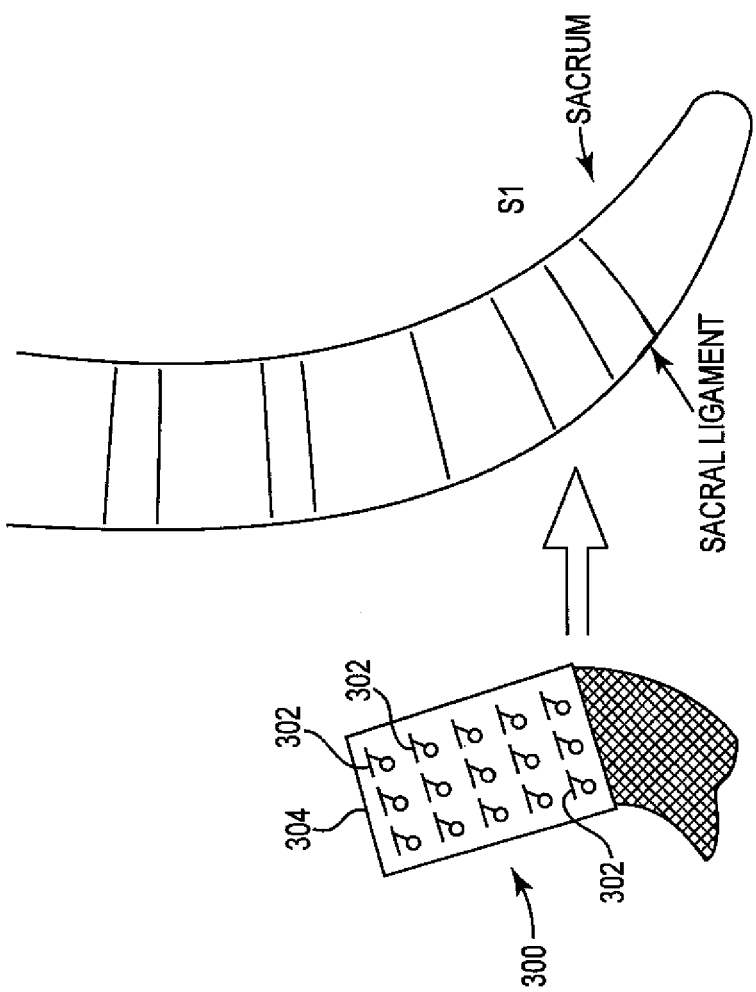

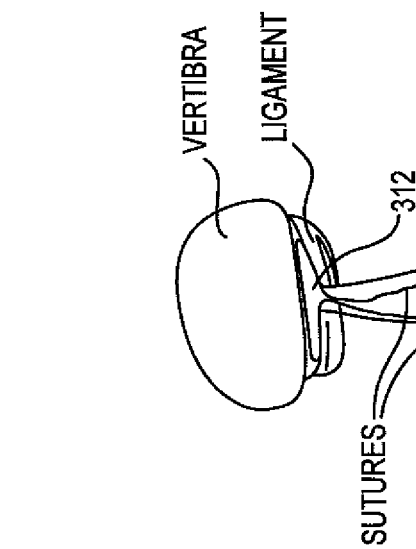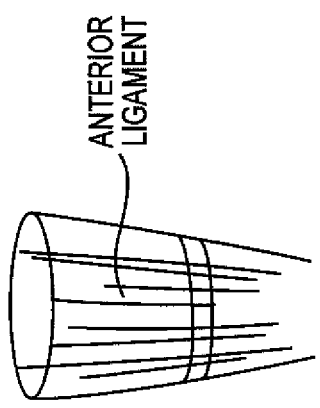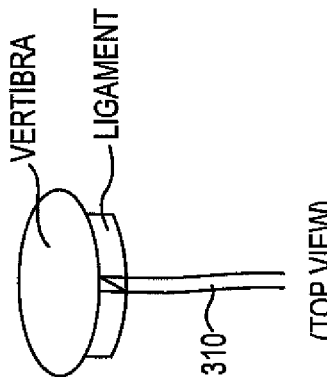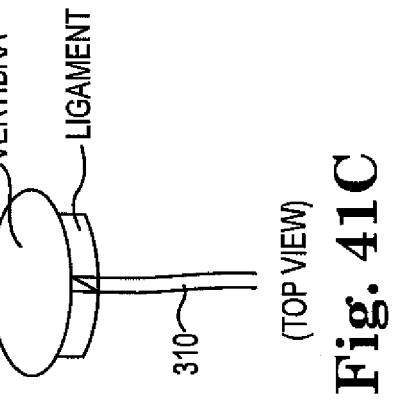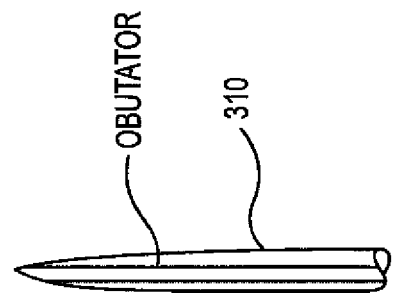
Fig. 41A  Fig. 41B  Fig. 41C  Fig. 41D

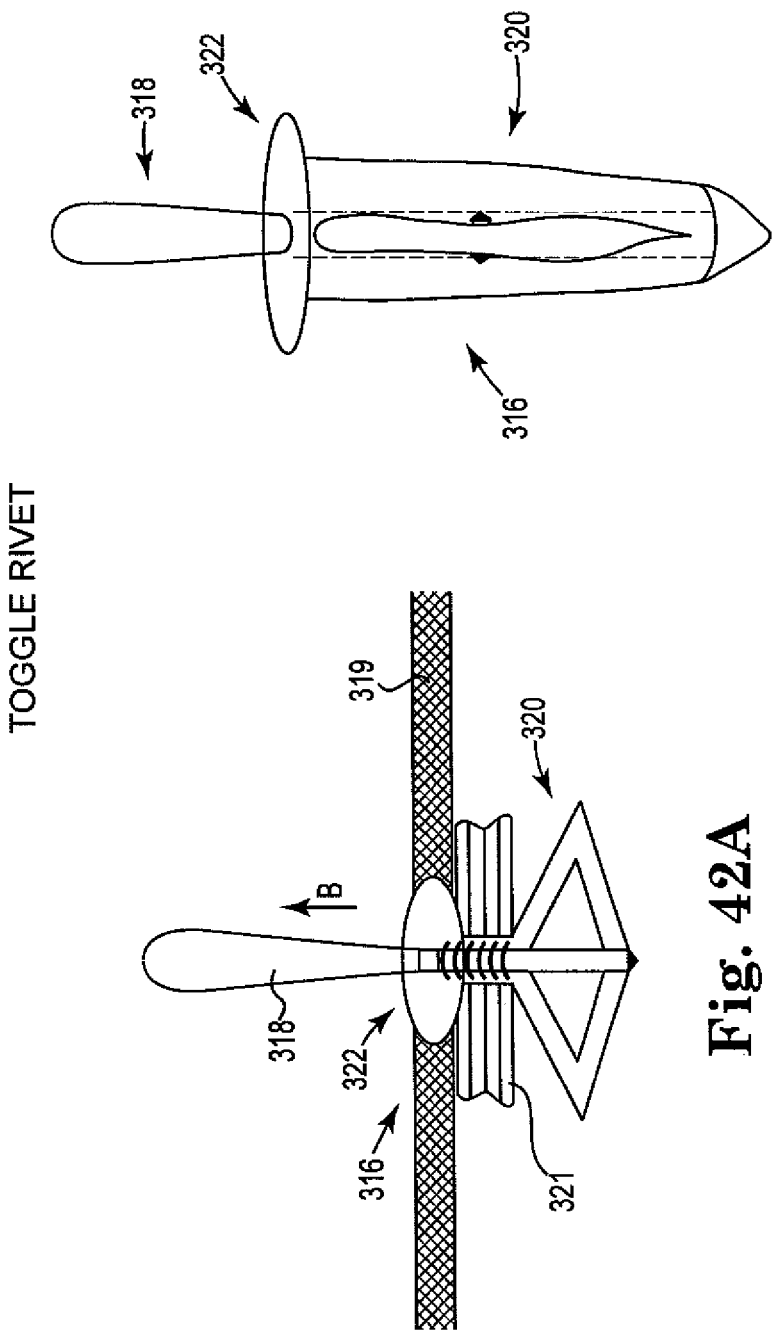

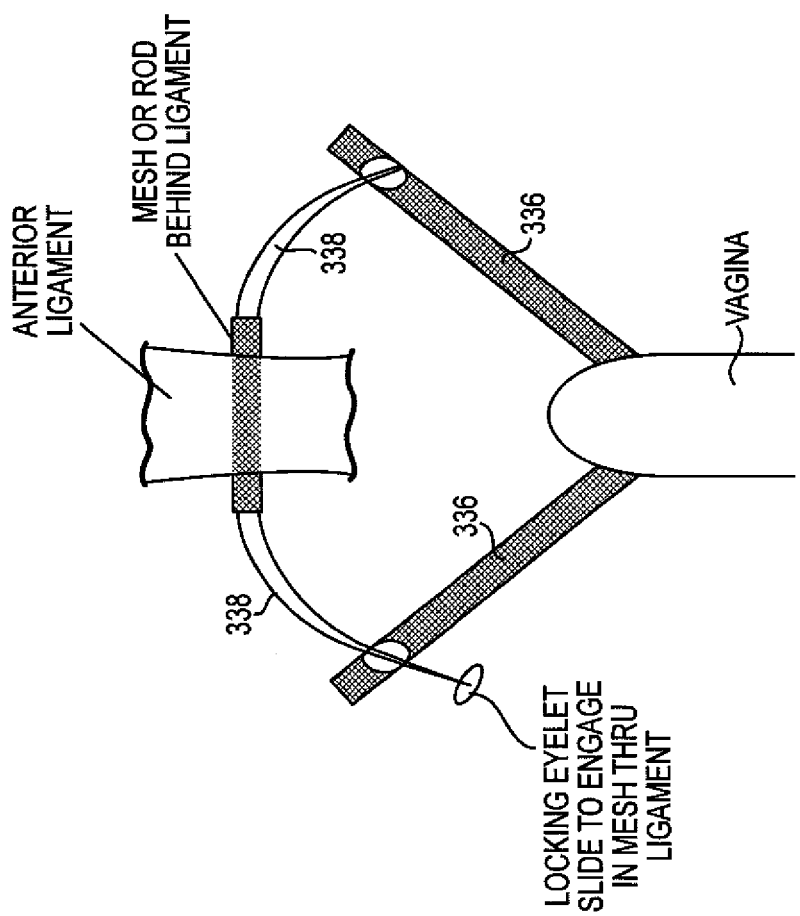

SACRUM FIXATION IDEAS

CAPIO-TYPE SUTURE (OR MESH) PASSING DEVICE

"VELCRO" OR TRUSS-PLATE FLAT PIECE THAT HAS LOTS OF SMALL HOOKS TO PRESS AGAINST LIGAMENT

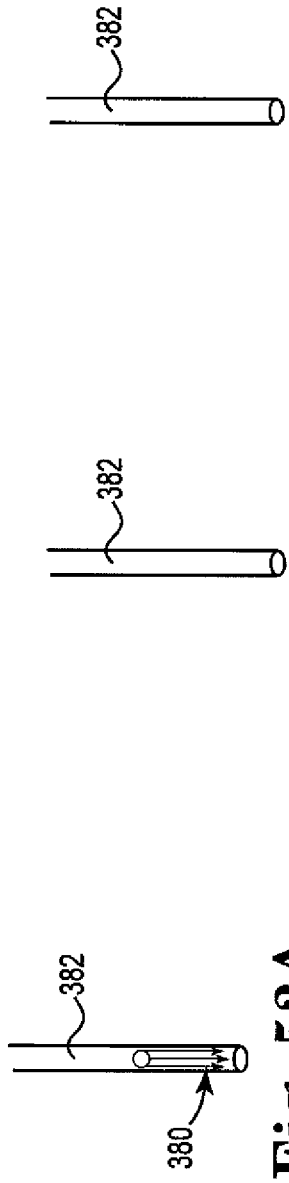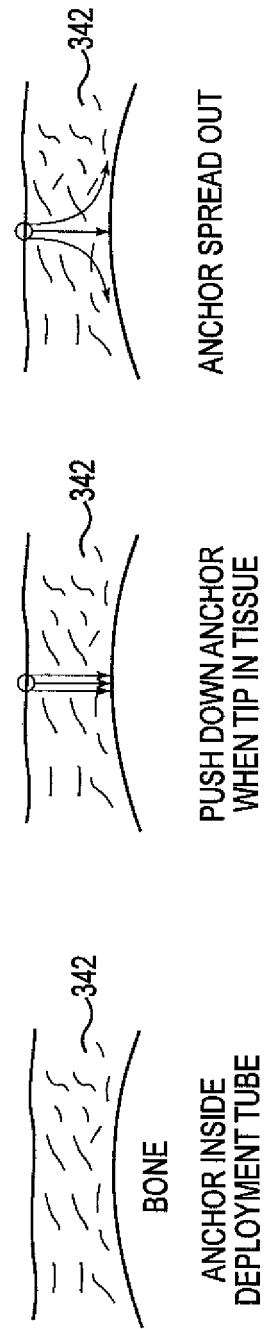

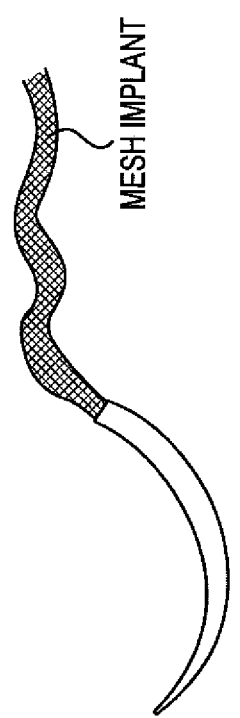
Fig. 53A  Fig. 53B  Fig. 53C

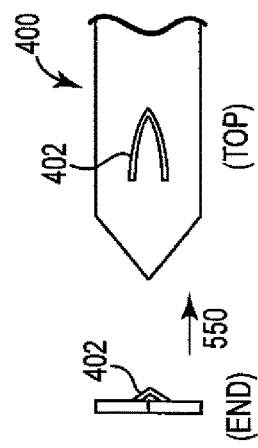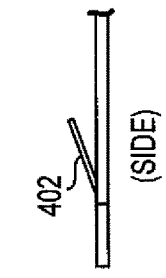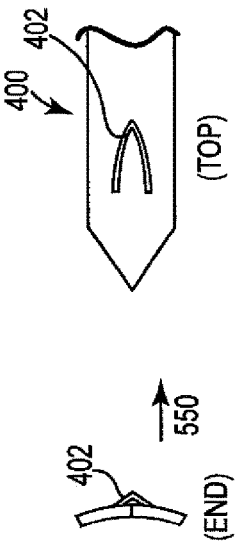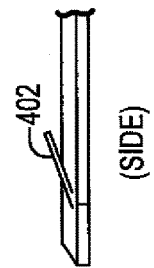

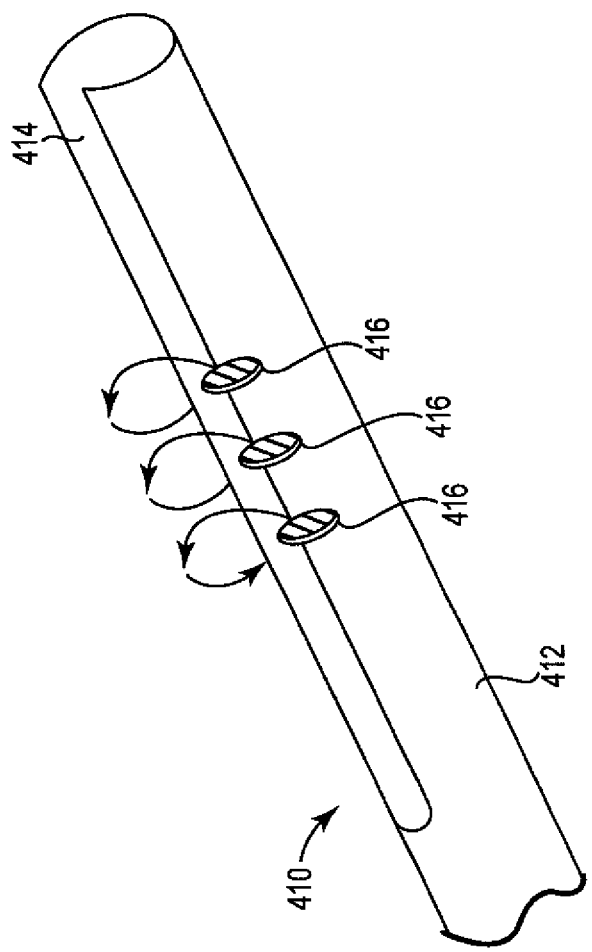

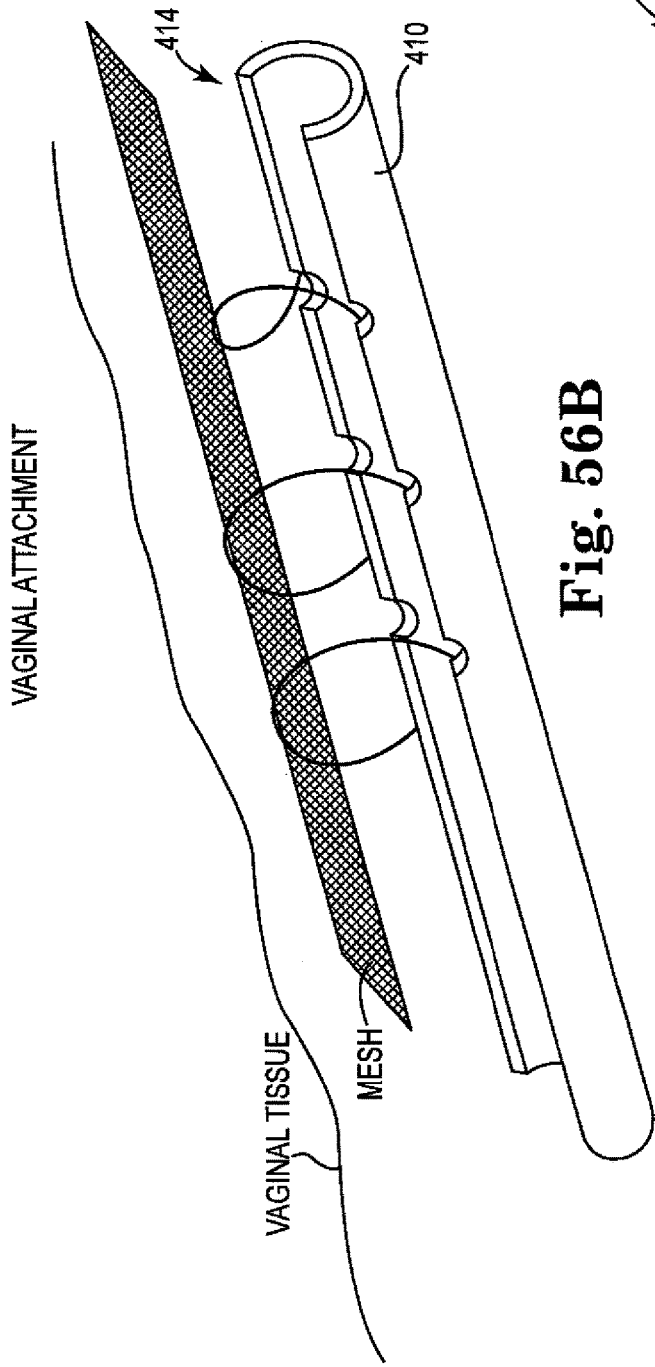
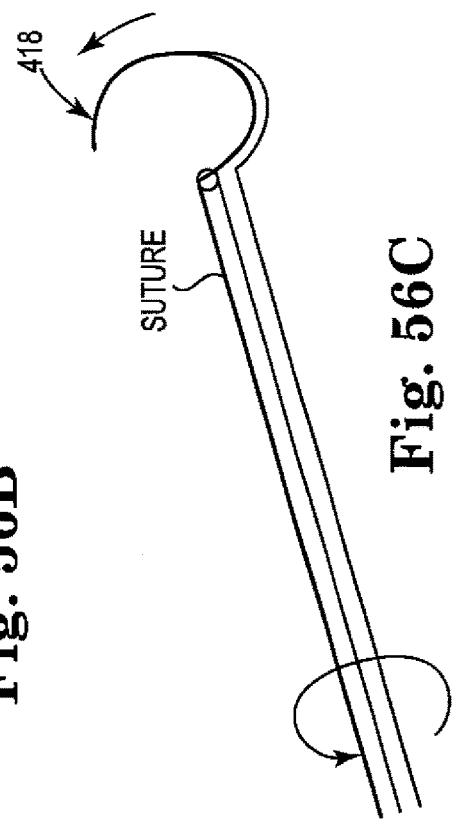
Fig. 56B
Fig. 56C

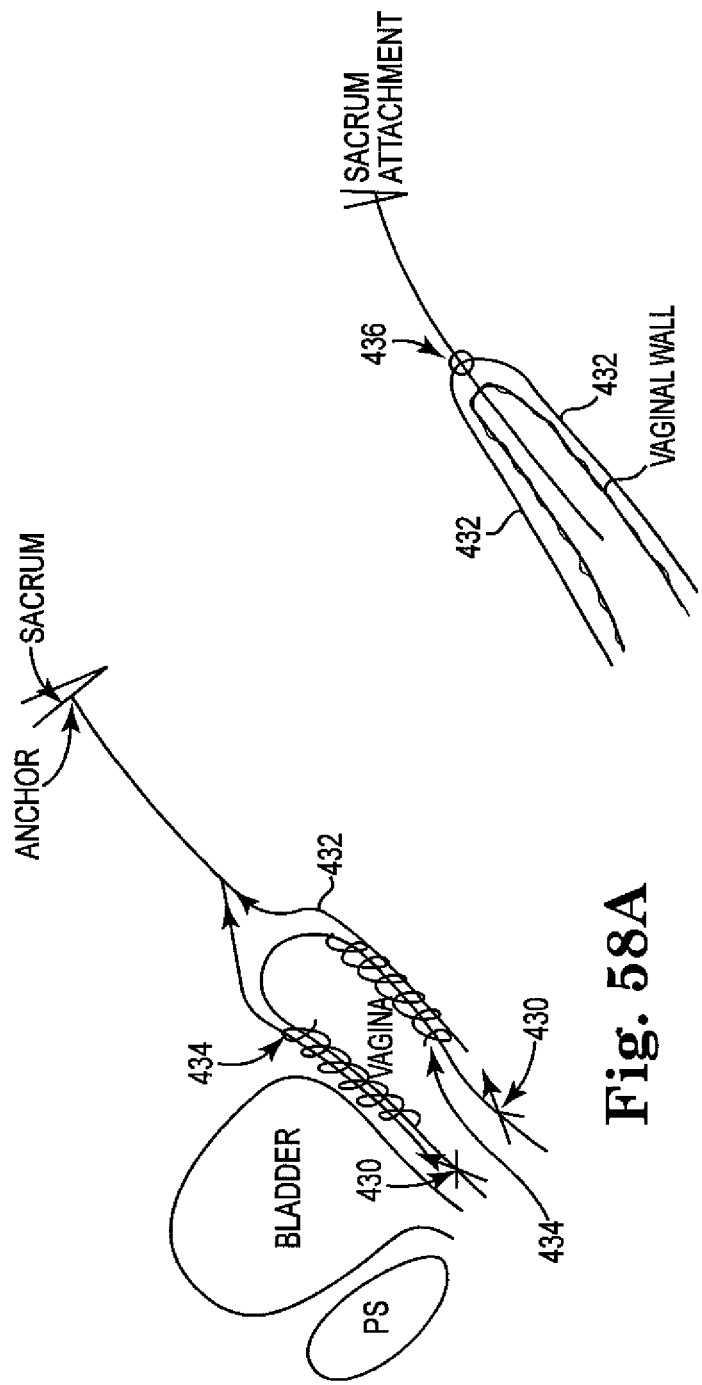

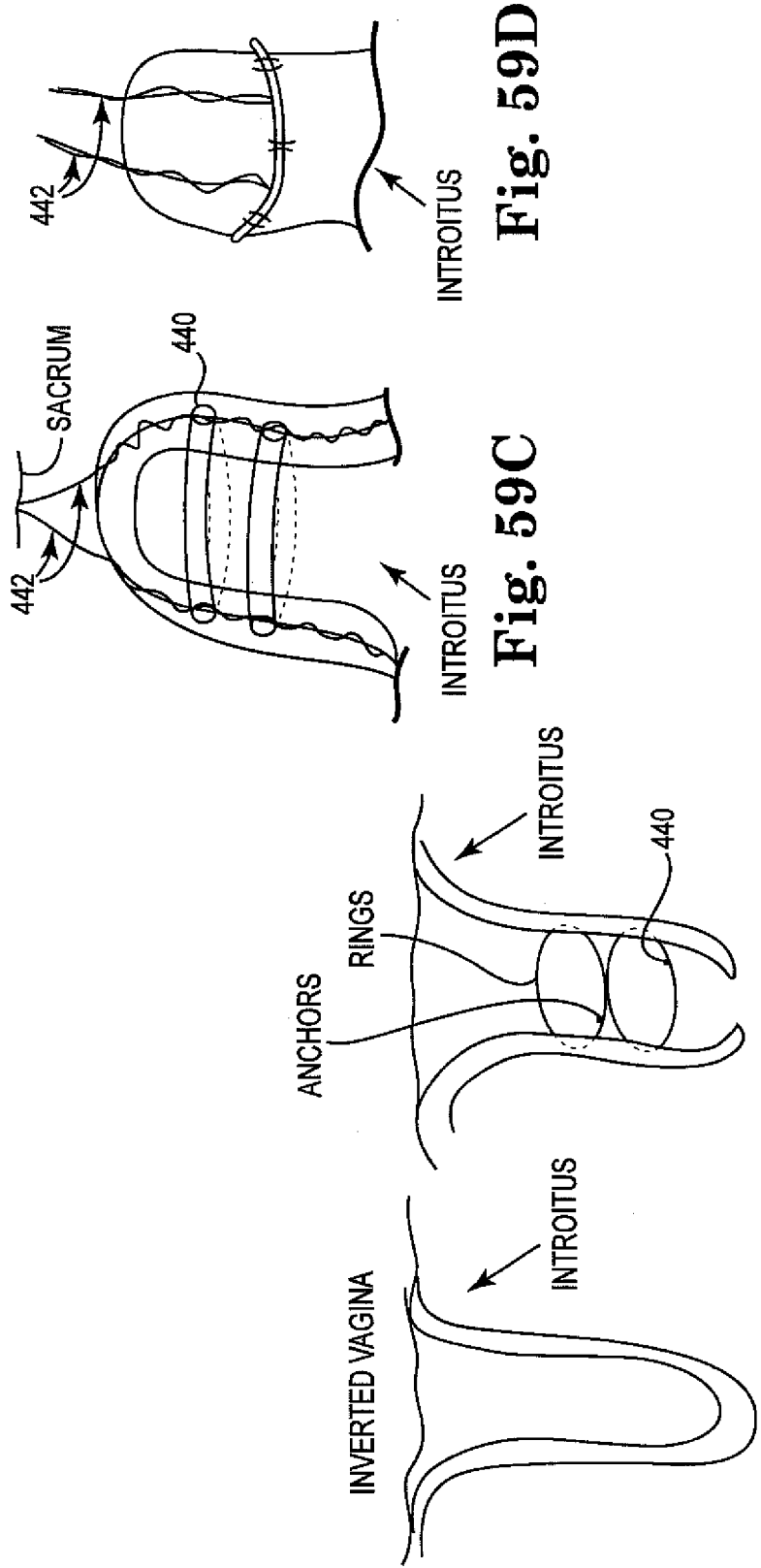

VAGINAL FIXATION

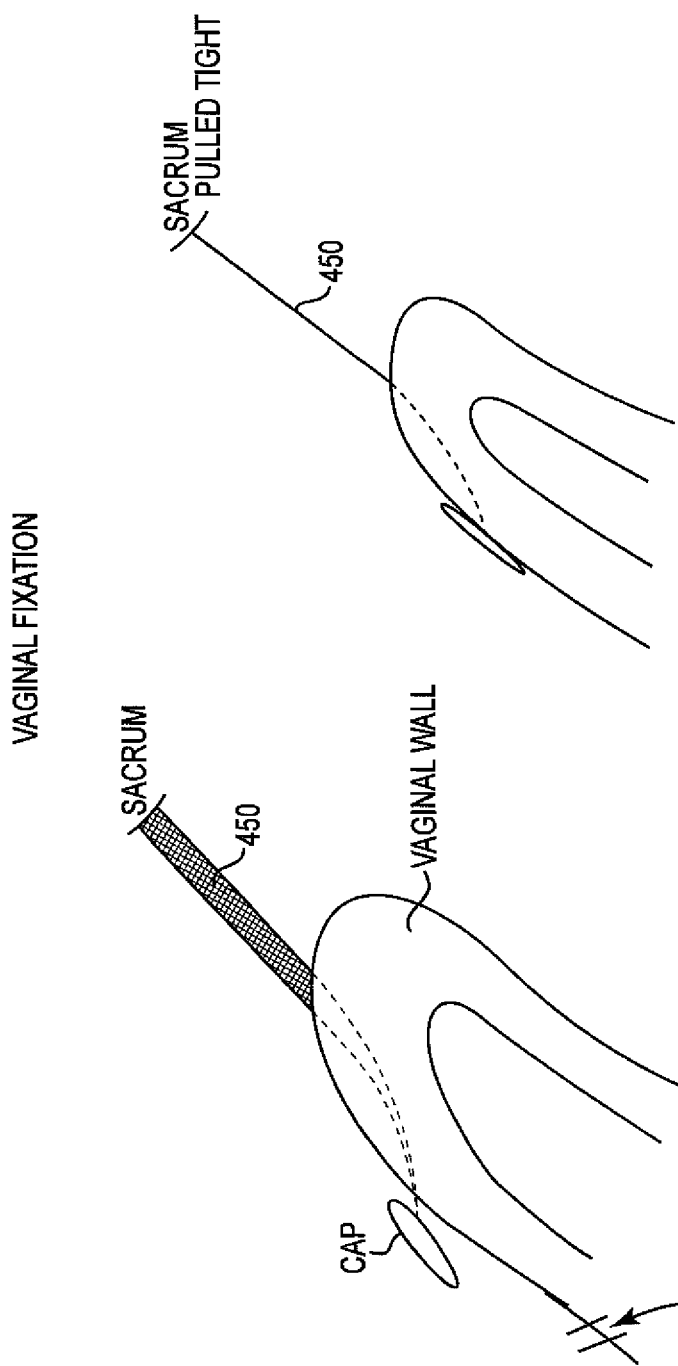

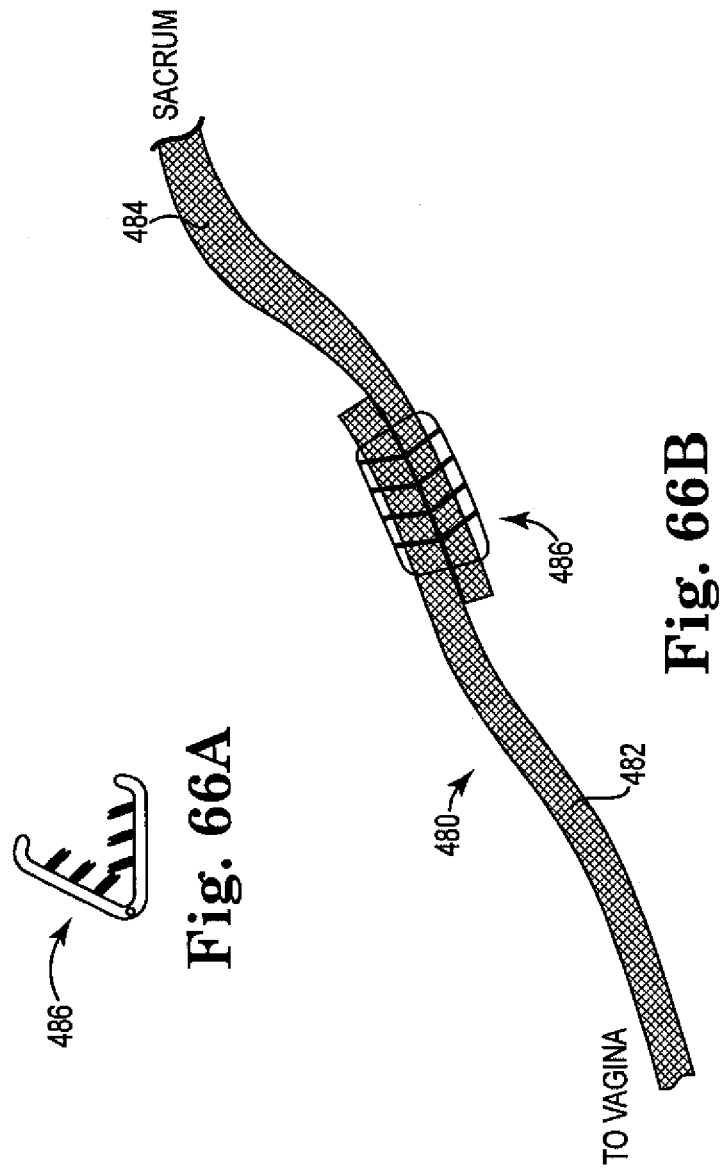

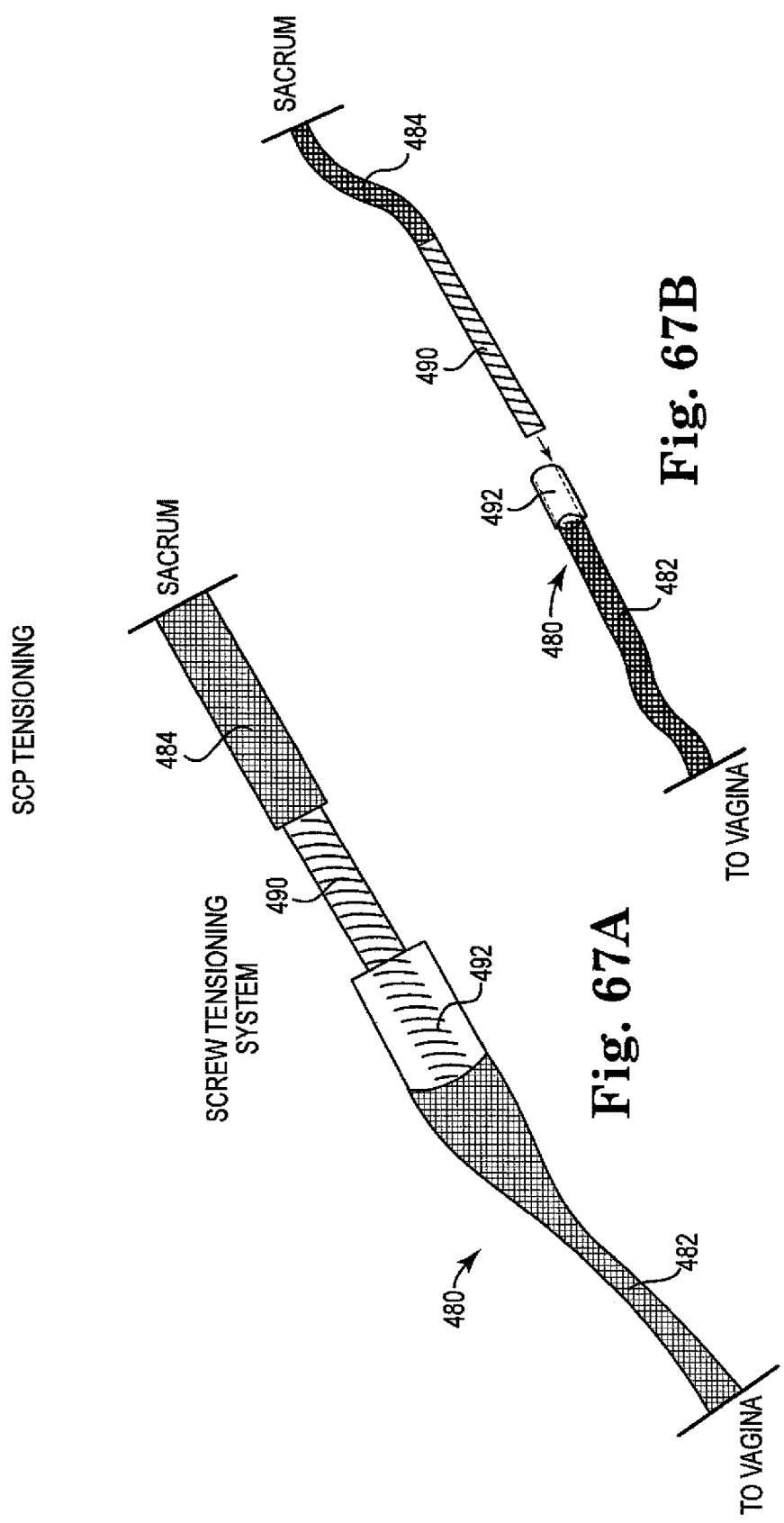

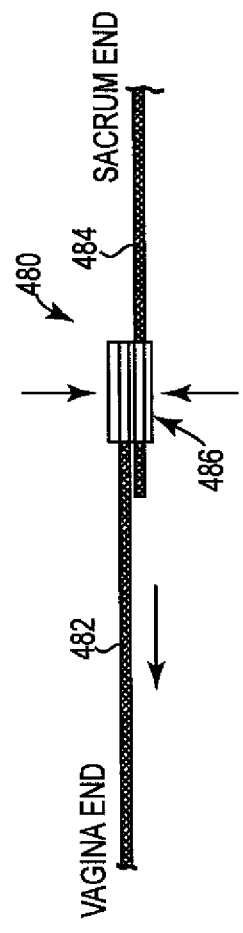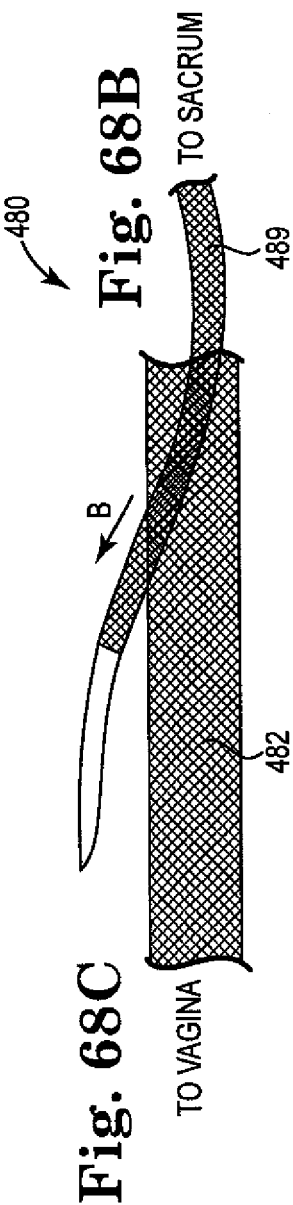

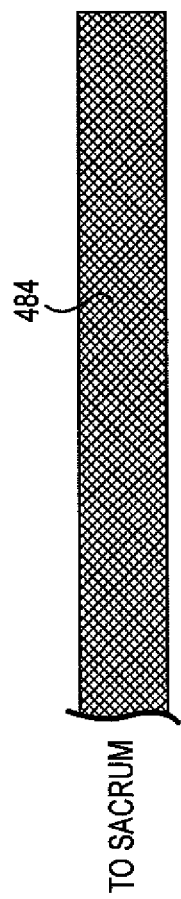
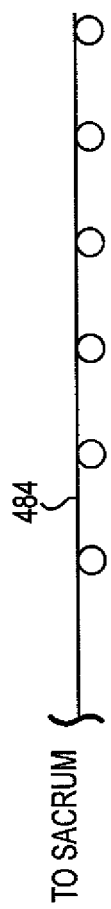
Fig. 69A
Fig. 69B
Fig. 69C
Fig. 69D

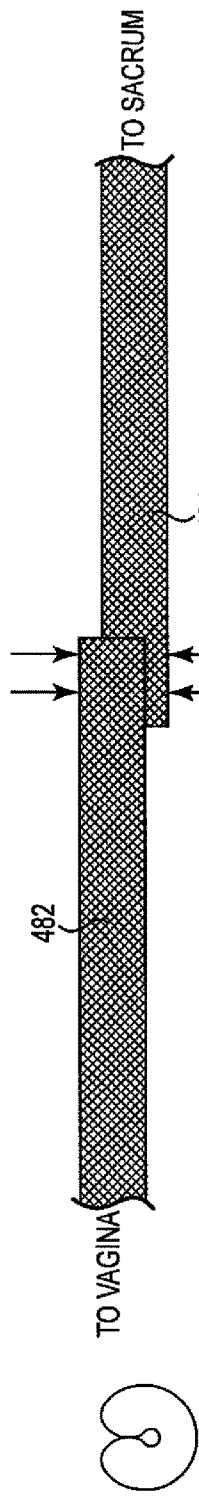
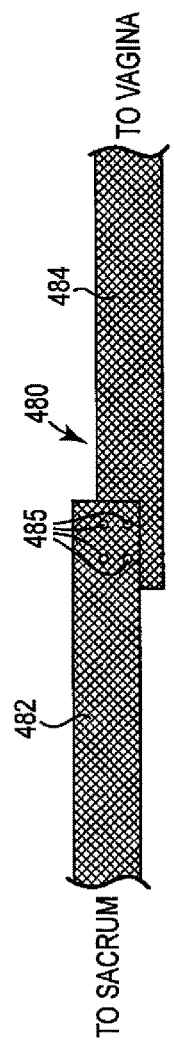
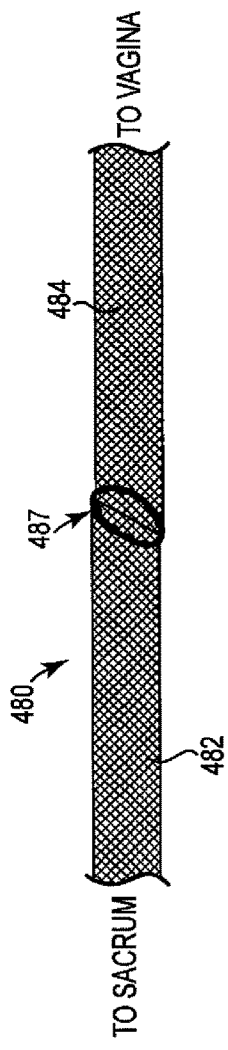
Fig. 70A  Fig. 70B  Fig. 70C  Fig. 70D

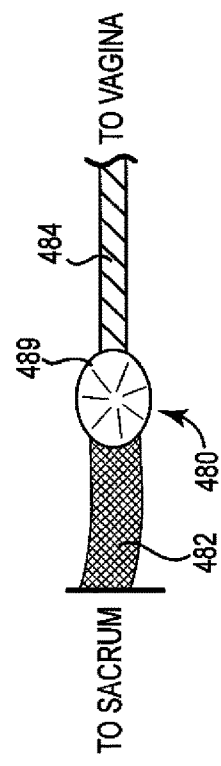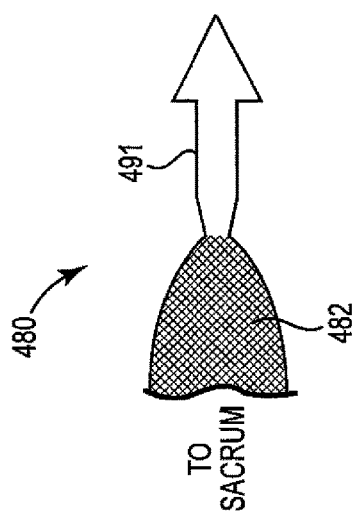
Fig. 71A
Fig. 71B

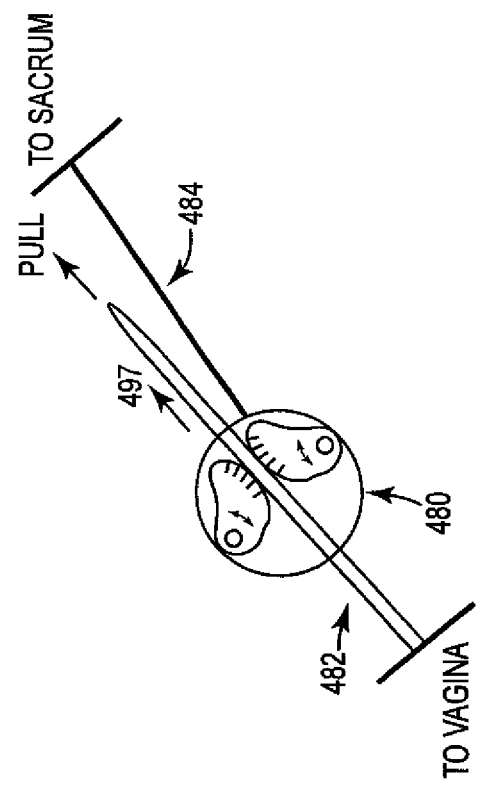
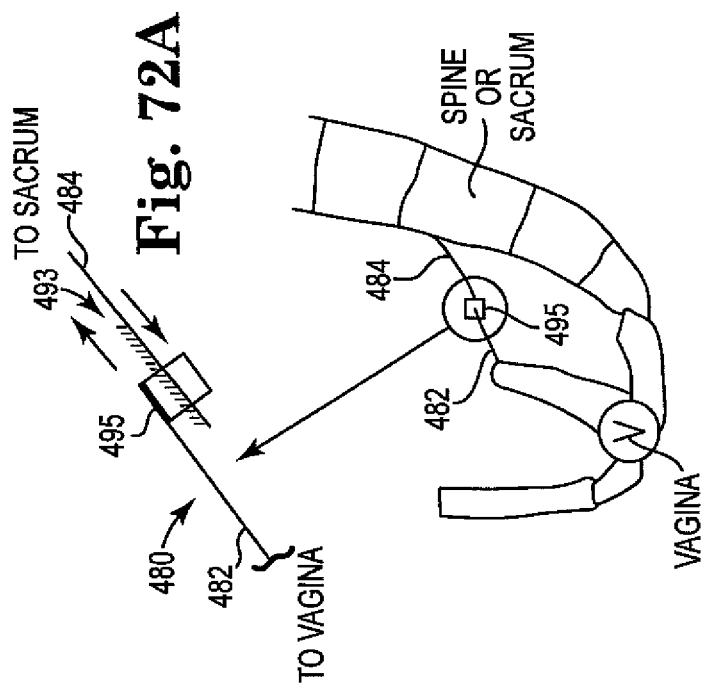
Fig. 72A
Fig. 72B
Fig. 72C
WIRE TIE/CAM LOCKS

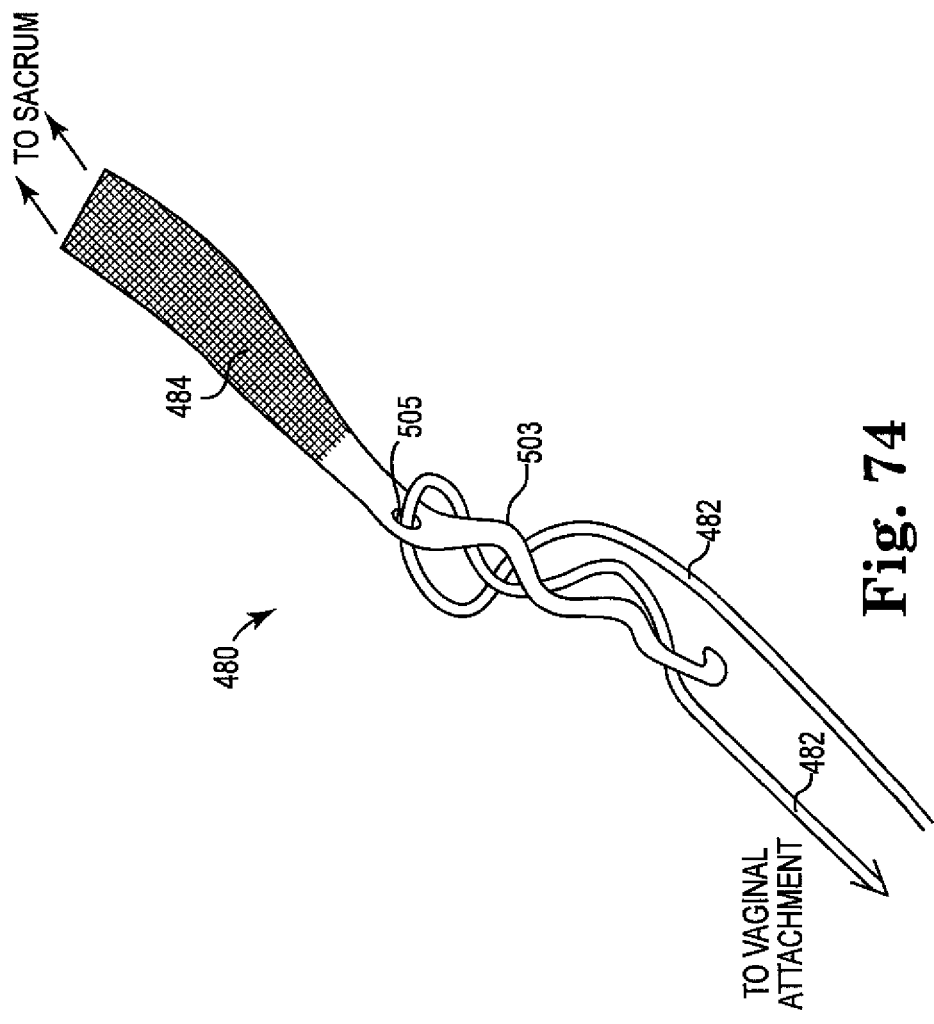

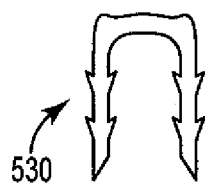
Fig. 75A
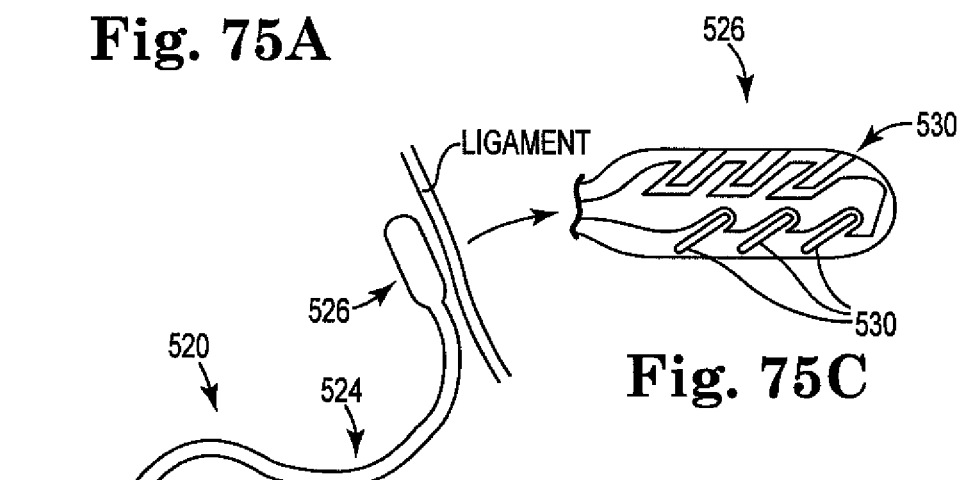
Fig. 75B
Fig. 75C
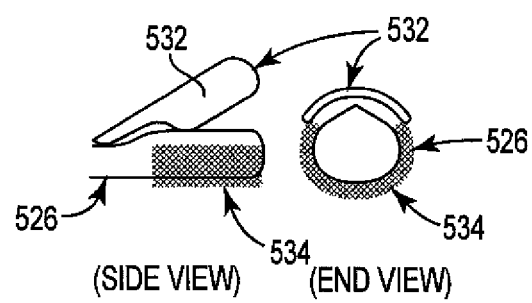
Fig. 75D

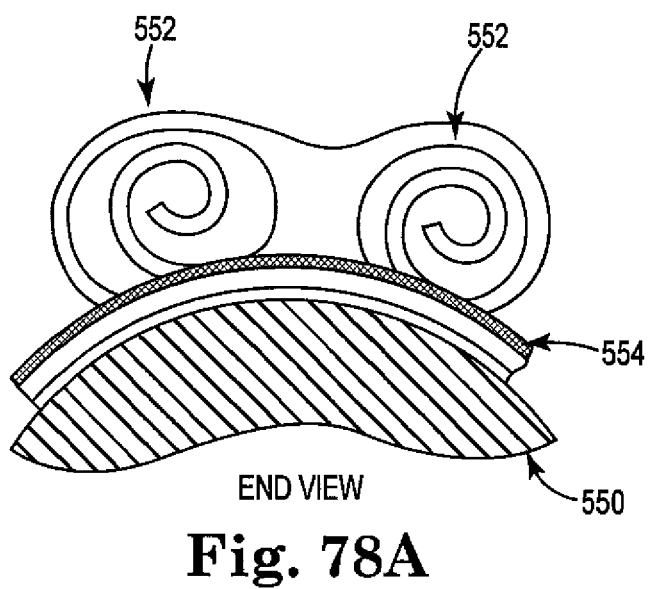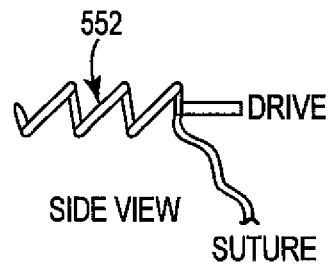
Fig. 78A
Fig. 78B

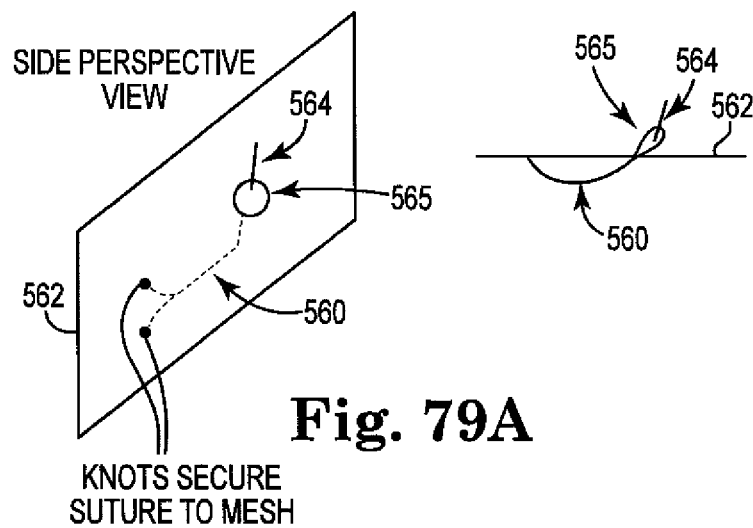
Fig. 79A
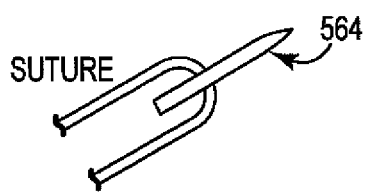
Fig. 79B
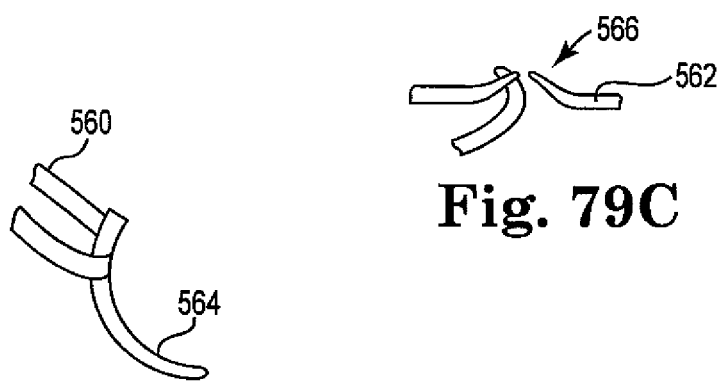
Fig. 79C
Fig. 79D

THIS CONCEPT USES A "PLIER" TYPE APPROACH FOR SEWING
THE MESH TO THE VAGINAL EPITHELIUM

THE ANTERIOR PROLAPSE MESH/SUPPORT COULD INCLUDE:

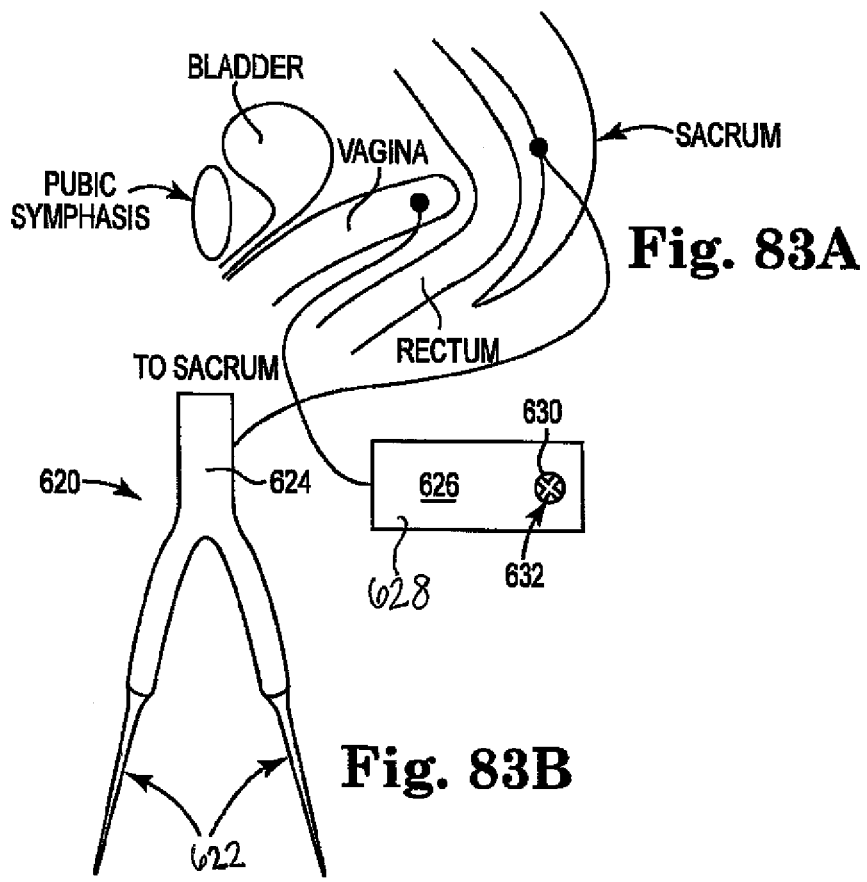
Fig. 83A
Fig. 83B
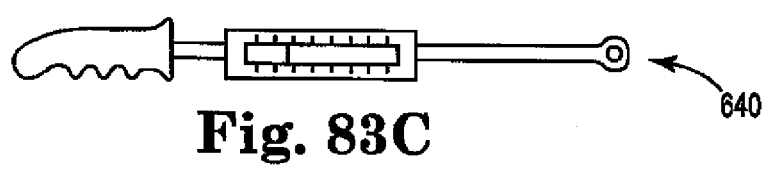
Fig. 83C
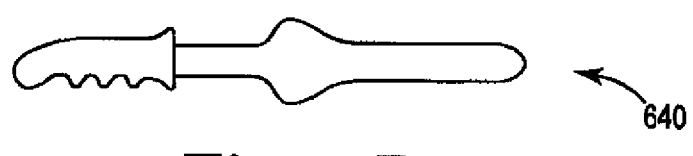
Fig. 83D

ADD. NYLON OR PET TUBE TO HOLD MESH COMPRESSED

THE FOLLOWING ALLOWS FOR A TRANS VAGINAL METHOD
FOR SUPPORTING THE LEVATOR

ELASTIC TYPE MESH TWO ANCHOR PARTS OR
EITHER SIDE WITH LOCKING EYELET TENSION ADJUSTMENT

SURGICAL DISSECTION TOOL

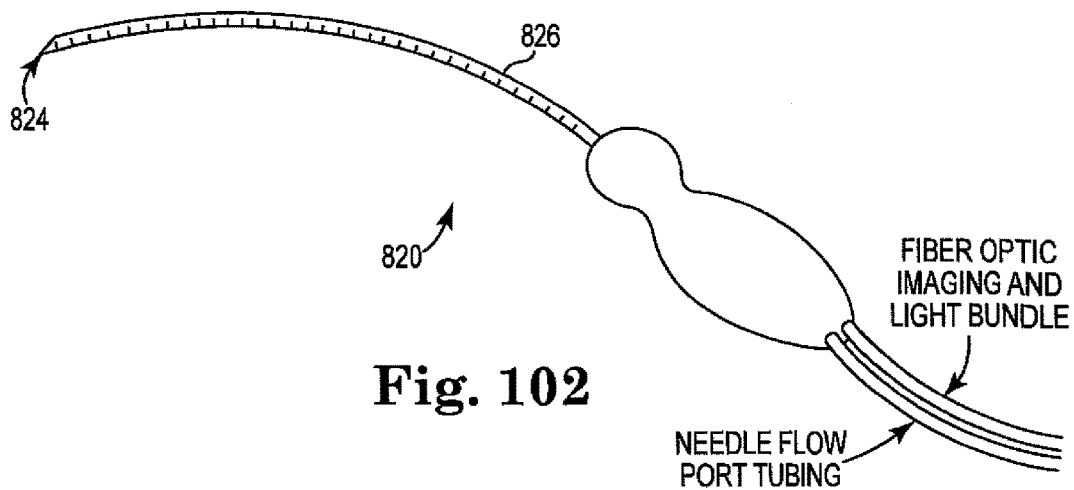
Fig. 102
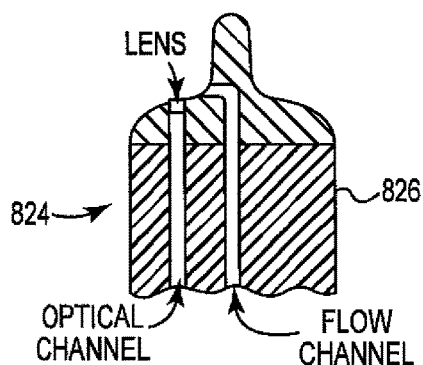
Fig. 103
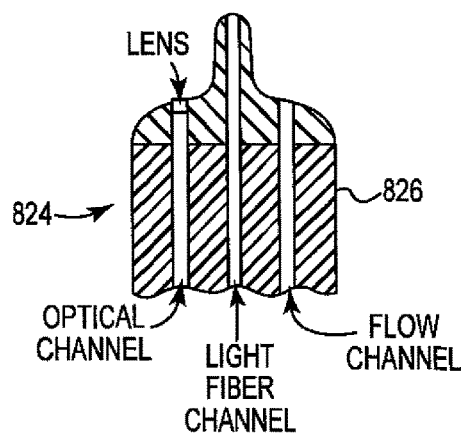
Fig. 104
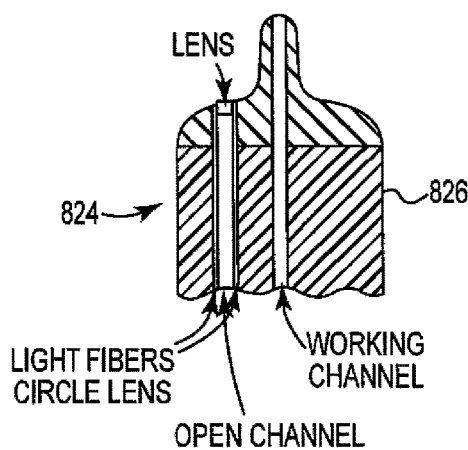
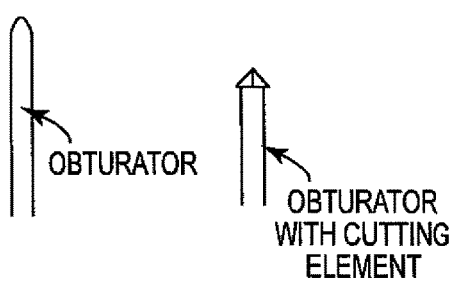
Fig. 105

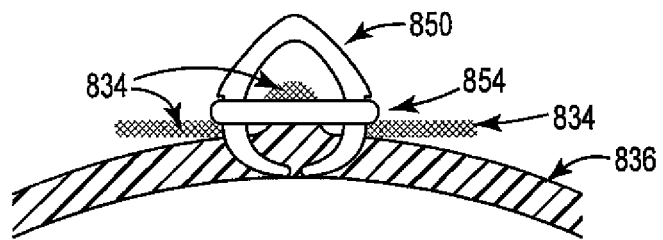
Fig. 111
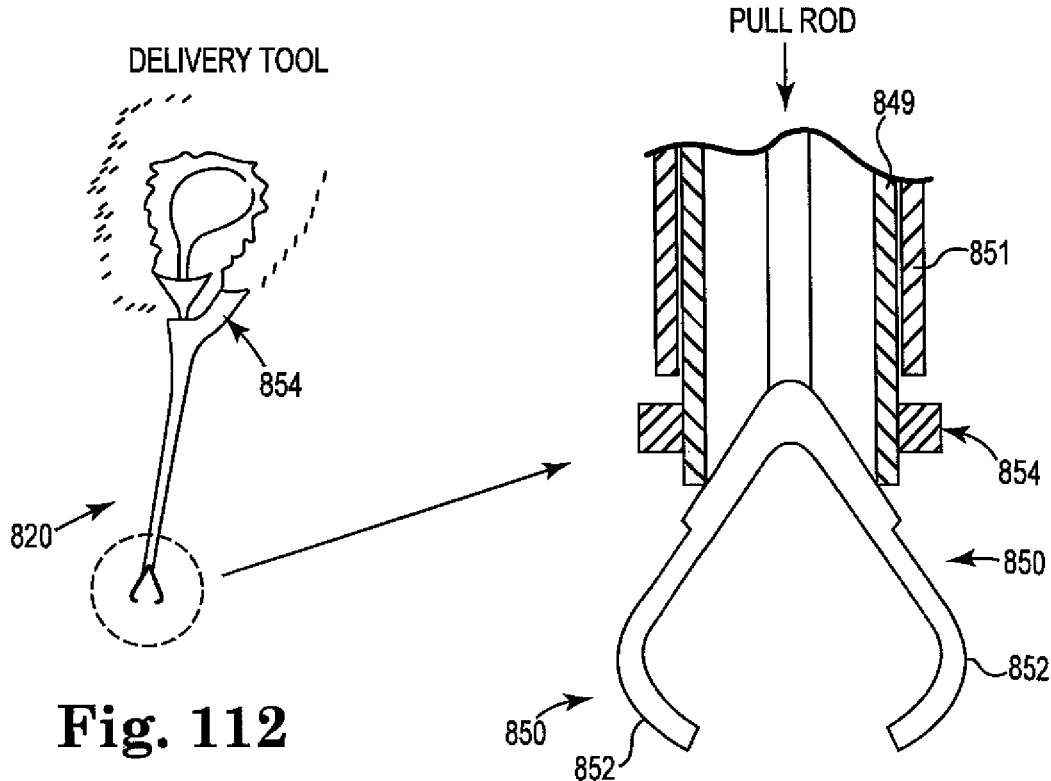
Fig. 112
Fig. 113

DRIVE MECHANISM

SYSTEMS, IMPLANTS, TOOLS, AND METHODS FOR TREATMENTS OF PELVIC CONDITIONS

PRIORITY CLAIM

This application claims the benefit from International No. PCT/US2010/062577, which was granted an International Filing Date of Dec. 30, 2010, which in turn claims priority to provisional application Ser. No. 61/291,188, filed Dec. 30, 2009, entitled SACROCOLPOPEXY SYSTEMS AND METHODS; provisional application Ser. No. 61/291,366, filed Dec. 31, 2009, entitled SURGICAL SYSTEMS AND METHODS; provisional application Ser. No. 61/291,370, filed Dec. 31, 2009, entitled SURGICAL TOOL AND PORT ACCESS SYSTEM AND METHOD; provisional application Ser. No. 61/291,373, filed Dec. 31, 2009, entitled EXPANDABLE MEANS TO VIEW SACRUM; provisional application Ser. No. 61/291,387, filed Dec. 31, 2009, entitled TRANSVAGINAL IMPLANTATION AND MESH TENSIONING SYSTEMS AND METHODS; provisional application Ser. No. 61/291,462, filed Dec. 31, 2009, entitled IMPLANTABLE MESH FIXATION SYSTEM AND METHOD; and provisional application Ser. No. 61/297,579, filed Jan. 22, 2010 entitled TRANSVAGINAL IMPLANTATION AND MESH TENSIONING SYSTEMS AND METHODS, each of these applications being incorporated herein by reference in their entireties.

FIELD OF THE INVENTION

The present invention relates generally to implants, anchors, tools, multi-functional tools, expansion members, devices, systems, apparatus, and related methods for treating pelvic conditions including but not limited to incontinence and prolapse conditions in men and women, for example by sacral colpopexy procedures.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

Abdominal sacralcolpopexy (SCP) is considered to be an especially efficacious treatment, but it can be complicated and is generally considered invasive.

There is a desire to obtain a minimally invasive yet highly effective implantable mesh that can be used to treat incontinence, and/or pelvic organ prolapse and other conditions.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies and the like.

Various surgical tools, structures, implants, anchors, multi-functional tools, expansion members ("retractors") and procedural improvements are disclosed herein.

Certain described embodiments relate generally to surgical methods and apparatus and, more specifically, to surgical tools having a tube adapted to provide port access and guidance to a surgical site. These embodiments involve various surgical tools and methods configured to facilitate guidance and passage of a tube or other expansion member to the surgical site or anatomy, such that sharp objects and tools can be passed without having to make multiple attempts from the incision to the anatomical target area. Certain of these described embodiments relate generally to various means, devices, and techniques for providing a clear view of the sacrum through a vaginal incision. In several examples, this is provided by way of an expandable device that can be inserted into the vaginal incision and then expanded or dilated.

Certain embodiments relate generally to fixation or attachment devices ("anchors") and related methods for placing a pelvic mesh implant, and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include a tissue support portion and one or more anchors, arms and the like. In addition, disclosed are combination devices (implants, tools, and anchors, etc.) and related method useful for anterior or posterior prolapse repair with other treatments for pelvic floor disorders such as urinary incontinence, pelvic floor decent (levator avulsion), and/or sacral fixation. Exemplary levator ani support devices can be introduced through a vaginal incision to tie in with conventional transvaginal mesh repairs and other applications. Moreover, various disclosed embodiments allow the physician to tension the vaginal apex through a vaginal incision.

BRIEF DESCRIPTION OF THE DRAWINGS

FIGS. 4-5 depict multi-purpose tooling configurations in accordance with embodiments of described inventions.

FIGS. 6-17 depict various tool ("needle") configurations in accordance with embodiments of described inventions.

FIGS. 24A-24D depict an expansion device and technique in accordance with embodiments of described inventions.

FIGS. 25A-25F depict an expansion device and technique in accordance with embodiments of described inventions.

FIGS. 26A, 26B depict an expansion device and technique in accordance with embodiments of described inventions.

FIG. 27 depicts an expansion device ("expansion member") and technique in accordance with embodiments of described inventions.

FIGS. 28A, 28B, and 28C depict an expansion device and technique in accordance with embodiments of described inventions.

FIGS. 29A-29D depict an expansion device and technique in accordance with embodiments of described inventions.

FIGS. 31A-31C depict an expansion device and technique in accordance with embodiments of described inventions.

FIGS. 32A, 32B depict an expansion device and technique in accordance with embodiments of described inventions.

FIGS. 33A-33F depict an expansion device and technique in accordance with embodiments of described inventions.

FIGS. 34A, 34B, 34C, 34D and 34E-34J depict an expansion device and technique in accordance with embodiments of described inventions.

FIGS. 35A-35E depict an expansion device and technique in accordance with embodiments, of described inventions.

FIGS. 36A-36C depict an expansion device and technique in accordance with embodiments of described inventions.

FIGS. 37A-37D depict an expansion device and technique in accordance with embodiments of described inventions.

FIGS. 38A-38B depict an expansion device and technique in accordance with embodiments of described inventions.

FIGS. 39A, 39B depict an expansion device and technique in accordance with embodiments of described inventions.

FIGS. 40-55 depict various embodiments for securing mesh implants to the sacrum of a patient in accordance with embodiments of described inventions.

FIGS. 56, 57, and 58-61 depict various embodiments for securing mesh implants to the vagina of a patient in accordance with embodiments of described inventions.

FIGS. 62-74 depict various embodiments for adjusting the tension of the vaginal apex when secured to the sacrum in a sacralcolpopexy procedure in accordance with embodiments of described inventions.

FIGS. 75-77 depict various embodiments for a transvaginal approach for a sacrocolpopexy targeting the mesh fixation to the anterior ligament of the sacrum in accordance with embodiments of described inventions.

FIGS. 78-81 depict various embodiments of methods and devices for fixating mesh to the vaginal wall in accordance with embodiments of described inventions.

FIGS. 83-84 depict a vaginal apex support device in accordance with embodiments of described inventions.

FIGS. 98-102 depict various surgical dissection tools or systems, including those adapted for use with known or modified introducer needles, in accordance with embodiments of described inventions.

FIGS. 103-107 depict various needle tip configurations adapted for use with the present invention, such as working channels, optical channels, lenses, sheaths, balloons, cutting blades, and the like, in accordance with embodiments of described inventions.

FIGS. 109-116 depict various systems or methods for facilitating sacral tissue fixation in accordance with embodiments of described inventions.

DETAILED DESCRIPTION

Figure 1:
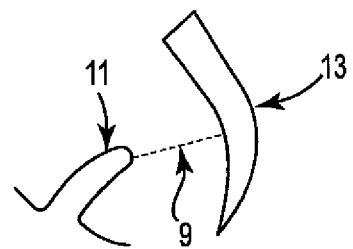
FIGS. 1-3 depict various systems and fixation elements or features in accordance with embodiments of described inventions.

Pelvic floor disorders include cystocele, rectocele, enterocele, and uterine and vaginal vault prolapse, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures are surgical methods that place a sling to stabilize or support the bladder neck or urethra. They are typically used to treat incontinence. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534 and 6,110,101.

A sacral colpopexy is a procedure for providing vaginal vault suspension. It may be performed through an abdominal incision, a vaginal incision, or laparoscopically. Complications include mesh infection, mesh erosion, bowel obstruction, ileus, and bleeding from the presacral venous complex. Typically, this procedure is accompanied by an abdominal enterocele repair and cul-de-sac obliteration.

A sacral colpopexy entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. An implant such as a synthetic mesh can be carefully customized or assembled into a special shape by the surgeon. According to some procedures, a surgeon manually cuts a sheet of the mesh and stitches elements of the mesh to form the special shape. The literature reports surgeons suturing mesh material into various T-shaped articles. See Winters et al., *Abdominal Sacral Colpopexy and Abdominal Enterocele Repair in the Management of Vaginal Vault Prolapse*, Urology 56 (Suppl 6A) (2000): 55-63; and Paraiso et al. *Laparoscopic Surgery for Enterocele, Vaginal Apex Prolapse and Rectocele*, Int Urogynecol J (1999

In some SCP procedures that also involve a hysterectomy, an implant can attach to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy).

As used herein, the term "anchor" refers non-specifically to any structure that can connect an implant to tissue of a pelvic region. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a bone anchor, any of the structures described herein to be useful to connect an implant to soft tissue or bone of a pelvic region, or the like.

Referring generally to FIGS. 1-19, various embodiments of tools or systems 10 and methods are shown for use in methods for treating pelvic conditions such as a method of performing a sacral colpopexy ("SCP"). Various portions of a system 10 can be constructed of polymer materials, metal, or other biocompatible or acceptable surgical apparatus materials.

Figure 2:
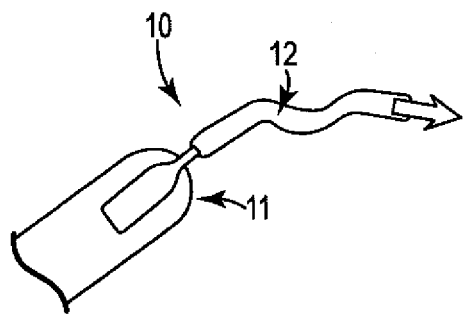
Figure 3:
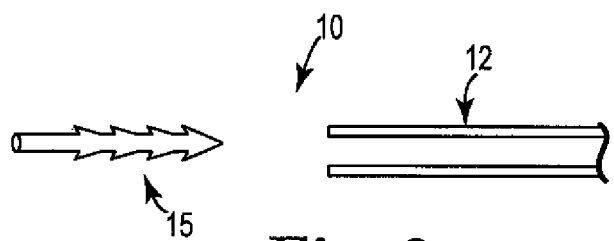

Referring generally to FIGS. 1-3, SCP apical fixation elements are configured to create a structure that closely mimics or replicates the uterosacral ligaments, between posterior vaginal tissue (e.g., a "vaginal vault," "vaginal apex," "apical vagina," or "vaginal cuff") and a tissue at a region of sacral anatomy. Namely, one or more small elastic silicone (or other elastic material) implant (e.g., tubes, strips, tape, etc.) 12 or elastic (solid or hollow) rods can be connected to the vaginal apex (11), and to tissue at a region of sacral anatomy (e.g., at or near sacrum (13)) near the original fixation point of the uterosacral ligaments 9 (FIGS. 1-2). Such a configuration, using an elastic implant, provides at least two distinct benefits. First, the need for critical adjustment of the vaginal apical tension is decreased (thus, decreasing physician dependency and patient comfort/procedural complexities). Second, the elastic properties of the natural anatomical bodies or structures are mimicked by the use of an elastic material for elastic implant 12, that moves and reacts to activity in a manner similar to the natural anatomical structures.

An elastic material for implant 12 can allow the elastic implant to stretch and accommodate various implant techniques and patient activity and movement. The elastic material for this elastic implant embodiment can take on any form or shape having a generally flexible construction. The elastic material may be of a natural or synthetic polymeric material that provides an elastic implant with elasticity that mimics vaginal tissue or tissue of a uterosacral ligament. For instance, an elastic implant having a spring rate of less than 25 lbf/inch (e.g. from 2 to 25 lbf/inch or from 5 to 20 lbf/inch) can be a desirable goal, while various other configurations and flexibility ratings are envisioned as well. Examples of suitable elastic materials may include silicone rubber, natural or other synthetic rubber, polyolefin, an implant that contains a mechanical elastic spring, and the like.

The elastic implant may have a length to reach from a vaginal vault or other posterior vaginal tissue, to tissue at a region of a sacrum (e.g., a sacral promontory, fascia, a nearby ligament (the sacrospinous ligament, uterosacral ligament, anterior longitudinal ligament), or fascia), with a desired degree of tension (e.g., due to stretching) placed on the elastic implant. The elastic implant can be of a relatively flat form or material such as an elongate elastic mesh, strip, or tape, or tubular. The implant may be made of a single elastic material or an implant may be a composite device constructed of multiple components, one or all of which are elastic.

A single specific example of an elastic implant is shown at FIG. 2. Elastic implant 12 is an elastic material that reaches between posterior vaginal tissue 11 and a region of sacral anatomy (not shown). Anchor 7 can be used to secure a distal end of elastic implant 12 at a region of sacral anatomy. A proximal end can attach to vaginal apex 11 by any useful method.

As one example, FIG. 3 illustrates elastic implant 12 in the form of an elastic polymeric tube having two opposing ends, a first (proximal or anterior) end configured to engage or connect tissue at or proximal to a vaginal vault, and a second (distal or posterior) end configured to engage or connect to tissue at a region of sacral anatomy. The first end can be connected directly or indirectly to vaginal tissue such as by use of a suture, staple, biological adhesive, anchor, etc. For example the first end may be connected via an intermediate structure such as a barbed anchor (15) having a barbed end configured to fit within tube 12; the opposite (proximal) end of barbed anchor (15) can be configured to be directly or indirectly secured to vaginal tissue by any desired anchor or other means such as a clamp, self-fixating tip, soft tissue anchor, or the like, such as an anchor described herein. The second end of tubular elastic implant 12 can be connected directly or indirectly to tissue of a sacral region such as by use of a suture, staple, biological adhesive, or another anchor described herein or elsewhere, or may be secured to tissue of a sacral region by any other desired structure such as a clamp, self-fixating tip, soft tissue anchor, bone anchor, or the like.

According to multi-functional tools illustrated a FIGS. 4 and 5, visualization and fixation challenges normally associated with a transvaginal SCP procedure are addressed and remedied. Namely, a multi-functional tool 14 is provided and can be used for one or more of the combined functions of: dissection (e.g., by any means such as a blade, hydrodissection, or otherwise), blunt dissection, viewing (i.e., "visualization"), illumination, fluid delivery, irrigation, suction, and placing anchors (bone anchors, soft tissue anchors such as a self-fixating tip, sutures, etc.) into a desired target tissue. FIG. 4 is a side perspective view of tool 14 and FIG. 5 is an end view directed at the tip 16. Optionally tip 16 can articulate as much as 90 degrees, or optionally or alternately rotate, to navigate around critical anatomy. Using tool 14 a physician can complete multiple tasks with one hand, in one pass, and keep the other hand free to complete other portions or steps of the SCP procedure. Tissue trauma can be reduced and overall visibility and troubleshooting abilities are improved.

FIG. 5 is a front (end) view of the tool tip 16 depicting an exemplary combination of multiple functions and structures of a tool 14, e.g., a light source (16*a*), lens for a camera or other optical viewing function (16*b*); fluid (e.g., liquid) dispensing port, e.g., "irrigation port" (16*c*) useful to dispense a gas, water, saline, or other liquid or gaseous fluid; suction port (16*d*) useful to place vacuum or suction at tool tip 16, e.g., to remove liquid of gaseous fluid; and anchor port (16*e*) useful to manipulate an anchor and place the anchor at or into tissue of a pelvic region, the anchor being any form such as a suture, clamp, dart, self-fixating tip, bone anchor, or any other anchor or securing or fixation element as described herein useful to secure an implant to tissue. Each of these features of tip 16 is in communication through a lumen, optical connection, mechanical connection, or electronic connection, as necessary, with a proximal end of device 14. The proximal end (see FIGS. 4 and 14) can include a handle or handles for manipulation by a surgeon or other user, and may additionally include one or more connection to allow communication with, operation of, or manipulation of each structure, port, and functionality at tip 16.

In various embodiments, suction port (16*d*) and irrigation port (16*c*) could share the same distal tip 16 hole or opening feature.

Light source 16*a* can be any light source that can be a source of light at the distal end or tip 16 of tool 14. Light source 16*a* may be connected to a light source (bulb, light emitting diode (LED), LCD, or the like) at the proximal end, by fiber optics, or may include a light bulb or LED or LCD light source at the distal end of tool 14 connected to the proximal end by wiring. Viewing function 16*b* may be a miniature electronic camera located at tip 16 that communicates electronically with the proximal end, or may include a lens and an optical fiber extending through the shaft of tool 14 and having one (distal) end at tip 16 and another (proximal) end at the proximal end of tool 14, the proximal end being in viewing communication with an electronic camera. The light source (16*a*) and viewing function (16*b*) may or may not share the same port on the tip 16.

Articulation of tip 16 could vary in range and could exceed 90 degrees, and could also articulate in multiple dimensions, or may optionally rotate. In addition, anchor port (16*e*) could be any configuration or located within any portion of the tip 16 or at a location along the adjacent shaft.

Tip 16 can also include an anchor port 16*e*, which includes an engaging structure (e.g., "anchor interface") such as a needle tip capable of engaging an anchor. The engaging structure has a size and shape that corresponds to and is able to engage or grasp a portion of the anchor, e.g., allowing the anchor interface to hold the anchor during passage of tip 16 through a vaginal opening and to a region of sacral anatomy, where the anchor interface can be activated by a mechanism at the proximal end to place the anchor securely into tissue of a pelvic region. The placement can be guided by viewing through the viewing function 16*b* and using light source 16*a* to illuminate the tissue placement.

Tool 14, or portions thereof, can be constructed of various known and acceptable materials, including polymers, PEEK, stainless steels, polycarbonate, and the like. The overall size of the tool can vary greatly. For instance, one embodiment can range from an outer diameter of 0.200 to 1.00 inches. A length of the shaft can be sufficient to extend from an external location near a vaginal introitus, into a vagina and through a vaginal incision at the vaginal vault or cuff, then to access a sacrum. Other size and dimensions for the tool 14 are also envisioned. As indicated, the distal end may optionally include a steering mechanism that allows the distal end to be bent in two or three dimensions by manipulating a steering mechanism at the proximal end.

Various other embodiments of devices and method are illustrated at FIGS. 6-17, including needle systems 20 that include a tool having a handle 19, needle shaft 23 that comprises optional viewing (visualizing, or optic) and light (illuminating) features for lighting and viewing a pelvic location for placement of an implant or anchor, and related methods.

Traditional pelvic implant installation procedures (e.g., SCP procedures) may be performed through an abdominal opening or laparoscopically. As such, special skills and equipment are needed to complete the procedure effectively. And abdominal wounds are created. Described multi-functional tools can provides a minimally invasive procedure with no abdominal wounds or potential organ perforation or dissection, with useful distal end functionality such as an anchoring functionality, viewing and lighting functionalities, steering, suction, dissection, anchor delivery, implant delivery and fluid delivery. By use of an implant delivery tool having viewing and lighting functions, clear visualization of internal tissue is provided for needle passage and anchoring of an implant, e.g., to a sacrum. A physician is able to optically (visually) guide a distal end or shaft of an implant delivery tool (i.e., "needle") with direct viewing, visually identify potential areas of risk, and guide or steer the needle to a desired target tissue site for placing an anchor or implant. A faster learning curve is provided for physicians to safely pass the needle with the aid of a scope and optical viewing, and the knowledge from scope usage in surgery is applied to and benefits surgical procedures.

An exemplary needle system 20 (having optical and visual functionality) can include a tool 14 that includes an elongate shaft, the shaft including or more separate or integrated "shaft" structure and an anchor interface structure 22*d*, and can be constructed of flexible or rigid biocompatible materials such as rigid or flexible polymer, stainless steel (high strength and high modulus of elasticity), etc. The shaft or shaft assembly can be of a relatively small diameter, but with enough rigidity to allow useful and safe passage and guidance.

Figure 6:
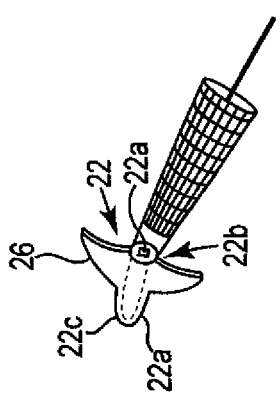
Figure 7:
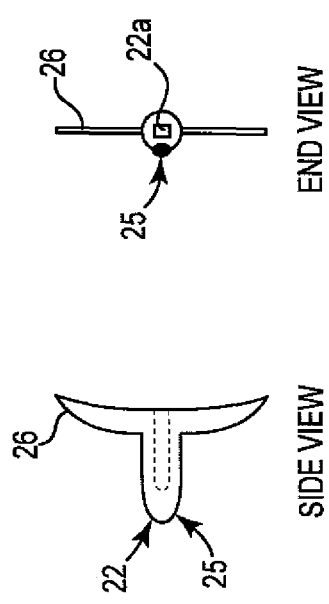
Figure 8:
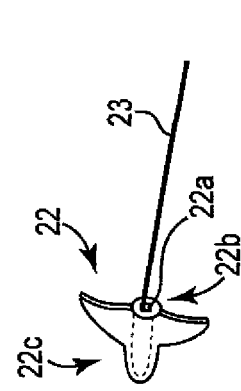

Referring to FIGS. 6, 7, and 8, one or more anchor 22 can be constructed to fix to a tissue at a region of a sacral anatomy, but also to allow light to pass into or out of a viewing or light feature of an insertion tool. For example anchor 22 can include an aperture, lens, or opening for passing light, and may be constructed of a transparent or translucent biocompatible material suitable for implantation, and also that allows visual lighting and viewing for guidance within the patient. For instance, various anchors and like attachment devices, tools, systems and methods as disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382, can be employed with the present invention. Accordingly, the above-identified disclosures are fully incorporated herein by reference in their entirety.

In such embodiments, a system 20 can include an elongate shaft of a multi-functional tool with a fiber optic light source and fiber optic image bundle integrated therein (e.g., as shown at FIGS. 9 and 13-17). System 20 can include features that will facilitate tissue anchoring through delivery of the one or more anchors 22 (e.g., as illustrated at FIGS. 6, 7, and 8). FIG. 6 shows a soil tissue anchor (e.g., "self-fixating tip") 22 that includes an internal channel (or "needle interface" 22a) extending from a proximal end (22b) (connected to suture 23) to a distal end (22c). Channel (or "needle interface") 22a can be adapted to fit a distal end of an anchor engagement or anchor interface surface of the shaft, optionally allowing light to pass between the distal end of the anchor interface, to allow illumination and optical viewing of tissue and a surgical site by means of lighting and viewing functions. Extensions 26 can allow secure placement of anchor 22 at tissue, preventing movement in a backward direction after anchor 22 is pushed into the tissue. Anchor 22 can optionally include a light guide feature (25) at its tip to direct light from an end of a fiber optic cable, through anchor 22, to tissue being visualized.

Tool 14 can preferably be disposable after a single use but could be adapted to work with a reusable fiber optic imaging (i.e., "viewing") bundle and a fiber optic lighting bundle, each of which could be inserted into the shaft before a surgical procedure. The fiber lighting bundle and the fiber optic imaging bundles may each be reusable and constructed into a single element. Alternately, the fiber optic light bundle could be separate from the fiber optic imaging bundle. Preferably, the fiber optic light bundle could be disposable and affixed to or incorporated into the shaft. The imaging bundle could be separate and reusable, meaning that the imaging bundle would be protected from body fluid, such as by use of a lens at the distal end of the shaft to contain the imaging bundle within the shaft.

Figure 9:
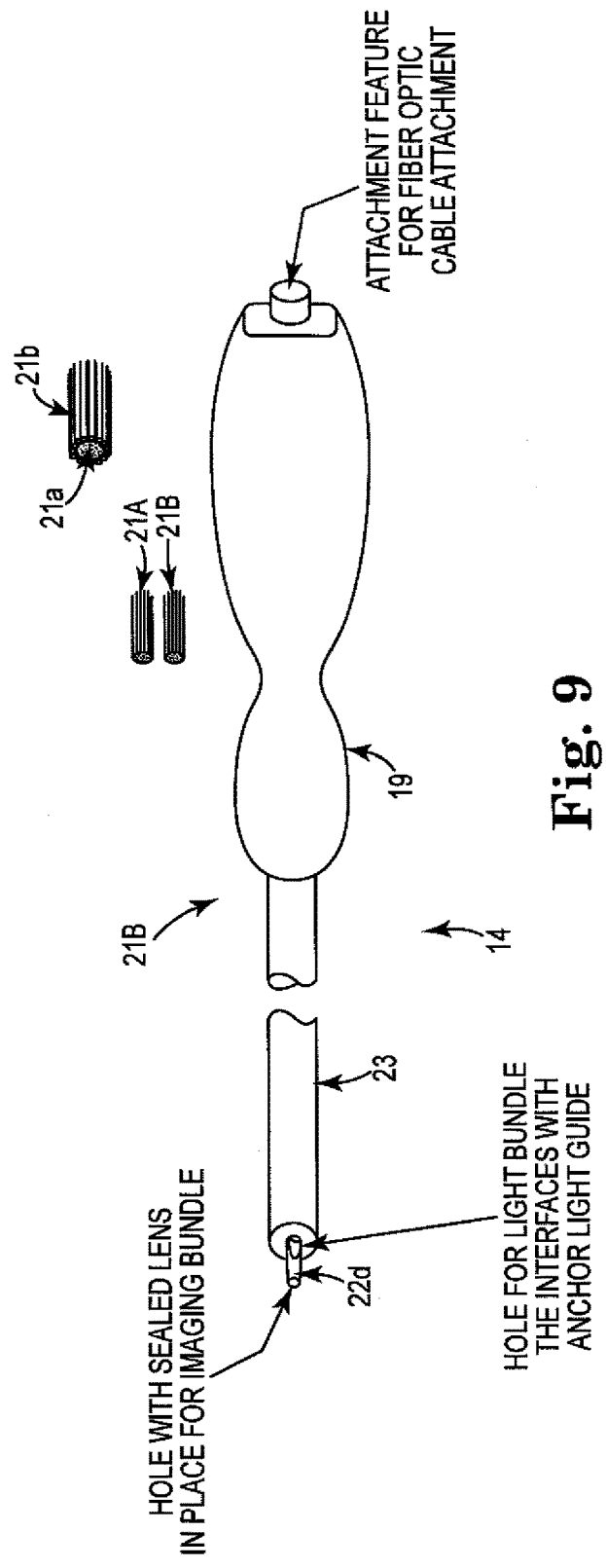

Referring to FIG. 9, tool 14 (of a system 20) can include lighting and viewing functions including one or more of a light, lens, working lumen, optical fibers (such as a light bundle 21b and imaging ("viewing") bundle 21a) extending between a proximal end (including a handle, toward an operator) and a distal end (toward a patient), a light source (not shown), and a camera or other visual recording device (not shown) at or connected to the proximal end. As illustrated, imaging fiber bundle 21b can include multiple fiber optic cables arranged as desired or useful, with one end (a distal end) of fiber optic cables being at a distal end of tool 14 and a second end (proximal end) being at a proximal end of tool 14. Imaging fiber bundle 21a can allow for viewing (visualization) of tissue illuminated by light function. In one arrangement, imaging bundle 21a and light bundle 21b are situated with imaging bundle 21a at a center, and light bundle 21b circumferentially surrounding imaging bundle 21a. In a different arrangement, imaging bundle 21a can be located along-side or otherwise separately from light bundle 21b. As such, the light source and light bundle (21b) can be generally divorced or separate from the imaging bundle 21a to allow for visualization of tissue structures without glare or illumination leakage into the imaging fiber bundle 21a. Optionally, imaging bundle 21a can be located internal to the shaft, within a lumen (not shown) with a sealed lens at the distal end to prevent imaging bundle 21a from contacting tissue or fluid of the patient during a surgical procedure and allowing for reuse of imaging bundle 21a.

Still referring to FIG. 9, at the distal end of the shaft is an anchor interface feature 22d for engaging channel or "needle interface" feature 22a of anchor 22 (not shown). Anchor interface feature 22d can communicate with one or both of imaging ("viewing") bundle 21a and light bundle 21b, to allow light and images to pass through tip 22, between tissue adjacent to tip 22 and each of imaging bundle 21a and light bundle 21b. Alternately, the shaft (i.e., "needle") may include both the light bundle 21b and imaging bundle 21a along the needle (through a lumen along the length of the needle), and an aperture or opening at a side or end of the needle can allow illumination and viewing. Viewing may be through a distal end lens or opening. Lighting may be through a side hole or distal end hole, through an aperture in the anchor 22 or by use of a translucent or transparent anchor 22.

Anchor interface feature 22d can optionally be at a distal end of a separate shaft structure located within the shaft (23) of tool 14, e.g., in a longitudinal lumen or channel. This allows the separate shaft structure that includes anchor interface feature 22b to be moveable within shaft 23 and extendable and retractable distally (by a mechanism located at the proximal end of tool 14) from the distal end of shaft 23. Optionally anchor interface 22d may include a detent or other mechanism to allow selective engagement and disengagement of an anchor, with extension and retraction distally, for placement in tissue.

Figure 10:
Figure 11:
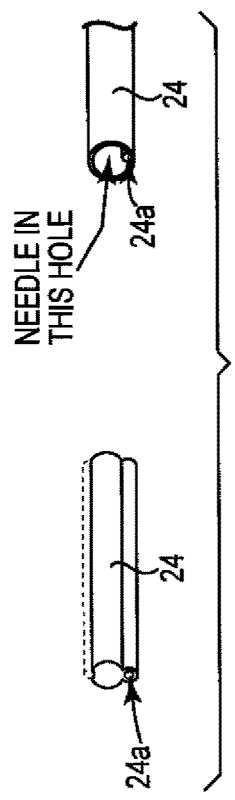
Figure 12:
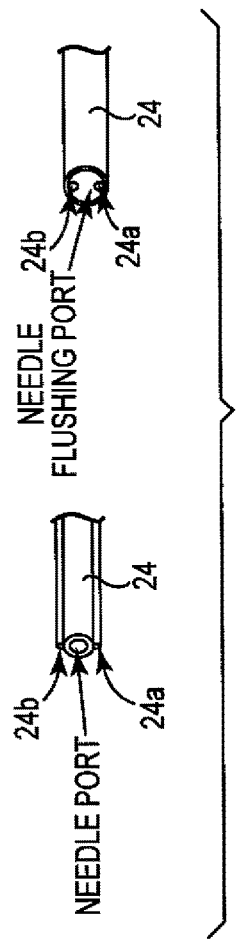

An optional sheath 24 can be included along an entire or distal length of shaft 23 to cover and secure a tissue anchor (22) until deployment from shaft 23, as shown in FIGS. 10-12. A sheath (24) can be a simple protective covering over a shaft (23) to retain and protect an anchor and allow fluid flushing (by use of the fluid delivery and optionally the suction functionality) to a tissue site for hydrodissection, or flushing of an optical (viewing) lens, or flushing of the anchor site to allow better visualization in the presence of blood, fat, or other tissue or fluids. Optionally or alternately, a sheath 24 may also include the lighting or imaging (viewing) functionality by including a one or more fiber optic cable for lighting or imaging (viewing). For example a sheath 24 may include a fiber optic lumen or other fiber optic containment feature to hold a fiber optic cable and direct light to the anchor or the tissue directly, or to allow imaging or viewing of tissue.

Also optionally or alternately, a sheath 24 can include other functions such as an irrigation port that can be used to irrigate a surgical site, to allow for hydrodissection, as well as better visualization by flushing the implantation site and lens for the fiber optic image bundle. In addition, a sheath 24 can take on various configurations with channels, ports, integrated fiber optic cables, tubes, and the like. See FIGS. 10, 11, and 12.

At FIG. 10, sheath 24 can be a simple polymeric rigid, flexible, or semi-rigid tube that fits over a shaft of tool 14, with two open ends. Such a sheath is described and illustrated at Applicant's copending U.S. Publication No. 2010/0274074, titled PELVIC FLOOR TREATMENTS AND RELATED TOOLS AND IMPLANTS, the entirety of which is incorporated herein by reference.

FIG. 11 shows sheath 24 similar to sheath 24 of FIG. 10 but additionally including a lumen 24a for a light fiber, alternately a light fiber 24a. As shown, the lumen or light fiber 24a may be external to shaft 24 (left illustration) or integral to the sidewall of shaft 24 (right illustration).

FIG. 12 shows sheath 24 similar to sheath 24 of FIG. 10 but additionally including a lumen 24a for a light fiber, alternately a light fiber 24a, and a lumen 24b for an imaging fiber, alternately imaging fiber 24b. As shown, each lumen or light fiber may be external to shaft 24 (left illustration) or integral to the sidewall of shaft 24 (right illustration).

Figure 13:
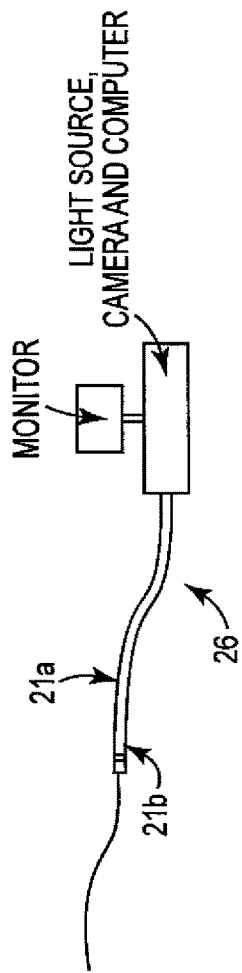
Figure 14:
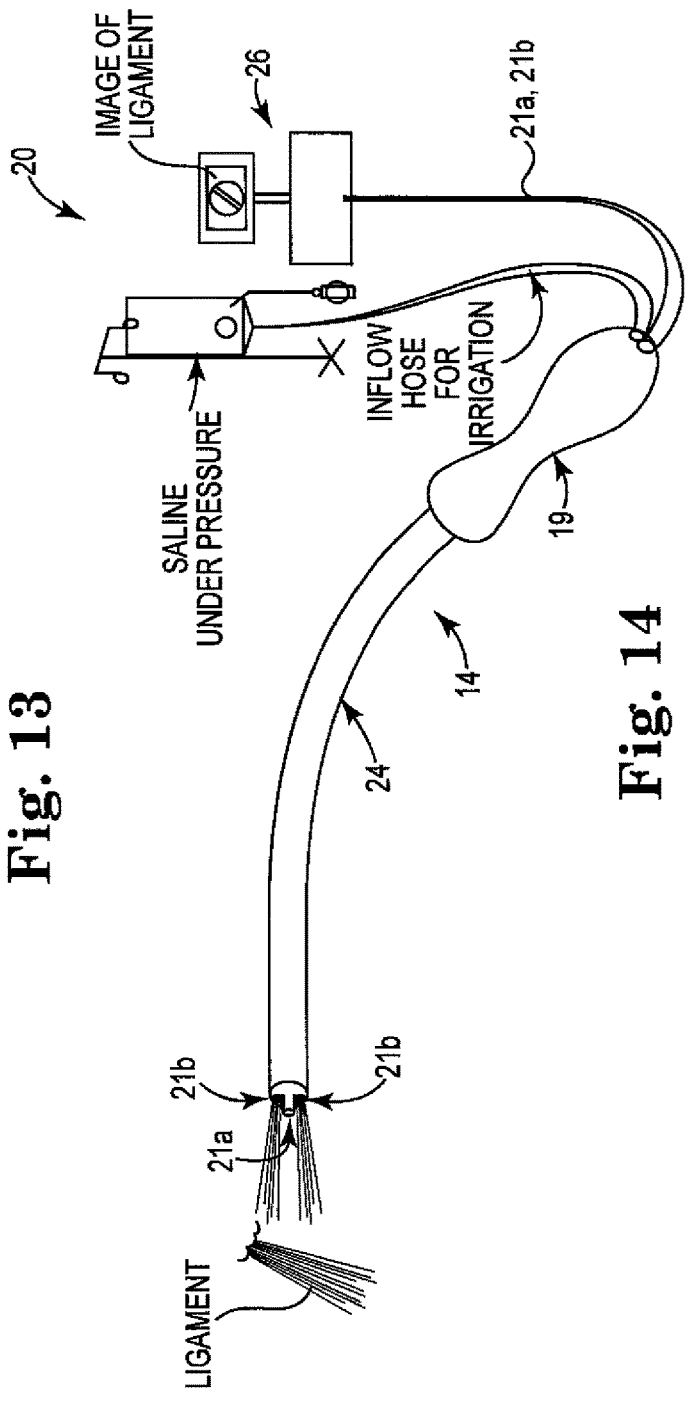

System 20 shown at FIGS. 13-14 can include an imaging system 26 having a light source, a camera, a monitor, a computer to process and store data, and imaging and light bundles (21a and 21b), interfacing with the needle system 20. As such, light can be emitted out of the anchor 22 (not shown) toward a target tissue (e.g., the pelvic ligament, muscle, fascia, sacrotuberous ligament, a location at a region of sacral anatomy, etc.). The distal end of the shaft, as illustrated, includes an optional inflow or suction port, a light port for light to illuminate tissue, an imaging port for viewing tissue, and an anchor interface that can engage an anchor such as a channel of a self-fixating tip. The anchor can be translucent or include a hole or aperture to allow light to pass from a light port (e.g., located at the shaft or the needle) to tissue. The anchor, shaft (needle), or another location at the distal end of tool 14 may include a lens that communicates with an imaging port to allow viewing of tissue at or near the anchor.

As shown in FIGS. 15-17, a custom or adapted sheath 24 can be provided with standard incontinence or prolapse repair needle systems to include necessary lumens (as part of sheath 24) to provide multi-functionality as described (e.g., central, imaging fiber lumen, and light fiber lumen). In this embodiment a tool 14 can include a shaft that could be a standard solid metal, rigid, needle 23 with a custom sheath that contains three lumens: a central lumen to contain the needle, an imaging fiber lumen to contain a fiber optic cable for imaging (viewing) a location of tissue, and a light fiber lumen to contain a fiber optic cable for illuminating a location of a tissue. The sheath 24 may be flexible (e.g., made of polyolefin such as polyethylene or polypropylene) and can conform to the shape of the needle. The needle can be malleable or rigid, optionally being bent to a desired shape by a surgeon during a procedure. The cost and ease of use and manufacture of an extruded multi-lumen sheath in, e.g., polyethylene, can be improved compared to other more complicated shaft constructions for a multi-functional tool. (Bending a multi-lumen shaft during manufacture may collapse an internal lumen.) An optic fiber cable for illumination or for viewing may be placed at an exterior surface of the polymeric sheath 24, at an interior surface of the polymeric sheath 24, or within a lumen or integral to a sidewall along the length of the polymeric sheath 24. A lens could be placed at the end of one or two or more fiber optic cables to allow a fiber (e.g., an imaging fiber) to be reusable by slipping the fiber into and out of the lumen of the sheath. Alternately, one or both of the imaging and light (illumination) fibers could be attached to the sheath and disposable along with the sheath. A needle tip extending through the (main) inner lumen of the sheath could include a distal end for engaging an anchor such as a self-fixating tip, or could include an aperture extending to a proximal end for a suture or an irrigation or suction channel or port.

Figure 18:
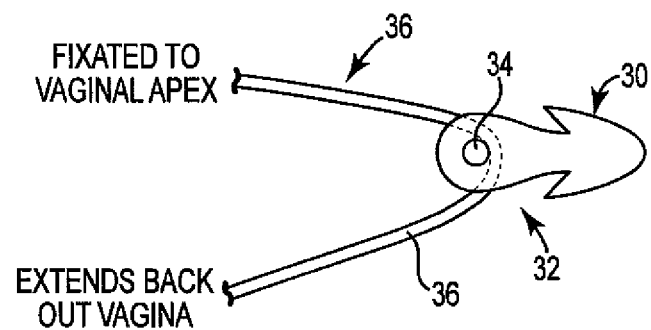
FIGS. 18-19 depict tensioning anchor configurations in accordance with embodiments of described inventions.
Figure 19:
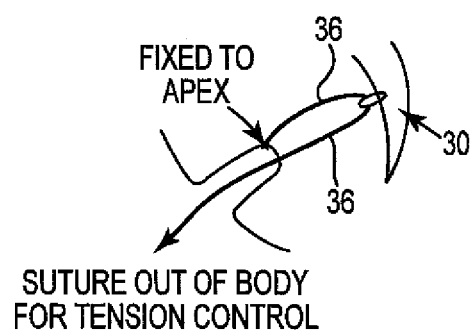

The embodiments of FIGS. 18-19 can include a tensioning or tensionable anchor 30 for use in a pelvic treatment such as a SCP procedure. Anchor 30 could take on various designs and configurations as known, disclosed, or incorporated herein. Specifically, a pulley system 32 that includes eyelet 34 (e.g., on anchor 30) and suture 36 can be used to provide tensioning or adjustment of the anchor 30 relative to an implant attached to suture 36, when anchor 30 is attached to the sacrum or another portion of the sacral anatomy. As such, the end of a suture 36 can be tied or attached through an implant to the vaginal apex while the rest of the suture is passed through eyelet 34 of anchor 30 and continue on to pass exterior to the body via the vagina. This allows for dynamic adjustment of the apical tension and support. Various known materials can be used to construct portions of this embodiment, including polypropylene, polycarbonate, polyethylene, suture materials, and the like.

Referring generally to FIGS. 20-24, various embodiments of surgical tool 50 having an elongate shaft and tube 52 are illustrated. Tool 50, including a shaft, is generally configured for use during a surgical procedure to facilitate guidance and passage of tube 52 to a surgical site or anatomy, e.g. a region of sacral anatomy. Tool 50 allows placement of tube 52 through an incision in a patient to allow tube 52 to provide access to an internal surgical location, such as for placement of a surgical implant. Tube 52 can be used to allow surgical items such as tools, sutures, implants or components thereof, or other objects (e.g., sharp objects) to be passed (through tube 52), to an internal surgical site without having to make multiple attempts from the incision to the anatomical target area. Optionally, surgical tool 50, tube 52, or both, can include a function for illuminating or viewing a surgical site, for dissection, for irrigation, for placing an anchor, and the like, as described herein for multi-functional tools. For example, if a component of surgical tool 50, tube 52, or both, is of a plastic or polymeric light-conductive material, light can be transmitted through that material from a proximal end to a distal end at the surgical site.

Tool 50 includes handle 58 on a proximal end, an elongate shaft extending from the handle to a distal end, and elongate tube 52 associated with the elongate shaft. Generally, the "tube" can be a hollow elongate structure such as a rigid or flexible cannula, retractor, expansion member, or similar structure that includes an open channel hollow interior, and that when placed within a patient allows access between an exterior of a patient and a pelvic region during surgery.

In certain embodiments tube 52 can be useful for accessing a male or female pelvic anatomy, especially a female pelvic anatomy, transvaginally, to access tissue of the posterior pelvic region such as to perform an SCP procedure. Tube 52 can have a length to allow such access when the tube is placed transvaginally, e.g., a length to allow a distal end of the tube to access pelvic tissue while a proximal end of the tube extends through a vaginal opening to a location external to the patient. The proximal end of the tube remains external to the patient during use to allow a surgeon or other user to access and manipulate the proximal end and access a surgical site through the tube at the distal end. Exemplary lengths between a proximal and a distal end may be in the range from 13 to 18 centimeters, especially for use in a female patient to transvaginally access a posterior location of a pelvic region such as a region of sacral anatomy.

The diameter of the elongate shaft and tube portion of the tool can be useful to allow the tool to be inserted and placed with reduced trauma. Optionally, as described elsewhere herein, a diameter of the tube can be variable, such as by being expandable after placement of the tube within a patient, to allow increased and expanded access to tissue at a surgical site.

Optionally the tool, at the tool distal end, either at the distal end of the tube or the distal end of the shaft, can include one or more functional features (e.g., as described previously herein to be useful for the surgical tool 14) including one or more features that allow tool 50 or tube 52 to be useful to carry out functions such as dissection (a mechanical dissection using a sharp blade, or hydrodissection), blunt dissection, viewing (visualization) of a surgical location, illumination of a surgical location, fluid delivery at a surgical location, irrigation at a surgical location, suction at a surgical location, steerability of the distal end of the shaft or the tube or both, and placing anchors (bone anchors, soft tissue anchors such as a self-fixating tip, sutures, etc.) into a desired target tissue at a surgical location.

The various systems, apparatus, and methods detailed herein are envisioned for use with many known implant and repair systems (e.g., for male and female), features and methods, including those disclosed in U.S. Pat. Nos. 7,500, 945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010-0174134, 2010-0298630, and 2002/147382. Accordingly, the above-identified disclosures are fully incorporated herein by reference in their entirety.

Figure 20:
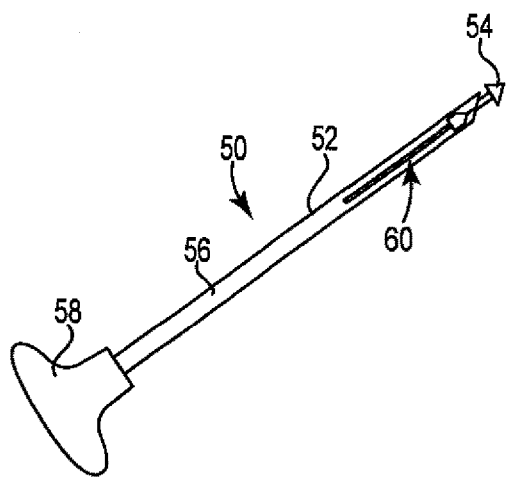
FIGS. 20 through 23 depict surgical tools and expansion members in accordance with embodiments of described inventions.

FIG. 20 shows a single example of a tool useful for placing a "tube" 52 for accessing a surgical location at a pelvic region. Tool 50 at FIG. 20 can include a leading distal end 54, a shaft 56 (e.g., inside of tube 52), tube 52 (e.g., located at an exterior of shaft 56), and handle 58. Further, a spring, spring-activated, mechanically activated, or other type of cutting mechanism 60 can be included anywhere along the tool 50 to facilitate cutting (for dissection) and/or to activate the distal end 54 to create a small incision in the anatomy of the patient. Upon cutting and guiding tool 50 through a tissue path (e.g., transvaginally in a female patient) to a target area of tissue, the tube 52 can be separated from shaft 56. Handle 58 and shaft 56 can be removed from the patient and tube 52 left behind (i.e., can remain in place during a surgical placement procedure) to provide a defined pathway or channel to the surgical area (site), for access to the surgical area (site). In particular methods of SCP treatment of a female anatomy, transvaginally, tube 52 becomes placed with a proximal end extending out of the patient's vaginal introitus, the tube extending through the vagina and a vaginal incision, and a distal end become located at a posterior of the patient's pelvic region, e.g., proximal to a region of sacral anatomy.

Figure 21:
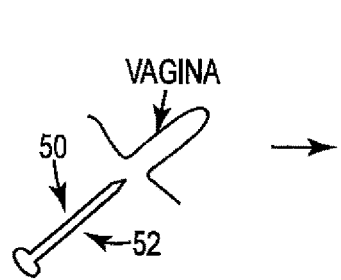
Figure 22:
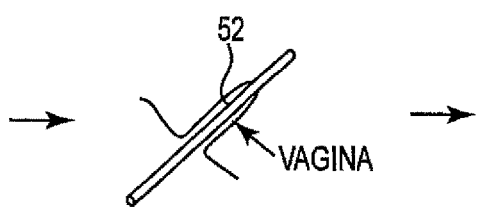
Figure 23:
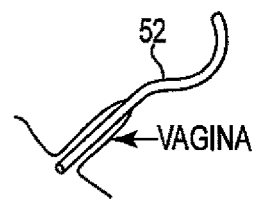

As shown in FIGS. 21, 22, and 23, tool 50 including tube 52 can take on a number of different shape and size configurations and can be advance through the vagina and a vaginal incision and into the posterior of a pelvic region, near a sacrum, via dissection. Tool 50 and tube 52 can be used to provide a pathway or port access to various other anatomical structures or sites without deviating from the spirit and scope of the present invention.

The tool 50 and tube 52, or portions or components thereof, can be constructed of any known or compatible materials, including polymers or metals. Tool 50 and tube 52, their various components, structures, features, materials and methods may have a number of suitable configurations as shown and described in the previously-incorporated references.

Alternate embodiments of devices useful in a manner similar to tube 54 (e.g., "expansion members," "retractors," or "tubes") are also contemplated for use in providing access to internal tissue of a pelvic region through an incision in a male or female patient, e.g., as a tissue retractor used to gain transvaginal access to a posterior region of a female pelvic anatomy. Any of these tube 54 and the rest may be useful according to one or more of the methods described herein for placing an implant to support pelvic tissue, for example a SCP procedure, using any one or more of the herein-described implants, insertions tools, multi-functional tools, anchors, etc.

Various such embodiments of "expansion members" are described hereinbelow, and may have general structural and operational features that allow one or more flexible, rigid, or semi-rigid, distal retracting structures to be introduced through an incision (e.g., a vaginal incision) in a closed, compressed, or reduced-size or reduced-diameter state, then the moved, assembled, or expanded to enlarge a cross-sectional size or related space or opening to push tissue aside to create space in and access to a pelvic region with access to desired pelvic anatomy. A preferred size of a device can include a cross sectional dimension (e.g., a width or diameter associated with an opening along a length of the device) in the range from 1 to 5 centimeters, such as from 2 to 4 centimeters (these are referred to herein as diameter ranges $d_1$), when distal retracting structures are in their the reduced-size configuration. Upon opening, un-compressing, expanding, or assembling, etc., the distal retracting structures, a preferred dimension (e.g., a width or diameter associated with an opening along a length of the device) associated with these structures can be in the range from 2 to 10 centimeters, such as from 3 to 7 centimeters (these are referred to herein as diameter ranges $d_2$). Also generally, these structures (tubes, retractors, and the like) can include desired length dimensions (from a proximal to a distal end) that can be selected to work with a particular anatomy (male or female) and procedure (anterior repair, posterior repair, etc.). A length of a specific structure (tube, retractor, etc.) useful in a transvaginal method of treating a posterior pelvic condition (e.g., a SCP procedure) can be sufficient to allow the distal end to reach a region of a sacral anatomy as a proximal end remains at or outside of the vaginal introitus. A related dimension is the "working depth" of such a device, which is the distance between the distal end of the device and the vaginal introitus, when installed, and which can be any dimension useful or desired, e.g., from 13 to 18 centimeters. A distance by which the device extends proximally, away from a patient, out of the vaginal introitus, is preferably minimized. Still referring to the use of these devices in transvaginal methods of treatment, another relevant dimension is a "working space" dimension, which is a lateral dimension of an opening at a proximal end of the device, such as a diameter, which may preferably be in a range from 3 to 8 centimeters; in a transvaginal method, this is an approximate diameter of a vaginal introitus held open by a proximal end of the device.

FIGS. 24A-24D illustrate a pressurized tube expansion member and technique in accordance with embodiments of the present invention. These figures illustrate a specific embodiment of a retractor type of an expandable "tube" (100) and a separate inserter device (distractor) in the form of a shaft (104) that can be placed within tube 100 to assist placing the tube in a male or female patient. The shaft-and-tube configuration can be used to allow the tube to be expanded within the patient, producing a channel through the tube to allow access to the interior anatomy of the patient, such as at a pelvic region. The pressurized tube concept uses pressure created by a syringe or other means to expand a small elastic tube (similar to a catheter deployment system, but larger). Due to the flexibility of the elastic tube, the outer tube ca be inserted via a rigid member (e.g., tube, rod, introducer device, or other relatively rigid inserter device capable of opening a vaginal canal) and then expanded before or after the rigid member has been extracted. After expansion of the tube, another rigid replacement tube could be placed over the expanded tube to provide open working space to pelvic anatomy such as the sacrum, and the expanded tube can be removed. The tube can be designed to provide a working depth and a working space as described herein.

Referring to FIG. 24A, expandable tube 100 includes distal end 102 and proximal end 106. Expandable tube 100 also includes an opening at each of the proximal and distal ends, and a continuous channel or opening extending between the proximal and distal ends. The structure of the tube, i.e., the tube sidewalls, include a single space or multiple spaces that form an interior space of one or more balloon or bladder adapted so that the interior space (not shown) that can be filled with fluid to cause tube 100 to expand in a manner to increase the diameter of the tube and the size of the openings at the distal end proximal ends. FIGS. 24A and 24B show the tube in a relaxed, collapsed (reduced diameter) state. The diameter of the tube in this collapsed state can be as desired, generally a diameter that allows efficient (e.g., with reduced patient trauma) placement of the collapsed tube within a patient by use of a shaft 104. A preferred diameter can be in the range from 1 to 5 centimeters, such as from 2 to 4 centimeters (these are referred to herein as diameter ranges $d_1$). This diameter is approximately equal to the outer diameter of shaft 104.

Still referring to FIG. 24A, an insertion tool 104 can be used to place tube 100 within a patient for a surgical procedure. The tool 104 can include an elongate flexible, rigid, semi-rigid, or malleable shaft, needle, or rod, 104 ("shaft" 104) to support tube 100. In use, with tube 100 placed at the exterior surface of shaft 104, distal end 102 can be inserted into a patient (e.g., transvaginally into a female patient), while tube 100 is in a collapsed, non-inflated condition, to cause distal end 102 to become located at a desired tissue location such as at or near a region of sacral anatomy. Before or after removing shaft 104, a pressurized fluid (e.g., liquid or gas such as water, saline, or air) can be introduced into interior space of tube 100 to fill and pressurize the space. In the collapsed state, tube 100 may optionally include wrinkles or folds that will become unwrinkled or unfolded as tube 100 is expanded to the expanded state. Alternately, tube 100 may be an elastic material that stretches to transition between the collapsed and expanded states.

Fluid may be introduced to the interior space by any useful method and means, such as by use of a syringe 108 at port 110 at proximal end 106. The introduction of fluid will inflate the tube to an expanded state as shown at FIGS. 24C and 24D, having an expanded diameter that can be any desired diameter, such as a diameter in the range from 2 to 10 centimeters, such as from 3 to 7 centimeters (these are referred to herein as diameter ranges $d_2$).

Tube 100, inflated, has strength and lateral and longitudinal rigidity that is sufficient for tube 100 to be capable of creating an opening in tissue in a pelvic region by expanding the tissue, e.g., when placed transvaginally. If desired, optional mechanical reinforcement may be included along a length or circumference of tube 100. In use in a transvaginal procedure such as an SCP (optionally in conjunction with a tool, multi-functional tool, implant, adjustable implant, anchor, or other device or method described herein), tube 100 is inserted into a vagina using shaft 104 and distal end 102 is placed near a sacrum. The patient's tissue will collapse around tube 100. Tube 100 is then pressurized to force the tissue to expand around an increasing-diameter tube 100 and open to create access to the posterior of the pelvic region, e.g., to gain access to a region of sacral anatomy. Optionally, after tube 100 is expanded within the patient, another tube (e.g., a tube or retractor or expansion member as described herein, and providing a working depth and a working space as described), e.g., having greater mechanical strength, could be placed over the expanded tube within the patient to provide open access to pelvic anatomy such as a region of sacral anatomy, and the expanded tube 100 can be removed.

Many other embodiments of tubes such as tubes 100 can be useful and used as described, but with different structures and features of the tube. Examples of such other embodiments are described herein and are illustrated, e.g., at FIGS. 25 through 39 and 101 through 110. Any of these illustrated and described devices (referred to interchangeably as "expansion members," "tubes," or "retractors") can be used and useful by a method of inserting the device into a surgical incision, for example a transvaginal incision, and expanding tissue to provide access to desired anatomy. For performing an SCP or other transvaginal procedure, a tube or retractor can be placed transvaginally, e.g., in a non-expanded, collapsed state. The structure can then be expanded (optionally by assembly) while in place transvaginally, to create access to desired anatomy such as the posterior of a pelvic region, e.g., to gain access to a region of sacral anatomy. A surgeon can perform a surgical procedure by use of the access, which provides working space to pelvic anatomy such as the sacrum. The method can optionally also involve a tool, multi-functional tool, implant, adjustable implant, anchor, or other device or method described herein. Optional features and structures (e.g., fiber optics) to allow viewing or illumination at the distal end can be incorporated into any of these types of devices. For example, if a structural component of the device is made of a plastic or polymeric light-conductive material, light can be transmitted through that material from a proximal end to a distal end at the surgical site. Alternately, a fiber optic cable can be incorporated into a length of the device, extending from a proximal to or toward a distal end, to allow light to be transmitted from the proximal end to the distal end, or to allow images to be transmitted from the distal end to the proximal end. Light could alternately be generated and shone from the distal end.

Referring to FIGS. 25A-25F, a self-expanding nitinol stent 120, deployment tube (e.g., catheter) 122, and hand operated retractor device 124, and, technique in accordance with embodiments of the present invention are shown. The self-expanding (e.g., nitinol) stent can use the self-expanding (expandable) strength of nitinol or a like metal or polymeric material. Stent 120 is biased to an open (non-collapsed, or "deployed" state), which has a reduced length and increased diameter ($d_2$), and can be collapsed and extended to a non-deployed state having a greater length and reduced diameter ($d_1$). The non-collapsed (deployed) stent can be collapsed (closed) and lengthened by placing lateral pressure on the stent surface, e.g., at an end or a location along the length of the stent. A stent for use with the methods described herein can be set (biased) to be expanded, and would self-expand when the deployment tube (122) was removed from the outer diameter and outer surface. The stent can be designed to provide a working depth and a working space as described herein.

In use, the collapsed stent 120, located within the deployment tube 122 (see FIG. 25A) can be placed in a patient, e.g., transvaginally, with the distal end located near a desired region of anatomy such as a region of sacral anatomy. Deployment tube 122 can be removed and stent 120 expands to an expanded diameter (e.g., $d_2$), within the patient, creating a opening within the interior of expanded stent 120 between a proximal end a distal end of stent 120, e.g., between a vaginal introitus and a region of sacral anatomy. The length-wise opening allows access for a surgical procedure. Stent 120 has strength and lateral and longitudinal rigidity that allow the tube to expand to create an opening in tissue in a pelvic region by expanding the tissue. A surgical procedure (e.g., SCP) can be performed by accessing pelvic anatomy through space (channel or opening) created by the expanded stent. After the procedure, the stent can be removed, optionally collapsed and then removed.

Optionally stent 120 may be collapsed by re-inserting the stent into deployment tube 122, at the proximal end (outside of the patient). Deployment tube 122 could be placed at the proximal end and advanced distally along the length of stent 120, causing stent 120 to collapse. Optionally stent 120 can include strings (e.g., sutures or the like) 124 that can be attached to stent 120, e.g., at a proximal end. Optionally, to re-insert stent 120 into deployment tube 122, strings 124 can be pulled in the proximal direction (away from the patient) while deployment tube 122 is advanced in the distal direction (toward the patient). This combination of steps can efficiently allow for retraction/compression of stent 120 back into the original deployment tube 122.

Another optional device useful to manually expand and contract stent 120 can be a "hand operated retractor" 128 that fits around an end of stent 120 to place pressure on the end of the stent. This hand operated retraction can include jaw to contact an end of stent 120, a hand grip to control the size of the jaws, and a quick connector that can lock the hand operated retractor at any position. See FIGS. 25E and 25F.

FIGS. 26A and 26B show an expandable stent 140, and techniques in accordance with embodiments of the present invention is shown. The expandable stent 140 is similar in size and strength to stent 120 of FIGS. 25A-25F. Optionally, stent 140 includes a shape-memory feature. For example stent 140 can be stable (non-biased), and can exist before use in a non-deployed (collapsed) state, e.g., at a diameter $d_1$. A deployment means such as an expandable catheter, deployment tube, or similar construction (not shown), can be placed within the interior of stent 140 and used to place stent 140 at a desired anatomical location, e.g., transvaginally. The deployment means can then expand within stent 140, causing stent 140 to expand to the expanded state within the patient. The deployment means can then compress and be removed to leave the stent in the desired expanded state. An alternative mode of expansion could be a tapered object or introducer passed from the proximal end to the distal end after stent 140 is located as desired within the patient. The shape-memory character allows stent 140 to adapt and maintain an expanded diameter (e.g., $d_2$), within the patient, creating a space within the interior of expanded stent 140, e.g., between a vaginal introitus and a region of sacral anatomy. The space allows access for a surgical procedure. Stent 140 has strength, lateral and longitudinal rigidity, and a shape memory property that allow the to expansion within a patient to create an opening in tissue in a pelvic region by expanding the tissue, and holding the tissue in the expanded condition.

Referring to FIG. 27, a malleable retraction system device and technique in accordance with embodiments of the present invention are shown. The malleable retraction system can be adapted to a frame of various different existing retraction system device such as those used in vaginal surgeries (e.g., the Lone Star retractor system). The new device would involve one or more malleable retractor arms 152 that attach directly to retractor frame 150 and extend into a surgical incision such as a vaginal incision to create access to desired anatomy such as an anchor location. The retractor system with malleable retractor arms can be designed to provide a diameter $d_2$, a working depth, and a working space as described herein.

Still referring to FIG. 27, during use, frame 150 can be placed to allow access to a vaginal introitus, and external to the patient. One or more refractor arms 152 can be connected to frame 150 and introduced through the vaginal introitus, optionally through a vaginal incision, then moved into location to allow access to a region of posterior pelvic anatomy such as a region of a sacral anatomy. Each arm can be malleable, and optionally additionally or alternatively flexible and capable of locking into a rigid position. In use in a transvaginal procedure such as an SCP, retractor arms 152 are inserted into a vagina and distal ends are placed at a posterior location such as near a sacrum. The patient's tissue can be moved and expanded to create access to the posterior of the pelvic region, e.g., to gain access to a region of sacral anatomy. Once retractor arms 152 have been placed to access anatomy as desired, the malleable or flexible arms could be locked rigidly into position. A surgeon could perform a desired surgical procedure, after which frame 150 and retractor arms 152 are removed.

Referring to FIGS. 28A, 28B, and 28C, a forced expansion blind device and technique in accordance with embodiments of the present invention are shown. The forced expansion blind includes a rolled, flexible or malleable expandable tube 158, and a mechanical method to expand the rolled piece of material from a collapsed expandable tube 158, into an expanded tube that provides access to a surgical site. Referring still to FIGS. 28A, 28B, and 28C, expandable tube 158 is removably engaged at an end of syringe 162, having plunger 160 that can move (slide) within a cylinder of syringe 162. The end of plunger 160 is shaped to mechanically deform the rolled piece of material (tube 158, in a collapsed state as shown at FIG. 28A) to a new expanded (non-collapsed) size and shape, by extending the tip of the plunger out of the syringe cylinder and distally into the rolled piece. Once completed, the tip of the plunger is drawn back within the hollow rigid tube leaving the expanded tube 158 (see FIG. 28C) in place for a surgical procedure. The expandable tube 158 can be designed to provide a working depth and a working space as described herein.

In use, collapsed tube 158 (FIG. 28B) located at the end of syringe 162 can be placed in a patient, e.g., transvaginally, with the distal end located near a desired region of anatomy such as a region of sacral anatomy. Plunger 160 can be advanced out the distal end of the syringe cylinder and into collapsed tube 158 (diameter $d_1$), to cause collapsed tube 158 to be expanded to an expanded diameter (e.g., $d_2$), within the patient, and creating a space within the interior of expanded tube 158, e.g., between a vaginal introitus and a region of sacral anatomy. The space allows access for the surgical procedure. Expanded tube 158 (see FIG. 28C) has strength and lateral and longitudinal rigidity that allow the tube to expand to create an opening in tissue in a pelvic region by expanding the tissue.

Referring to FIGS. 29A-29D, a retractor system and technique in accordance with embodiments of the present invention are shown. This system uses a parallel system that moves one retractor arm (168) in relation to the other, along a rack, which may ratchet or otherwise allow selective movement and a secure positional relation between arms 168. By expanding and manipulating the system 166, the retractor arms are moved closer together or farther apart, allowing the retractor arms to create space in a pelvic region for access to desired anatomy. The retractor system can be designed to provide a working depth and a working space as described herein.

Referring to FIGS. 29A, 29B, 29C, and 29D, a retraction device and technique in accordance with embodiments of the present invention are shown. The retractor system 170 can include a frame made of retractor members 172 and rack members 174. Retractor members 172 are selectively moveable along rack members 174, and can engage rack members 174 to prevent movement after placement as desired, to retract tissue using retractor arms 168. Retractor members include a proximal end that rides or otherwise engages rack members 174, and additionally include retractor arms 176. Optionally and as illustrated, retractor arms 168 are curved away from each other at their distal ends, to improve tissue separation by use of retractor arms 168.

During use, the frame comprising rack members 174 and retractor members 172 are placed at a vaginal opening, to frame and allow access to a vaginal introitus. One or more opposing retractor arms 168 connected to opposing retractor members 150 can be introduced into the vagina, through the vaginal introitus and vaginal incision, then moved so a distal end of each retractor arm is located adjacent to a desired region of posterior pelvic anatomy such as a region of a sacral anatomy. Each arm can be rigid or malleable, and optionally additionally or alternatively flexible and capable of locking into position. In use in a transvaginal procedure such as an SCP, retractor arms 168 are inserted into a vagina (180) and distal ends are placed at a posterior location such as near a sacrum. See FIG. 29D. Movement of refractor members 172 along lengths of opposing rack members 174 allows the distal end of retractor arms 168 to move a patient's pelvic tissue and expand the pelvic tissue to create access to the posterior of the pelvic region, e.g., to gain access to a region of sacral anatomy. Once arms 168 have been placed to access anatomy as desired, the retractor members 172 can be locked into position along the lengths of rack members 174. A surgeon could perform a desired surgical procedure, after which refractor system 170 can be removed.

Figure 30A:
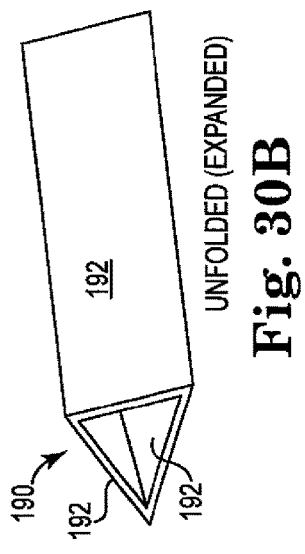
FIGS. 30A-30E depict an expansion device and technique in accordance with embodiments of described inventions.
Figure 30B:
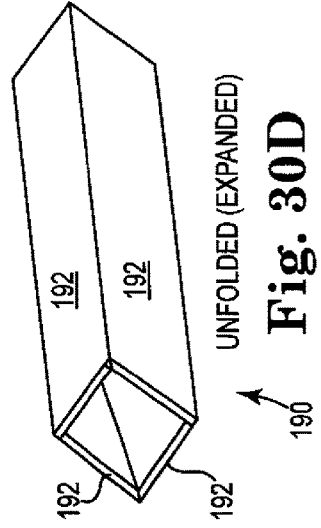
Figure 30C:
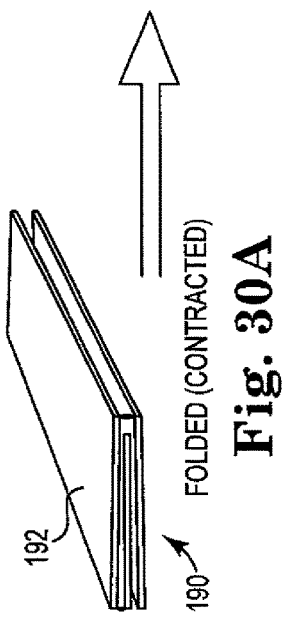
Figure 30D:
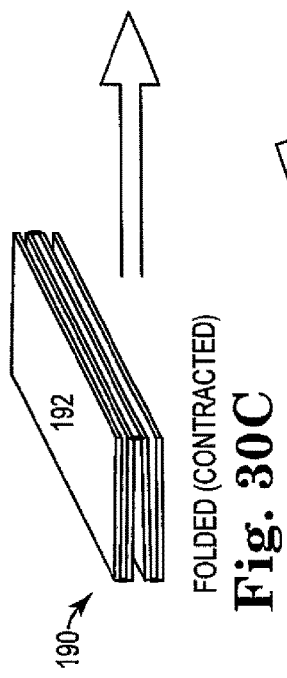
Figure 30E:
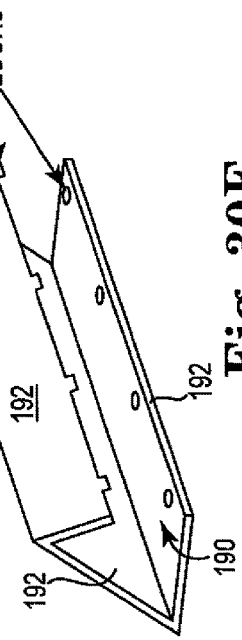

Referring to FIGS. 30A-30E, expansion members 190 comprising multiple folding side members 192, and technique in accordance with embodiments of the present invention are shown. Each expansion member 190 includes side members 192 that can be folded to a reduced cross sectional profile (size of an opening), in a folded configuration, as shown at FIGS. 30A and 30C. The folded side members can be unfolded and optionally assembled to open (expand) the expansion member to an unfolded (expanded, opened) configuration as shown at FIGS. 30B and 30D. The two variations shown in the figures create a multi-sided (unfolded) shape from a single two-dimensional (folded) part. The two-dimensional folded part contains several small members (side members) that can be unfolded and assembled to create a three dimensional shape having an opening between a distal end and a proximal end that provides access (in the form of a tunnel, channel, or other opening) for access and visualization of a surgical site. The cross sectional size of the expansion member in the unfolded configuration can include a dimension $d_2$, working depth, and working space as described herein. As shown at FIG. 30E, any useful form of a locking, closing, assembly, or securing mechanism can be included as desired to maintain the strength and rigidity of an unfolded (opened) expansion member 190. Expansion members 190 as illustrated include 3 and 4 folding side members 192, more may be included, such as 5, 6, 7, 8, or more, as desired, to produce different folding geometries and folded and unfolded sizes and shapes.

An expansion member 190 can be used as generally described elsewhere herein, to perform a pelvic surgical procedure such as a SCP or other pelvic procedure; e.g., by insertion vaginally in a folded configuration, opening the expansion member 190 to an unfolded configuration to produce access into a posterior pelvic location, performing the surgical procedure, then removing expansion member 190, optionally by folding before removal. The method can be performed optionally in conjunction with any one or more of a tool, multi-functional tool, implant, adjustable implant, anchor, or other device or method described herein.

Referring to FIG. 31, illustrated is an embodiment of an expansion member that includes rotating iris/wedge side members, and techniques, in accordance with embodiments of the present invention. The rotating Iris/Wedge side member device involves an expansion mechanism similar to a camera iris that manipulates (rotates) multiple triangular side members assembled in a circumference for separate rotation, to expand or contract an object (e.g., surgical opening). In this example embodiment there are 4 small triangular objects (side members) that rotate separately, one-by-one, as desired to open up and expand a surgical opening or incision to a desired size.

Still referring to FIG. 31, expansion member 200 comprising multiple (four, as illustrated) rotating side members 202, and technique in accordance with embodiments of the present invention are shown. Expansion member 200 includes triangular (cross section) side members 202 that can be rotated separately or together to a reduced or increase a cross sectional profile (e.g., inner or outer diameter) of expansion member 200, creating a variable-sized interior channel (opening) extending from a proximal end to a distal end. Two optional frames 204 (circular as illustrated) can be located one each at the proximal end and the distal end of expansion member 200 to hold rotating side members 202 in place relative to each other and allow their separate or collective rotation. In a folded configuration expansion members 200 are rotated to place tips 206 of each triangular side member 202 toward the interior location of expansion member 200. The folded side members can be rotated, separately or together, to increase the effective cross-sectional size (e.g., outer diameter) of expansion member 200 to an unfolded configuration; this also opens the interior channel. The cross sectional size of expansion member 200 in the unfolded configuration can include a dimension $d_2$, working depth, and working space as described herein. Rotating side members 206 are illustrated to be triangular in cross section, but other useful shapes can be used instead, such as multiple rotatable blade side members (204) having a straight cross section. See FIGS. 31B and 31C shown a closed and open configuration (respectively) of such an embodiment.

An expansion member 200 can be used as generally described elsewhere herein, to perform a pelvic surgical procedure such as a SCP or other pelvic procedure; e.g., by insertion vaginally in a folded configuration, selectively rotating one or more expansion member 202 to produce an unfolded configuration that creates access into a posterior pelvic location, performing the surgical procedure, then removing expansion member 200, optionally by folding before removal. The method can be performed optionally in conjunction with any one or more of a tool, multi-functional tool, implant, adjustable implant, anchor, or other device or method described herein.

Referring to FIGS. 32A and 32B, an expansion member in the form of a coil member and technique in accordance with embodiments of the present invention are shown. The coil member 210 (a form of an expansion member) can use a flat sheet of rigid metal (e.g., steel), plastic, or like material that is shape set to a small diameter (e.g., $d_1$) then can be expanded to a larger diameter (e.g., $d_2$) by moving a cam, by passing rings down the inside diameter of the tube, or by another mechanical expansion mechanism. The initial (closed, none-expanded) shape is similar to a spindled cone and the final (open, expanded) shape is closer to a cylinder.

Still referring to FIG. 32A, expansion member (coil member 210) is wound to form a funnel having a proximal end 214 and a distal end 216. A distal end of cam 212 engages an edge or surface of the wound funnel, to allow the funnel to be opened and closed by distal and proximal movement of cam 212 (see arrows "A"). FIG. 32B shows coil member 210 before being wound to form a funnel, and with the distal end of cam 212 not being secured yet to a surface or edge of the wound funnel. As shown, distal end 216 may exhibit a relatively smaller diameter than proximal end 214, during insertion and after expansion. The cross sectional size of expansion member 210 in the expanded configuration can include a dimension $d_2$, working depth, and working space as described herein.

An expansion member 210 can be used as generally described elsewhere herein, to perform a pelvic surgical procedure such as a SCP or other pelvic procedure; e.g., by insertion vaginally in a coiled (un-expanded) configuration such as a funnel form, selectively moving cam 12 to expand the funnel in a manner to create access into a posterior pelvic location, performing the surgical procedure, then removing expansion member 210, optionally by reducing the size of expansion member 210 by reverse movement of cam 12 before removal.

In an alternate embodiment, one or more rigid dilation rings 218 of various diameters can be used as an alternative to cam 212, to expand expansion member 210. Specifically, after placing expansion member 210 in a patient (e.g., vaginally) one or multiple dilation rings 218 can be inserted into proximal end 214 and advanced distally toward distal end 216, the rigid dilation ring will cause expansion member 210 to expand to a desired size.

Referring to FIGS. 33A-33F, an insertable member (a form of expandable member) and technique in accordance with embodiments of the invention are shown. The insertable member comprises side members of different lengths, as illustrated: one long side member and two smaller side members, to create a region of visibility at the distal end of the insertable member. The main long side member piece would be placed to extend the entire length between a vaginal introitus and a sacrum. The one or more (two as illustrated) small side member pieces would be of to a (shorter) length to extend into a vagina and part of the distance to the sacrum, such as to or through a vaginal incision or vaginal apex or cuff. The insertion member may be capable of expanding from a collapsed or folded size and diameter to an expanded or un-folded diameter by any useful structure and means. For example, a small ratcheting feature along the two smaller side member pieces would allow these to expand and control the size (diameter) of a surgical incision or surgical opening.

FIGS. 33A-33F show expansion member 220 comprising multiple side members 222 (short members) and 224 (long member), and technique in accordance with embodiments of the present invention. Expansion member 220 includes two short side members 222 attached to long side member 224, in a configuration for short side members 222 to reach between a vaginal introitus and approximately a vaginal cuff or vaginal incision. Long member 224 extends from proximal end 226 of expansion member 220, through a vagina such that distal end 228 reaches a location in a pelvic region near a region of sacral anatomy. The side members can adapt either of a non-expanded configuration (see FIG. 33C) and an expanded configuration (FIG. 33E) having diameters $d_1$ and $d_2$ (respectively) as described herein. Between each side member are joints 230 that can be expanded and contracted to selectively increase (and decrease) the space (distance) between the side members to expand and contract the overall cross sectional size of expansion member 220 and an opening defined thereby. Spaces between side members can be controlled by joints 230, which can be controlled by any desired and useful mechanical or electronic means, such as by a screw-type control, an electronic control, a cam, a smooth one-way or two-way engagement, or a ratcheting or locking one-way or two-way engagement. The cross sectional size of expansion member 220 in the expanded configuration can include a dimension $d_2$, working depth (measured by a length of long side member 224), and working space as described herein.

An expansion member 220 can be used as generally described elsewhere herein to perform a pelvic surgical procedure such as a SCP or other pelvic procedure, e.g., by insertion vaginally in a non-expanded configuration, selectively expanding expansion member 220 by expanding joints 230 separately or at once, performing the surgical procedure (which may involve one or more of: an implant, adjustable implant, anchor, tool, or multi-functional tool, or implantation method as described herein), then removing expansion member 220, optionally by reducing the size of expansion member 220 by reverse movement of joints 230 before removal.

Referring to FIGS. 34A-34J, retractor systems and techniques in accordance with embodiments of the present invention are shown.

At FIGS. 34A, 34B, and 34C, a retractor 240 is illustrated, comprising a wound rigid metal or plastic sheet, that can be selectively configured in a compressed configuration (closed, having a reduced diameter) and an expanded (open) configuration, by operating a mechanical gear mechanism (not shown), such as by turning handle 242 at a proximal end of retractor 230 to operate a gear that engages teeth or screw threads to expand retractor 240. Retractor 240 operates similar to the old-style can openers, by turning a toothed gear. Handle 242 is turned (e.g., manually or otherwise (handle 242 may alternately be a gear)) to expand a small piece of sheet material to create a working tunnel. The material would be wrapped down upon itself within a gear feature at both ends engaged by a handle that would drive both gears simultaneously to fully open.

Retractor 240 can be used as generally described elsewhere herein, to perform a pelvic surgical procedure such as a SCP or other pelvic procedure; e.g., by insertion vaginally in a non-expanded configuration, selectively expanding retractor 240, performing the surgical procedure, then removing retractor 240, optionally by reducing the size of retractor 240 by reverse movement of handle 242 and connected gearing before removal.

Retractor 240B, illustrated at FIGS. 34I, and 34J, operates similar to retractor member 240, but a mechanical ratchet is used in place of gears to control the size of retractor 240, i.e., to expand and contract retractor 240. As illustrated, this method to open a tightly wrapped material would include a ratcheting feature such as teeth 241 on the material surface, which engage with a corresponding ratchet structure elsewhere on the material surface. Small mandrels could be passed through the inside diameter of the wrapped material to expand the wrapped material to a desired size while being held in place by the ratcheting features.

Referring to FIGS. 34E, 34F, 34G, and 34H, a pressure retractor system 256 operates by passing (e.g., transvaginally) a small flexible object (e.g., balloon or bladder 250) to a desired anatomical location (e.g., transvaginally) and expanding the flexible object (balloon 250) with pressure to a particular size, allowing a rigid tube 252 to be placed on the inside diameter of the expanded object/tube 250. Then cutting or otherwise removing the expanded tube 250 would provide access through the inside diameter of the rigid tube 252. The cross sectional size of expansion balloon 250 and rigid tube 252 can include a dimension $d_2$, working depth, and working space as described herein.

Referring to FIGS. 35A, 35B, 35C, 35D, and 35E, an expansion member 240C and technique in accordance with embodiments of the present invention are shown. From two to several small segments (side members 239, four as illustrated) are aligned in a circumferential fashion to form a small circle (diameter $d_1$). Portions of surfaces of the side members overlap, and these overlapping surfaces can include a ratcheting mechanism as described. By expanding the inside diameter of the expansion member 240C (circle/ring) the side members 239 can ratchet and expand to the desired shape and size (diameter $d_2$). The ratcheting mechanism may operates similar to that of a zip tie (only expand instead of contract) or spring type ratchet. Retractor 240C, illustrated at FIGS. 35A, 35B, 35C, 35D, and 35E, operates similar to retractor 240, but a mechanical ratchet system comprising pegs 243 and teeth 245 is used in place of gears to control the size of retractor 240C. As illustrated, this method to open an expansion member comprising two or more expanding side members would include a ratcheting feature such as a peg 243 (optionally functioning with a spring) in contact with opposing surfaces (e.g., teeth). Elongate structures such as wands 247 can be inserted through the proximal end opening to mechanically expand retractor 240C. The cross sectional size of expansion member 240C in an expanded configuration can include a dimension $d_2$, working depth, and working space as described herein.

Referring to FIGS. 36A-36C, an expansion member in the form of an expandable stent, and technique, in accordance with embodiments of the present invention are shown. Selectively expandable stent 260 may be similar to stent 120 described herein, capable of exhibiting an expanded and a contracted configuration, but without a bias to the expanded configuration. Instead, stent 260 can be selectively expanded and contracted, e.g., mechanically. An embodiment of such a stent, as illustrated, can include multiple pieces. A first piece is stent 260. A second piece can be a guide such as a stiff rod or shaft that can be placed within the internal space of stent 260 to expand the stent (causing simultaneous reduction in the length. An additional optional piece may be used to engage the guide with the stent 260; this piece can include mating features to the stent and guide, to create the working area of the incision. Referring to the structure of stent 260, several small hinged segments or connections (e.g., similar to a scissor jack, or pivoting nodes) 262 are aligned around the circumference of stent 260. By pushing or pulling on the length of the assembly, or by inserting the guide, the cross sectional size (inner diameter and outer diameter) will expand, and the length will correspondingly increase. Removal of the guide and compressive forces applied to the outside of stent 260 allow the diameter to be reduced, while the length increases. The cross sectional size of stent 260 in an expanded configuration can include a dimension $d_2$, working depth, and working space as described herein.

FIGS. 36B and 36C show end views of an embodiment of stent 260 in a compressed form (FIG. 36B) and as stent 260 expands by placing pressure from the interior, against the structure of stent 260, e.g., radial pressure in the direction of the radial arrows (FIG. 36C) by inserting a solid shaft, rod, or wand into the interior of stent 260.

Referring to FIGS. 37A, 37B, 37C, and 37D, an over-center expansion member and technique in accordance with embodiments of the present invention are shown. Expansion member 270 is assembled from elongate guide member 272 and elongate side members (or "distractors") 274, which can be introduced individually into a surgical incision and assembled together within a surgical site (e.g., a vagina and tissue path to a posterior pelvic region) by adding side members in a manner that gradually expands the size of the assembled expansion member 270 member during assembly, gradually opening the surgical site with each added side member 274. This embodiment comprises an over-center method of moving long side members (rods) 274 outward and then maintaining a position by going over center. Guide member 272 includes two channels or slots that engage an edge of a side member, allowing the side member to be slid into the slot to engage the guide and the side member. In use, guide member 272 can be inserted alone into a surgical incision (e.g., transvaginally). A first side member 274 can then be inserted into a channel 273. A second side member 274 can next be inserted into a second channel 273, creating a channel between opposing faces of the side members 274 that allows access to a surgical site. Optionally, and as illustrated, each side member 274 is tapered from a wide proximal end 274a, to a narrow distal end 274b. The cross sectional size of expansion member 270 and an opening defined thereby in the assembled configuration can include a dimension $d_2$, working depth, and working space as described herein. Optionally, expansion member 270 may be used in conjunction with one or more stacking cylinders introduced into the opening defined by expansion member 270 and surgical incision, along the length of expansion member 270. A stacking cylinder may maintain the size and shape of the opening along the length of the incision. If a cylinder is made of a polycarbonate or like clear (translucent or light transmitting) material, then light could be conducted through the cylinder to the sacrum.

Referring to FIGS. 38A and 38B, an expandable tube device and technique in accordance with embodiments of the present invention are shown. This embodiment comprises an expandable tube 280, including C-shape side members 282 that can expand to increase the size of the incision. Side members 282 can selectively expand or transpose from a convex to a concave form, to expand the cross-sectional size of an opening defined by tube 280. For example, the tube can be passed to a desired surgical location via an introducer tube. Then by removing a constraining feature (not shown) the C-shape is free to expand and is used as the new object for passing a larger C-shape or other expansion member. The process may be repeated using expanding C-shapes or expansion members until desired size of opening is achieved. The cross sectional size of an expandable tube 280 (and the opening defined thereby) in the expanded configuration can include a dimension $d_2$, working depth, and working space as described herein.

Referring to FIGS. 39A and 39B, sequential disposable dilator tubes and technique in accordance with embodiments of the present invention are shown. This embodiment allows for direct transvaginal visualization of a sacrum, optionally without the need to anchor to the patient table. The retraction would be isolated to the patient to prevent any potential damage if the patient were to move or be moved during a procedure. According to the use of sequential dilator tubes, a first (non-expandable) tube 286 of small diameter (e.g., 1-2 centimeters) is inserted into a surgical incision, and a second tube (288) is inserted into the first tube. The second tube 288 is expandable and is expanded to a cross-sectional size (diameter) greater than the first tube 286. Optionally, a third (expandable) tube (not shown) is inserted into the expanded second tube. The third tube can be expanded to a cross-sectional size (diameter) greater than that of the second tube (288). A fourth expandable tube may be inserted into the third expanded tube; i.e., multiple tubes can be sequentially inserted and expanded until a desired diameter of the surgical opening is achieved. The cross sectional size of an expandable tube 280 (and an opening defined thereby) in the expanded configuration can include a dimension $d_2$, working depth, and working space as described herein.

The various embodiments can be made from any suitable material or combination of materials. However, suitable examples include any biomaterial safe material for less than 24 hour contact with tissue, such as stainless steel, nitinol, polycarbonate, polypropylene, PET, polyurethane, silicone, polysulphone, and ultem. Any structure of an expansion member, retractor, tube, or other identified component may be capable of conducting light and images between the proximal and distal ends, or alternately one or more fiber optics cable may be incorporated into an expansion member, retractor, tube, or component thereof, to provide lighting and imaging functionalities that allow lighting, imaging, or both, at the accessed surgical site. The various embodiments can take any suitable size and shape, such as dimensions described herein, e.g., a contracted size may, for example, be in a range of 1-3 cm diameter and the expanded size may be in a range of 4-7 cm diameter.

The disclosures of U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382 are fully incorporated herein by reference in their entireties.

The implants, their various components, structures, features, materials and methods may have a number of suitable configurations as shown and described in the previously-incorporated references, or as described herein. Various methods and tools for introducing, deploying, anchoring and manipulating implants to treat incontinence, prolapse, or another pelvic condition, as disclosed in the previously-incorporated references are envisioned for use with the present invention as well as those methods and tools identified and described herein.

Also according to embodiments of the methods, implants, tools, and devices described herein, any of the described expansion members (e.g., tools, retractors, tubes, etc.) can be used for placing any desired pelvic implant, in a male or a female patient, and for any of a large variety of conditions, such as a pelvic condition. The implant can include any structural features useful for such treatment, including any desired size, shape, and optional features such as adjustability and anchoring systems. Any of these features may be previously known, or described in documents incorporated herein, or as described herein, for any particular implant and method. For example, some of FIGS. 40 through 84, inclusive, include examples of features of "anchors" (as that term is generically and inclusively used) that can be useful as desired according to any of the methods described herein. An implant that includes or is otherwise secured by any of the anchors described can be useful to treat any type of pelvic condition in a male or a female patient; as a single and non-limiting example, an implant that includes or uses an anchor as described can be used in a transvaginal SCP procedure to provide support to a vaginal cuff, through an implant that includes the anchor, the anchor being attached at a region of sacral anatomy such as a sacral ligament (e.g., anterior longitudinal ligament, a.k.a. the "anterior ligament" or "longitudinal ligament").

Referring to FIG. 40, a mesh fixation method for attachment of an implant to a ligament (e.g., a sacrum ligament such as a uterosacral or sacrospinous ligament, or other soft tissue such as muscle, and the like) is shown. Anchor 300 comprises a series or array of small barbs or hooks 302 attached to a mesh or similar type of generally flat structure (base 304, including a film, tape, strip, fabric, or the like, which may be polymeric, cadaveric, or natural), that can be subsequently sutured to the sacrum. These small barbs or hooks can include a generally elongate shape having a proximal end attached to base 304, and a shaft extending away from the base to a distal end, the shaft being oriented in an angled or in a perpendicular fashion away from base 304. A barb or hook 302 located at the distal end may be flexible, rigid, semi-rigid, polymeric, or metal, and can be in the form of an extension at the distal end such as a sharpened barb or other structure capable of penetrating a ligament by entry in one direction (or other soft tissue) and becoming engaged with the tissue and resist movement and removal from the soft tissue in a reverse direction. A barb or hook 302 can be of any useful size, for example may have a length or height (away from or above base 304) in the range from 1 to 4 millimeters, e.g., 1 to 3 millimeters.

In use, an array of barbs or hooks can allow for short-term tissue fixation for placement of a portion of an implant. Subsequent to this short-term fixation, ingrowth of tissue would secure the structure into the ligament (or other soft tissue) over time for long-term fixation. For example a method that places anchor 300 at a sacral (e.g., anterior longitudinal) ligament may include steps of: placing an anchor 300 (e.g., mesh with an array of barbs) in place at a surface of the ligament, pushing on anchor 300 against the ligament in a direction to push barbs or hooks into tissue (e.g., with "rod" extending through a surgical incision), and securing anchor 300 to the ligament using 1 or 2 small sutures to allow tissue in-growth and long term fixation. Anchor 300 can be useful to treat any type of pelvic condition; as a single and non-limiting example, anchor 300 can be used in a SCP procedure to provide support to a vaginal cuff, through the implant, attached at a region of sacral anatomy such as a sacral ligament. Optionally, anchor 300 (and any other anchor embodiments) can be provided with a drug coating (steroid for example) to increase the tissue growth to reduce the amount to time for the mesh to be fully encapsulated.

Referring to FIGS. 41A through 41D, a filled bladder anchor device and technique are shown. This method uses a hollow tube needle 310 that can be passed into or through a ligament, the needle optionally including a removable core. First, the needle 310 is used to puncture the ligament; the optional core is removed from the needle (from the proximal end of the needle) to open a passage (obturator) along the length of the needle. Then the needle 310 is used to place a balloon-and-suture assembly 312 between the ligament and the bone. Once the balloon has been expanded and filled (e.g., with bio-glue), this filled balloon structure functions as an anchor. An implant, mesh, or other structure or object can be tied to the sutures. The time needed for filling the balloon in within a range that allows curing of a bio-glue to occur within the duration of the surgical procedure.

Referring to FIGS. 42A and 42B, an anchor that includes a toggle rivet (316) device is shown. Rivet 316 can be of a standard "blind rivet" or "pop rivet" construction comprising a tubular or expanding head 320, a collar 322, and a "rod" or "mandrel" 318. Head 320 can be placed through a mesh (319) and through tissue (321); then rod 318 can be advanced away from collar 322 (see arrow B), causing head 320 to expand. This embodiment uses the rivet to puncture the ligament and then by activating the rivet, the mechanical lock (expanded head) secures the rivet to the ligament. The mandrel 318 breaks away and can be removed.

Figure 43D:
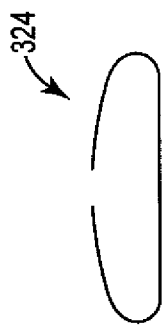
Figure 43C:
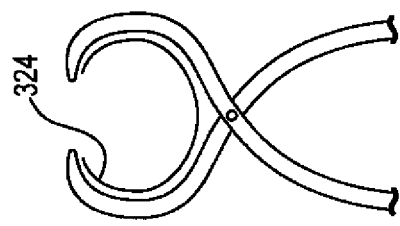
Figure 43A:
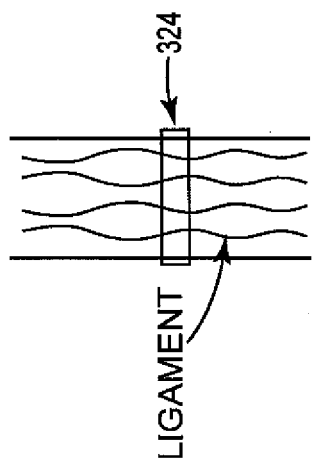
Figure 43B:
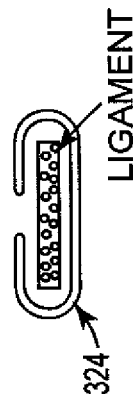

Referring to FIGS. 43A through 432D, a formed band anchor device and technique are shown. The band 324 comprises a piece of malleable metal or plastic (e.g., stainless steel, nitinol, etc.) configured into a rough "c" shape, thereby forming a staple-like structure. A modified pair of pliers 326 can squeeze band 324 into or around a ligament. The band could be used to attach the mesh directly to the ligament, or the mesh could be secured to the band prior to the procedure.

Figure 44:
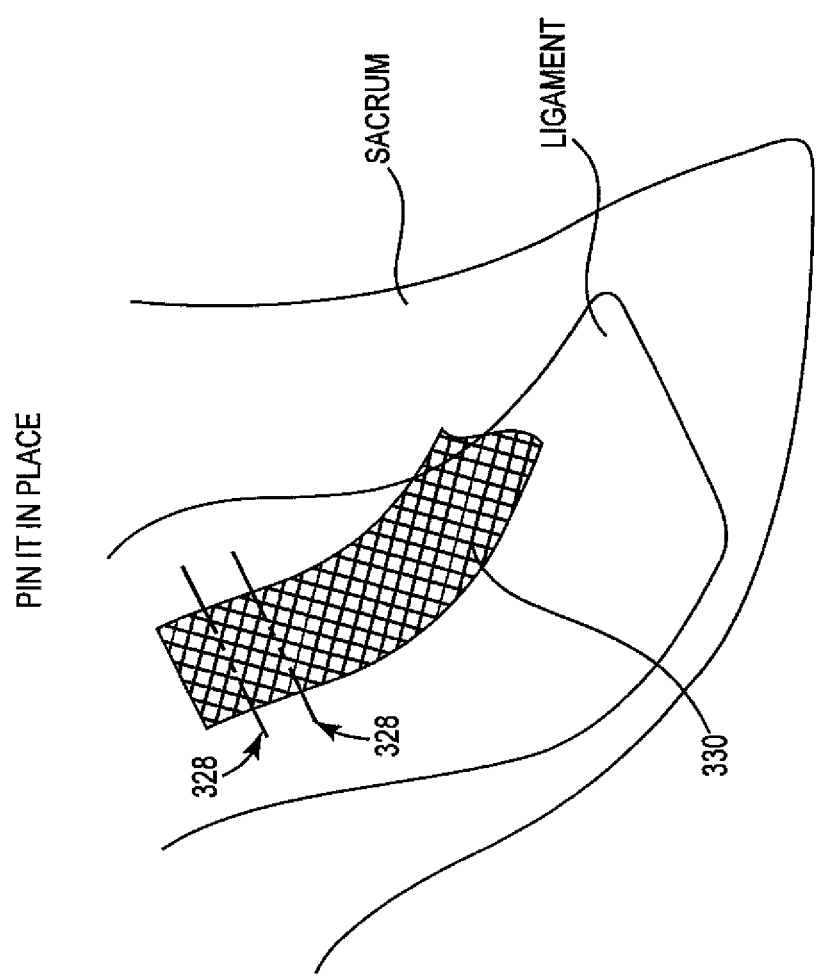

Referring to FIG. 44 a pin-in-place method is shown. This method comprises the use of pins similar to those used in the sewing industry. Pins 328 come can be inserted laterally into a mesh 330, and a ligament (e.g., the anterior longitudinal ligament) and travel to the midline. The mesh 330 is secured with the lateral pin approach. This technique prevents the needle tips from migrating out of the ligament and aids to prevent irritation of any surrounding tissue.

Referring to FIG. 45, passer devices and techniques are shown. This embodiment comprises using a rigid elongate passer device, transvaginally, to pass a portion of a mesh 336 implant through or behind a ligament (e.g., the anterior longitudinal ligament). The passer device 338 may be hollow (a hollow tuber passer), solid (e.g., a rod), or the like. Once the mesh is placed through or behind the ligament, both ends of the mesh are attached to the vagina, e.g., one end can be attached to right side of the vagina and the other end can be attached to a left side of the vagina. This attachment configuration can balance forces on the mesh, ultimately locking it into place and preventing migration.

Figure 46A:
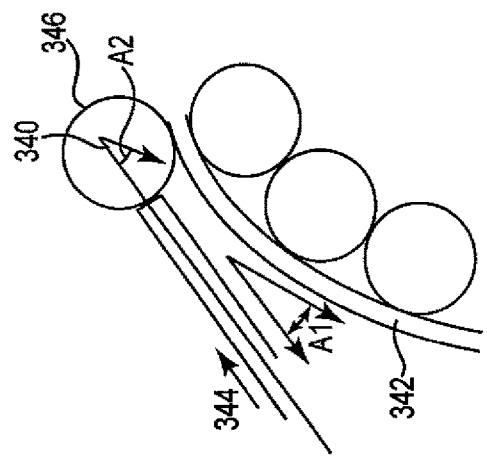
Figure 46B:
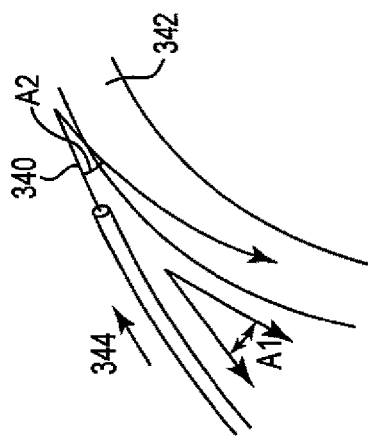
Figure 46C:
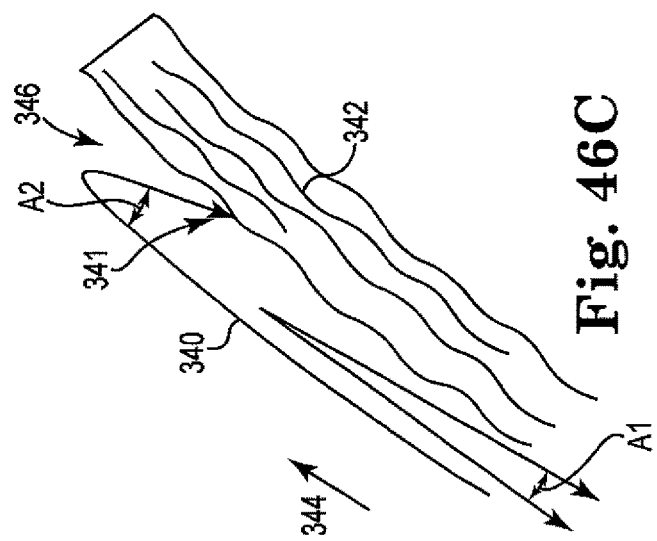

Referring to FIGS. 46A, 46B, and 46C, a "reverse" anchor technique is shown, that can be inserted by pulling the anchor in a reverse direction, instead of pushing. The devices and methods involve transvaginal placement of an anchor that includes a structure that can be inserted into ligament tissue by pulling on the anchor or an attached implant or insertion device, instead of pushing. One exemplary embodiment can involve a relatively flat and hook-shaped anchor structure (e.g., needle 340 or similar construction) that includes a distal tip that that is bend or folded over and back toward the shaft. This exemplary distal tip includes an elongate shaft portion and a folded portion that is folded or bent back toward the shaft at an acute angle (A2), which may be, e.g., less than 60 degrees, or less than 45 degrees. The anchor and distal tip can be inserted transvaginally and can approach the anterior longitudinal ligament (342) at a shallow angle (angle A1), and be advanced toward the ligament distally in a direction 344 (e.g., at an angle of approach of 45 degrees or less, e.g., 30 degrees or less, relative to the surface of the anterior longitudinal ligament, or approximately parallel to the surface). Upon contact of the tip of needle 340 with a surface or edge of ligament tissue, needle 340 can be manipulated by pulling in a reverse direction (in an insertion direction that is in the reverse of direction 340, e.g., in direction approximate to arrow 346); insertion of tip 341 occurs by a motion in insertion direction 346, which is in an approximately reverse direction from the direction of approach 344.

Anchor 340 can be placed using any useful type of placement device or tool, and can be connected directly or indirectly (e.g., through a suture) to an implant for treating a pelvic condition. An implant may include one or multiple reverse-type anchors, of any size. For example, a surface of a mesh or other implant may include many or multiple small reverse-type anchors of small dimension (e.g., less than 5 mm, or less than 3 mm), covering the implant surface.

As illustrated at FIGS. 46A, 46B, and 46C, the angle of approach (A1) to the anterior longitudinal ligament through a vaginal incision, and insertion of a reverse-type anchor (e.g., needle 340) by pulling in reverse insertion direction 346, can advantageously be more direct and more convenient relative to methods of placing anchors that involve pushing an anchor into tissue at a relatively more perpendicular approach angle. A relatively straight insertion tool can reach directly, in a relatively straight line, through a vaginal opening, through a vaginal incision, and to an anterior longitudinal ligament, without substantial lateral or up-and-down movement. The described approach angle and reverse-type anchor configuration also allow placement of an anchor at a location at or near a top of an anterior longitudinal ligament, at an upper location that generally includes thicker ligament tissue. Optionally, the folded portion of exemplary anchor 340 may be flexible so that upon passing anchor 340 into the anterior ligament, the portion folded over maintains shape until the motion is reversed, whereupon the folded section may enter tissue and unfold and lock into place, preventing any further movement.

Figure 47:
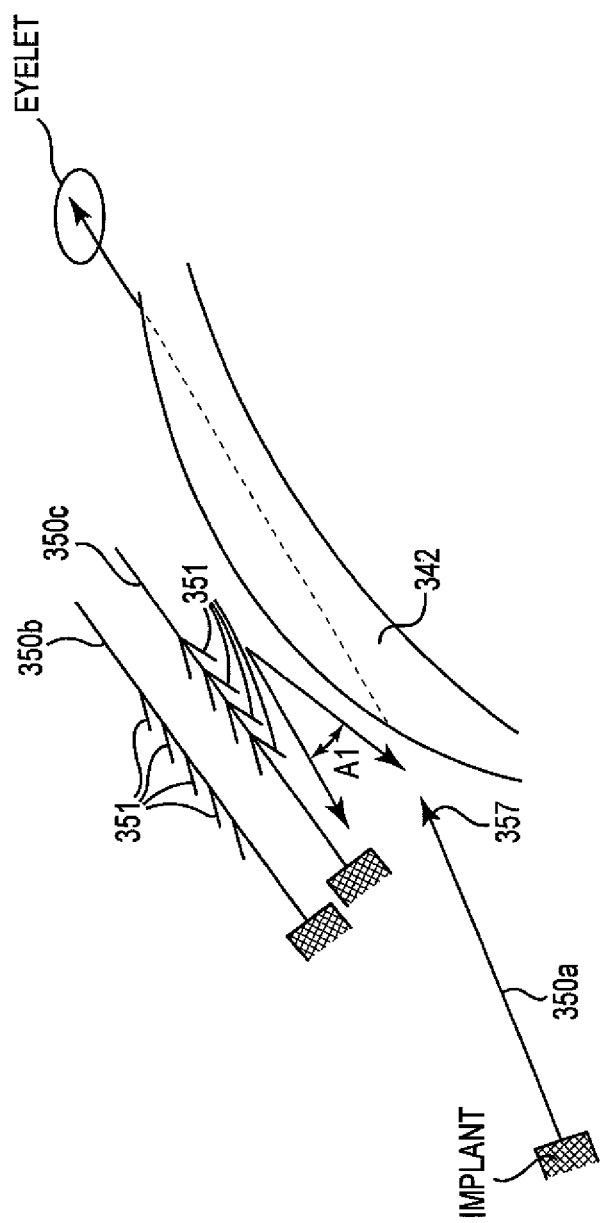
Figure 48C:
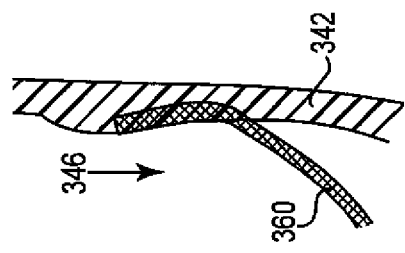
Figure 48B:
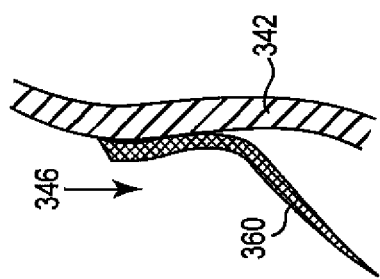
Figure 48A:
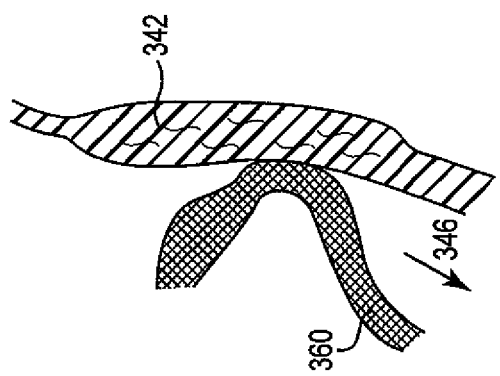

Referring to FIG. 47, alternate methods and devices also use a shallow transvaginal approach angle A1 between an anchor and an anterior longitudinal ligament, to push an anchor into the ligament at the shallow approach angle. Anchors 350a, 350b, and 350c can be any form of anchor, such as one that includes a thin longitudinal shaft comprising barbs (351) to inhibit reverse movement. One or more dart-like anchor structures 350a, 350b, or 350c, can be placed into the anterior ligament by following the surface of the sacrum (not shown). These darts can be include a narrow (e.g., rigid, metal or polymeric needle-like) shaft having a length sufficient to enter and optionally exit ligament 242 from shallow approach angle 242; a length of the shaft may be, e.g., from 0.3 to 1.2 centimeters, e.g., from 0.4 to 0.9 centimeters. The darts can optionally be advanced through the ligament by tunneling below the ligament surface, relatively parallel to a surface of the sacrum, until the dart is sufficiently buried or the tip has been exposed at a location of exit of the dart. If the tip is exposed, a cap may be placed; otherwise the physician can move on to the next step.

FIG. 47 shows a mesh implant that is directly or indirectly attached to anchor structures 350a, 350b, or 350c. According to alternate embodiments, multiple barbs 351 can be disposed directly onto a surface of an implant (e.g., a mesh or other film or tape), and the implant can be placed onto a surface of the anterior longitudinal ligament, or inserted into tissue of the anterior longitudinal ligament at a shallow approach angle. For example, referring to FIGS. 48A, 48B, and 48C, a tissue fixation method is shown that may involve a mesh 360, the mesh to comprising an array of hooks or barbs (not shown), e.g., reverse-type anchors, over a surface of the mesh (see FIG. 51). The mesh may contact tissue (FIGS. 48A and 48B) or be inserted into tissue (FIG. 48C), e.g., tissue of an anterior longitudinal ligament, at a low approach angle. The reverse-type anchors prevent movement in a reverse direction (346). These reverse-type anchors may be used alone as a means for short-term fixation of an implant followed by ingrowth and longer-term fixation. Alternately, these reverse-type anchors may be used in conjunction with additional anchor structures, such as a suture.

Figure 49A:
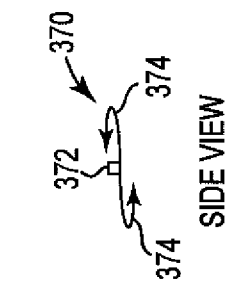
Figure 49B:
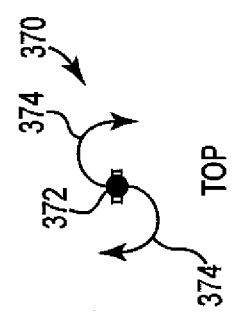
Figure 49C:
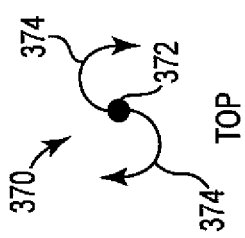

Referring to FIGS. 49A, 49B, and 49C, a spiral anchor device and technique are shown. Using a rotational approach, this embodiment use a two-pronged or multi-pronged anchor member 370 that can be rotated in a corkscrew-like fashion. Anchor 370 includes shaft 372 and prongs 374. Prongs 374 directly attach to tissue such as an anterior ligament by twisting anchor member 370 at the shaft. The barbs at ends of prongs 374 prevent reverse rotation. Advantageously, as shown in side view 49C, anchor 370 can have a flat profile, allowing the anchor to be inserted at a shallow depth (e.g., less than 5 millimeters.

Figure 50A:
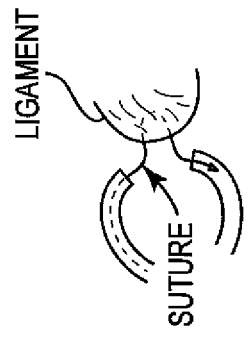
Figure 50B:
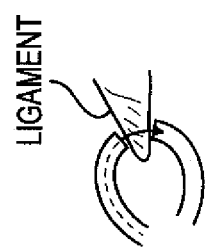
Figure 50C:
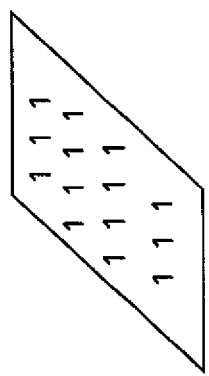

Referring to FIGS. 50A, 50B, and 50C, sacrum fixation methods are shown. A conventional device such as a suture passer can be used to pass a suture though the anterior longitudinal ligament, thereby providing assistance to the sacrum where it would be impossible to otherwise reach by hand.

Figure 54:
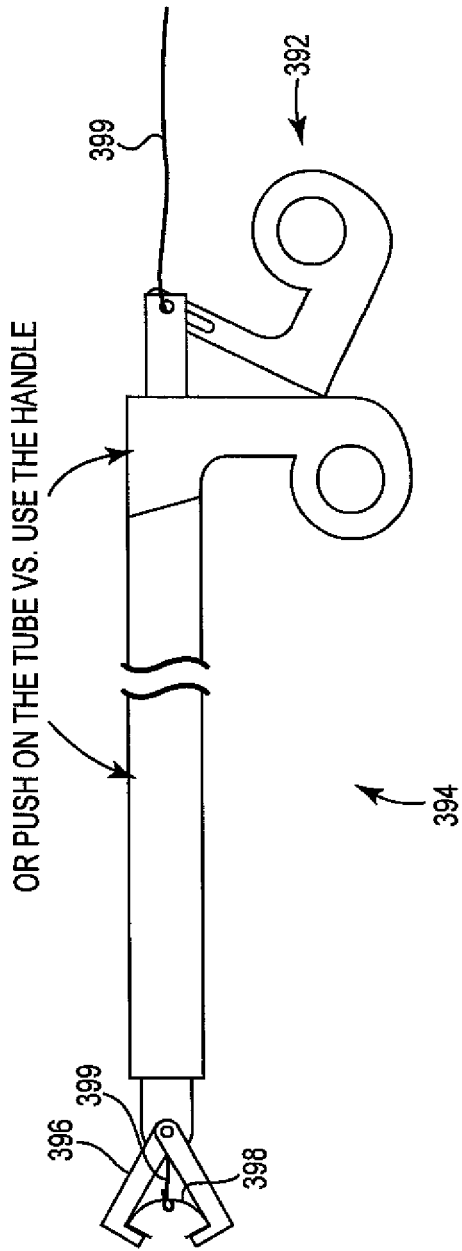
Figure 57A:
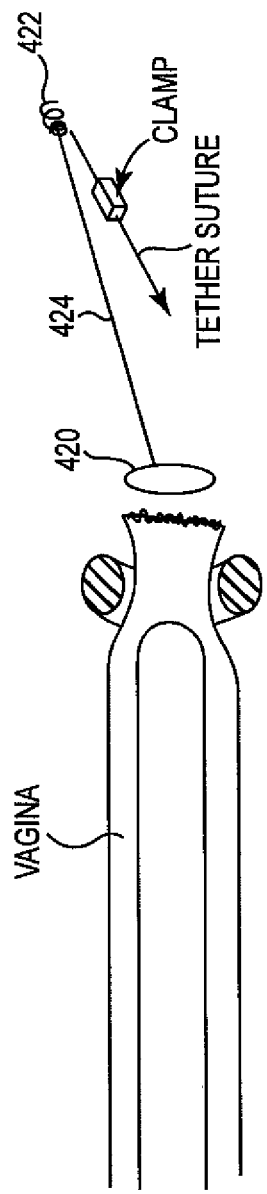
Figure 57B:
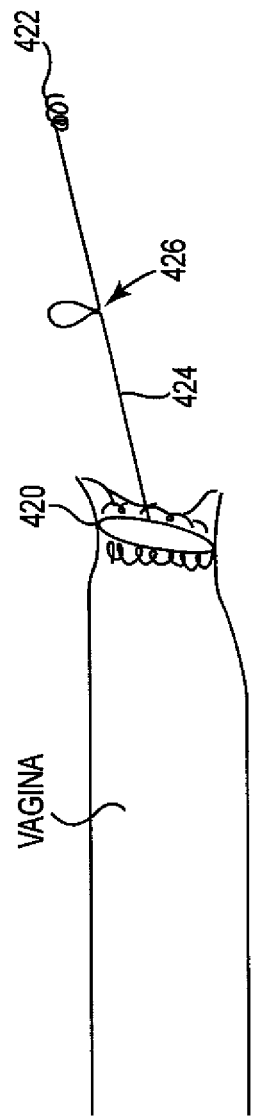
Figure 60B:
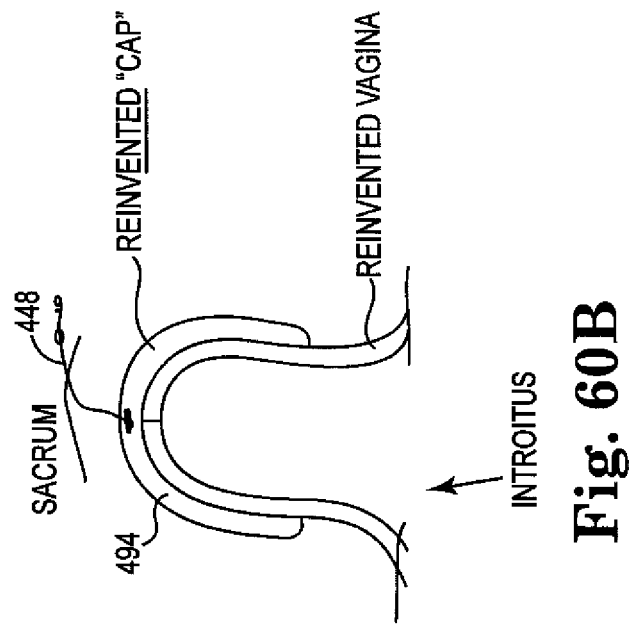
Figure 60A:
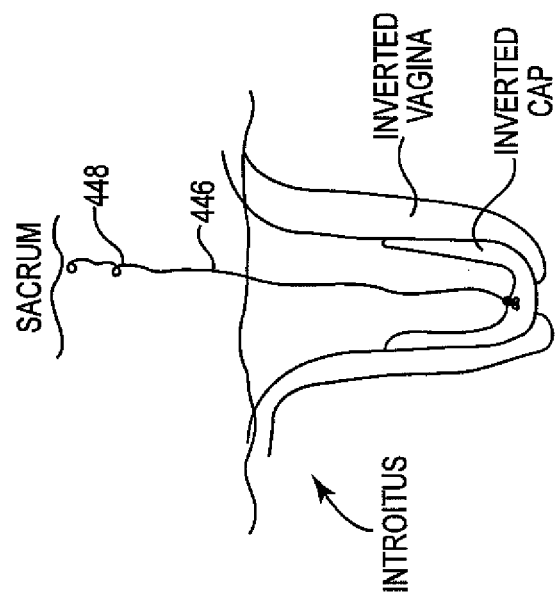

For example, referring to FIG. 54, a fixation device is shown. This device allows for deep transvaginal access to the sacrum and placement of a staple or other anchor into tissue, such as the anterior longitudinal ligament. By squeezing on the device handle 392 at a proximal end of device 394, the clamp 396 at a distal end close staple 398 into tissue such as an anterior longitudinal ligament. A suture 399 previously placed in the middle of the staple provides a means for fixation to the vagina, mesh, etc.

Figure 51:
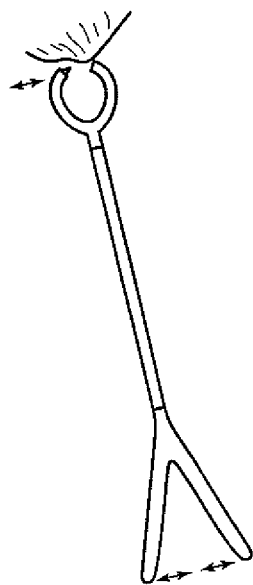

Referring to FIG. 51, illustrated is a hook and loop type fastener for securing to a region of sacral anatomy, such as the anterior longitudinal ligament. Small hooks (e.g., reverse-type anchors) grab the ligament, thereby holding the mesh to the patient tissue.

Referring to FIGS. 52A, 52B, 52C, and 52D, a spread anchor device 380, delivery tool (e.g., tube) 382, and method are shown. This embodiment is similar to the rivet embodiment discussed above, in that a mechanical manipulation expands a metallic or similar material beneath, within, or behind tissue (e.g., the anterior longitudinal ligament 342) to directly or indirectly secure an implant (not shown). The expanded element is then be used as an anchor. The anchor 380 may be compressed prior to insertion into tissue (e.g., see FIG. 52B) and may be biased to expand, or may be mechanically expanded, during or after placement within tissue (see FIG. 52D).

Referring to FIGS. 53A through 53C, a bent hook anchor device 390 and technique are shown. A suture or barbed suture is passed through tissue such as an anterior longitudinal ligament and a hook on the suture functions as an anchoring feature to prevent reverse movement. Another variation includes a barb to prevent rotation and reverse movement. Optionally or alternately an anchor 390 can be biased to take on one form (e.g., curved as in FIG. 53B) prior to insertion, then modify or become re-shaped (e.g. flattened or otherwise re-shaped as in FIG. 53B) after placement. This prevents irritation of any surrounding tissue.

Referring to FIGS. 55A through 55H, embodiments of sacrum ligament anchors are shown. In these embodiments a relatively flat piece of material with stamped or preformed features creates a depth to the part. These features prevent reverse rotation or reverse movement, similar to barbs discussed elsewhere herein. These embodiments decrease the complexity of fixating mesh to a region of sacral anatomy such as an anterior longitudinal ligament. This is especially advantageous where the implantation procedure is being performed transvaginally by placing an anchor 400 into an anterior longitudinal ligament, at a shallow approach angle (e.g., A1 as identified herein). Some or all of the devices in these embodiments can be made of any biomaterial safe material for implantation (tissue contact greater than 30 days). For example, Stainless Steel, Polycarbonate, Polypropylene, PET, Polyurethane, Silicone, Polysulphone, and Ullem can be used. However any suitable material is within the scope of the invention. FIGS. 55A, 55B, and 55C show a flat plate-like anchor 400 with a sharpened tip and a flexible, deflectable barb 402 extending from a top surface. FIGS. 55D and 55E show a longitudinally curved plate-like anchor 400 with a sharpened tip and a flexible, deflectable barb 402 extending from a top surface. FIGS. 55F, 55G, and 55H show a laterally curved (concave or convex relative to barb 402) plate-like anchor 400 with a sharpened tip and a flexible, deflectable barb 402 extending from a top surface.

Referring to FIGS. 56A, 56B, and 56C, a vaginal attachment tool and technique are shown. Suturing tool 410 comprises a hollow tube 412 having a longitudinal notch 414 cut out at the end of the tube. Within notch 414 are small access/relief segments 416 that allow an elongate coil or needle structure (e.g., 418) to pass along the length of tube 410 and access tissue of a vagina, when tool 410 is located within a vagina. As the needle 418 is passed along the length of the tube 412, at notch 414 and access segments 416, the needle 418 may protrude or be extended beyond the outside diameter of the tube (see arrows) to contact and capture a mesh and vaginal tissue. Use of tool 410 reducing the time required to attach a mesh to a vagina. At FIG. 57A, an anchor is placed at Referring to FIGS. 57A and 57B, an example embodiment is shown that uses a ring structure 420 at the vaginal apex. Ring 420 can be useful for multiple purposes of closing a vaginal incision and providing for attachment to the vagina with optional tensioning. The overall attachment may include a ring 420 that is supplied within a kit that provides a medium for both tensioning as well as wound closure. At FIG. 57A, anchor 422 is placed at a region of sacral anatomy (e.g., an anterior longitudinal ligament), and includes an eyelet through which suture 424 is threaded, allowing for tensioning between ring 420 and anchor 422 placed at a region of sacral anatomy. At FIG. 57B, anchor 422 is placed at a region of sacral anatomy (e.g., an anterior longitudinal ligament), and is secured to a suture 424 includes a loop or cinch at tensioner 426, allowing for tensioning between ring 420 and anchor 422 placed at a region of sacral anatomy.

Referring to FIGS. 58A and 58B, an embodiment is shown that leaves the vagina in the original place within the body. By passing a tool and mesh through two small vaginal incisions 430 (an anterior and posterior incision), a tool accompanies the mesh placement from inside the vagina, through each of the two small incisions 430, and to a location on the exterior of the vagina where mesh 432 can be placed and attached, e.g., by sutures 434. When mesh 432 is placed, in the proper location on the anterior and posterior exterior walls of the vagina, a small helical type tool can pass from inside to outside, through incisions 430, to capture the mesh. Optionally, after the two mesh pieces are placed, the anterior and posterior pieces are joined by an eyelet 436 that used for tensioning. Optionally, tension can be increased as the eyelet is pushed closer to the sacrum.

Referring to FIGS. 59A through 59D, embodiments of vaginal fixation devices and method comprises a single ring or a series of rings placed while the vagina is inverted and such that the rings are external to the vagina when placed inside the body. The rings 440 have small anchors (not shown) to keep the rings in place and in contact with the vaginal tissue. Sutures or mesh (442) can be attached to rings 440 to allow fixation of the rings to a region of sacral anatomy (referred to as "sacrum"). FIG. 59A shows an inverted vagina. At FIG. 59B, one or a series of rings 440 placed at the interior of the vagina as the vagina is exterior to the patient. When the vagina is re-introduced internally to the patient, as shown at FIG. 62B, rings 440 are positioned on the "outside" or "exterior" of the vagina, i.e., within the pelvic cavity. FIGS. 59C and 59D illustrate the vagina located internally to a patient, with rings 440 external to the vagina, and with one or more suture, mesh, or a combination of suture and mesh, connecting the vagina to a region of sacral anatomy.

Based on this same concept, as shown at FIGS. 59A and 59B, a similar method for vaginal fixation is used by placing an implant at an "interior" of a vagina as the vagina is located exterior to the patient and the vagina is inverted, so the implant is located on an "exterior" of the vagina after the vagina is re-introduced and placed interior to the patient. Implant 444 is in the form of a formed flexible and invertible, approximately hemispherical cup or cap that fits over the vaginal apex; this may be in any form or material that fits over a vaginal apex, such as a plastic, mesh or other flexible and invertible material. While the vagina is inverted (see FIG. 60A) the implant (e.g., mesh) 444 is secured to the external vaginal tissue. Then when the vagina is placed internally, the implant (e.g., cup) 444 is inverted so it helps to form the vaginal apex and also provides apical support to fixate/tension to the sacrum. The implant (e.g., cup) 444 may be of a size to extend full 360 degrees around a circumference of a vaginal apex, or may be a strip of material so access could be gained on either side or above and below for attachment to the external (non-inverted) vaginal wall. In an embodiment where the implant (e.g., cup) is a full 360°, it may be provided with openings in the sidewalls to gain access to attach the implant to the external vaginal wall. Also, an implant or "cap" may be a mesh or some other structure with a pre-attached anchor 448 and optional suture 446 for attachment to a region of sacral anatomy (referred to as "sacrum"). "Cap" may or may not be full 360°. It could be partial to allow access from two sides. Or have openings to allow access to suture/attach to vagina.

Referring to FIGS. 61A and 61B, with the vagina in its original place within the body (non-inverted and non-external), one or more small incision (430, similar to that of FIG. 58A, or optionally closer to a vaginal apex) is placed in the vaginal wall to allow a tool pass through the one or more incision 430 and to or near the vaginal apex. The tool can be used to pass a mesh, rod, or suture (450) through the vaginal wall at incision 430, and to a position that would allow the mesh, rod, or suture to be attached to the vagina for apical tensioning, by attachment to a region of sacral anatomy. The mesh, rod, or suture can be secured to the vagina by any securing means or structure such as a suture, staple, or other mechanical structure optionally including a ring or cap (as illustrated) that acts as a plug or block to prevent passage of a suture or mesh through the tissue. The mesh, rod, or suture can be secured to a region of sacral anatomy by any desired structure or means, such as an anchor (as described herein or elsewhere).

The aforementioned embodiments decrease the complexity of fixating mesh to a vagina. This is especially advantageous where the implantation procedure is being performed transvaginally because suturing a mesh or other object to a vaginal wall takes a significant amount of time. Some or all of the devices, structures, and methods in these embodiments can be made of any biomaterial safe material for implantation (tissue contact greater than 30 days). For example, Stainless Steel, Polycarbonate, Polypropylene, PET, Polyurethane, Silicone, Polysulphone, and Ultem can be used. However any suitable material is within the scope of the invention.

Figure 62:
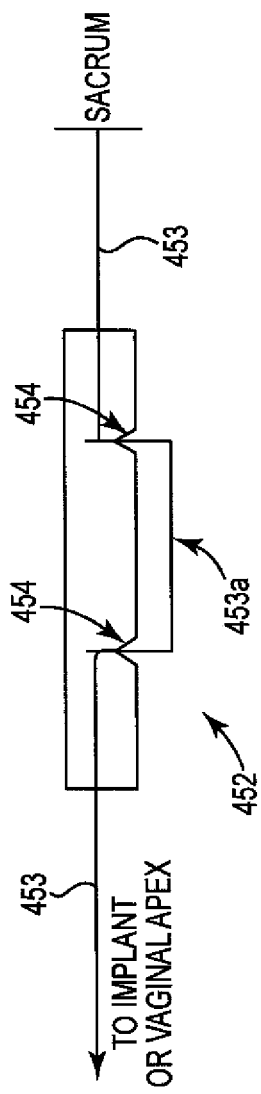

Referring to FIG. 62, a slip knot can be formed and placed using a card or other suture tying aid (452) provided on a suture or similar construction. In use, card 452 includes two slots (454) into which a suture 453 can be temporarily slid and held by friction. One end of the suture can be attached directly or indirectly to a region of sacral anatomy and the other end of the suture can be attached directly or indirectly to an implant or a vaginal apex. Once the two ends are situated and attached, the length of suture 453 between the attached ends can be adjusted by increasing or decreasing the amount of slack in the suture between slots 454, i.e., the length of suture 453a between slots 454. Once desired suture length and tension are adjusted and attained, and either during adjustment, prior to adjustment, or after adjustment, a knot is formed in the suture (e.g., along the length of suture 453a between slots 454). The suture tying aide 452 holds the suture or similar material at a specific tension for tying of the knot, then after the knot has been completed the "card" 452 can be removed and the desired tension remains in the suture. These devices and their use allow for desired end tension of a suture (or other implant) connecting a vaginal apex and a region of sacral anatomy.

Figure 63:
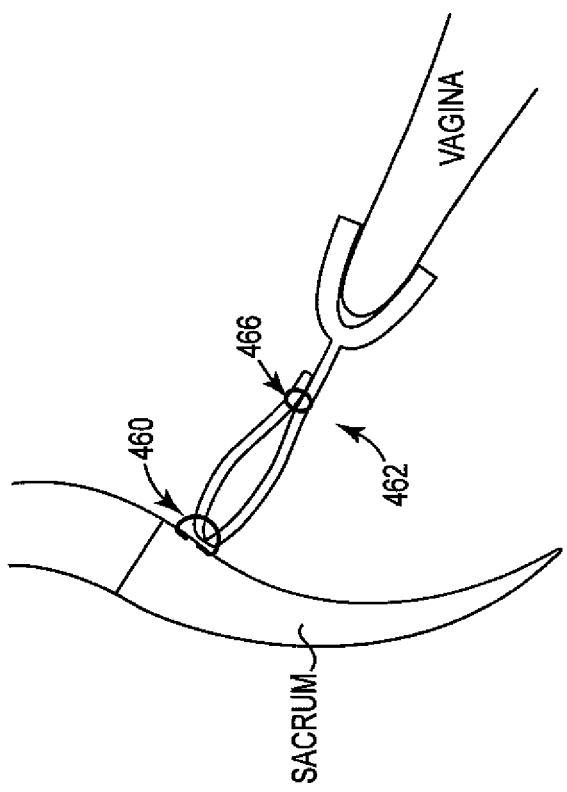

Referring to FIG. 63, a staple or other loop-containing anchor (460) is secured to the sacrum (i.e., a region of sacral anatomy) for use as a "pulley." Then an implant or portion thereof, e.g., a suture or a mesh (464) is directly attached to the sacrum through the pulley, with a loose end being folded back toward the vagina and pulled through the pulley to adjust tension on the connection between the vaginal tissue and the sacrum. A hemostat clip, staple, suture, or other means 466 can be used to secure the loose end to the connection to obtain the correct tension. In one variation of this embodiment, the mesh is secured to itself. In another variation, the mesh is secured to mesh attached to the vagina.

Figure 64:
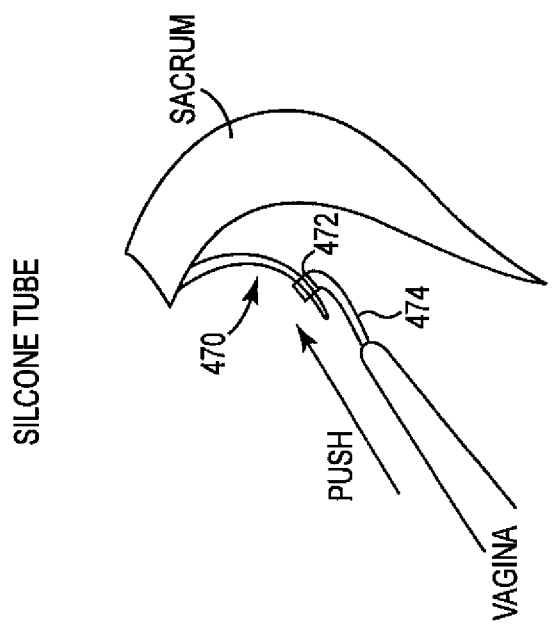

Referring to FIG. 64, this illustrates another alternate method and structure for adjusting tension and length of a connection (e.g., implant, suture, or the like) between a region of sacral anatomy and a vaginal apex. As shown at FIG. 63, a silicone tube/rod 470 or other pliable plastic or polymeric material (e.g., a mesh, suture, tape, strip) is attached at a sacrum (i.e., a region of sacral anatomy) (e.g., by use of an anchor described herein or elsewhere). An adjusting collar 472 is slid onto a loose end of material 470, and can be further slid or advanced along a length of the rod. Adjusting collar 472 is also attached (securely or adjustably) to implant 474, also some form of implant optionally in the form of a silicone tube/rod or other pliable plastic or polymeric material (e.g., a mesh, suture, tape, strip), implant 474 being attached directly or indirectly at one end to a vaginal cuff. Adjusting collar 472 allows selective relative positioning of implant 474 relative to material 470, to adjust length and tension of the connection between the vagina and the region of sacral anatomy. Final fixation of tension and length of the connection may be accomplished by a locking collar, adhesive, luer lock, or the like. Once locked, the tensioning is complete.

Figure 65:
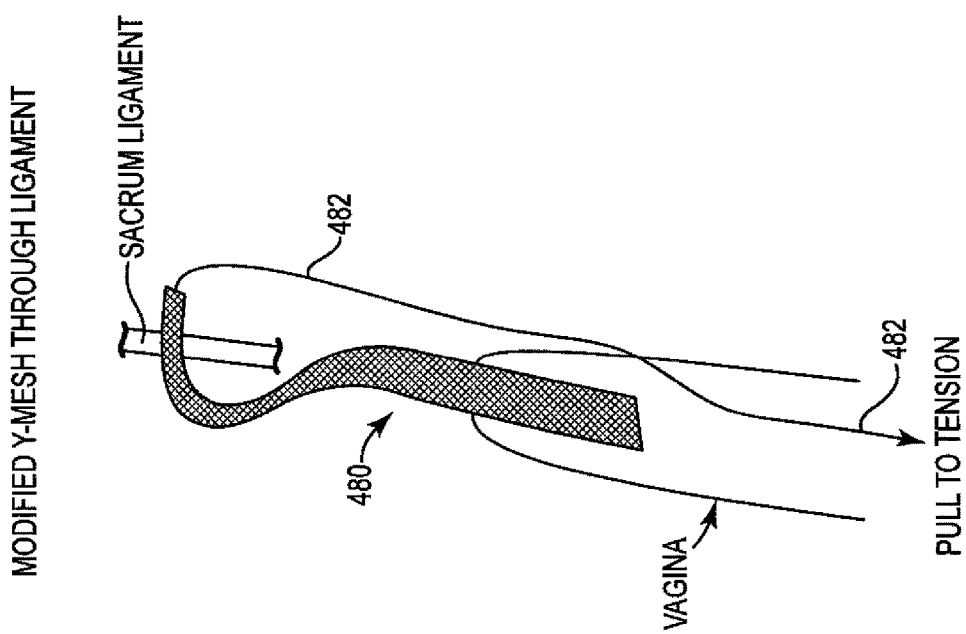

At FIG. 65, a modified strip, tape, or "Y-mesh" or "V-mesh" for use in a SCP procedure by placement through a ligament (e.g., an anterior longitudinal ligament) is shown. This embodiment is similar to that of FIG. 63 in that it uses the ligament as the pulley. As illustrated, a distal end of mesh 480 is passed through the ligament and tension is adjusted by pulling the mesh through the ligament and adjusting the length of mesh 480 that forms the connection between the ligament and vagina. A suture 482 can be used to lead the distal end of mesh 480 through the ligament, and adjust the length and tension. After placement, mesh 480 can be held in place by securing the distal end of mesh 480 to the portion of mesh 480 that extends between the vagina and the ligament, e.g., in a manner as previously described herein with regard to FIG. 63, such as by use of a locking-type collar, a staple, a suture, etc., which can be placed to connect the loose end of the mesh to the connecting portion of the mesh, to prevent the mesh from pulling out of the ligament.

Referring to FIGS. 66A and 66B, another alternate method and structure for adjusting tension and length of a connection (e.g., implant, suture, or the like) between a region of sacral anatomy and a vaginal apex, are illustrated. Referring to FIGS. 66A and 66B, a mesh implant 480 includes a proximal mesh portion 482 and a distal mesh portion 484. The proximal mesh portion 482 is attached to the vagina and the distal mesh portion 484 is attached to the sacrum (i.e., a region of sacral anatomy). The separate portion or pieces are adjustably joined with a crimp or clamp 486, which allows relative movement between portion 482 and portion 484, to adjust a length of implant 480 between the sacrum and the vagina, thereby adjusting tension on of the implant 480. The end result is two separate pieces of mesh joined and secured by a locking/securing mechanism, to provide a desired length and tension of implant 480 and desired positioning and support of the vagina.

Referring to FIGS. 67A and 67B, male (external) and female (internal) threaded engagements (490 and 492, respectively) are used as a mode for tensioning implant 480 having proximal and distal portions 482 and 482, the vagina, e.g., as a replacement for crimp or claim 486. By threading these two components together, the length of implant 480 and the distance between the sacrum and the vagina are decreased, which increases the tension on implant 480. This embodiment can also comprise one male thread and two opposing female threads (at opposing ends of a centrally-located male-threaded-member) to increase the amount of adjustment in a given length.

Referring to FIGS. 68A and 68B, yet another alternate method and structure for adjusting tension and length of a connection (e.g., implant, suture, or the like) between a region of sacral anatomy and a vaginal apex, are illustrated. Referring to FIGS. 68A and 68B, in a first depicted embodiment (at FIG. 71A, this embodiment having features similar to the system at FIGS. 66A and 66B), a crimp sleeve 486 or like construction is passed along two independent (separate) pieces of mesh, 484 and 482 (one attached to the sacrum the second attached to the vagina, respectively). Both pieces of mesh (alternately suture or like material) are passed through the crimp sleeve 486 until desired length and tension of implant 480 are achieved. The crimp sleeve 486 is then crushed to hold the two pieces (482 and 484) together and maintain tension. The second depicted embodiment (at FIG. 68B) uses a "finger trap"-type mechanism that takes up length and locks a round object. As two objects (pieces 482 and 484) are pushed (or pulled) together the distance is decreased and tension between a vagina and a sacrum is increased. The "finger trap" construction can be an aperture within piece 482, that holds the two objects (pieces 482 and 484) together by friction, e.g., by a one-way engagement that allows motion in a first direction (the direction of arrow "B" at FIG. 68B, but not in a reverse direction.

Referring to FIGS. 69A, 69B, 69C, and 69D, yet another alternate method and structure for adjusting tension and length of a connection (e.g., implant, suture, or the like) between a region of sacral anatomy and a vaginal apex, are illustrated. Referring to FIGS. 69A through 69D, a first depicted embodiment uses existing mesh type designs and hooks (483) to adjust the implant (e.g., mesh) length and tension. Two individual pieces 482 and 484 are pulled together and once the proper tension is reached, the hook of piece 482 is placed at a location of piece 484 to maintain the desired tension. Either of piece 482 and 484 can be placed on a proximal or a distal location, either toward a sacrum or toward a vagina. The second depicted embodiment at FIGS. 69C and 69D uses a suture as part of piece 484, for attaching hook 483 in one of multiple preformed knots or eyelets to hold the desired tension and length of implant 480.

Similar methods and structures for adjusting tension and length of a connection between a sacrum and a vagina are illustrated at FIGS. 70A through 70D. Referring to FIGS. 70A and 7013, two independent and separate pieces 482 and 484 are first secured to a vagina and a location of sacral anatomy. Ends opposite of the connection are adjusted and then bonded by friction, glue, heat seat, heat bonding, ultrasonic welding, or another bonding method to set a length and tension of the connection. Instead of a crimp or other like material, heat or another energy type, or another adhesive, can be used to bond or melt the polymeric pieces together to form a strong bond with desired length and tension.

Referring to FIG. 70C, the illustrated embodiment uses locking eyelets (485) slipped one-way over rods onto mesh to create a snap-fit arrangement. Other structures could alternately be used to lock the opposing pieces 482 and 484 together to produce a desired length and tension of implant 485. Another depicted embodiment at FIG. 70D uses a preformed tube 487 on one piece to secure the piece to the opposing piece and hold the pieces together. These two devices at FIGS. 70C and 70D were made for advantageous tensioning and length adjustment, allowing for the length and tension to be increased or decreased at pre-determined intervals.

Similarly, referring to FIG. 71A pieces 482 and 484 are adjustably connected at opposing ends (not connected to vagina or sacral anatomy) using a two-way or a one-way adjustable grommet 489 to allow a desired length and tension to be placed on the connection formed between the pieces as implant 480.

Similarly, FIG. 71B shows an alternate embodiment having an adjustable, notched, ratcheted, or toothed, push and snap-together connection between non-connected opposing ends of pieces 482 and 484. The adjustable connection includes a one-way barb or similar construction male connection member 491 that is inserted into and grips onto an opposing toothed polymeric female connection member 492. The vagina, connected to either of piece 482 or 484, can be drawn to the sacrum (connected to the other of piece 482 or 484) and limits movement in the reverse direction. The second depicted embodiment uses a cam-lock approach. By attaching one component to the sacrum and passing the second component from the vagina through the cam-locks the tension is increased in intervals. The adjustment also occurs in one direction unless the cam-locks were disengaged. Then the tension could be reduced. FIGS. 72A and 72B show an alternate embodiment, with teeth 493 of a surface of piece 484, which engage opposing teeth or ratchet surfaces (not shown) of piece 482, within a guide. 495, for one-way movement. FIG. 72C shows another alternate engagement structure that includes frictional surfaces, e.g., having teeth or other frictional surfaces, that pivot on cams to allow one-way movement between pieces 484 and 482 (in the direction of arrow 497.

Figure 73:
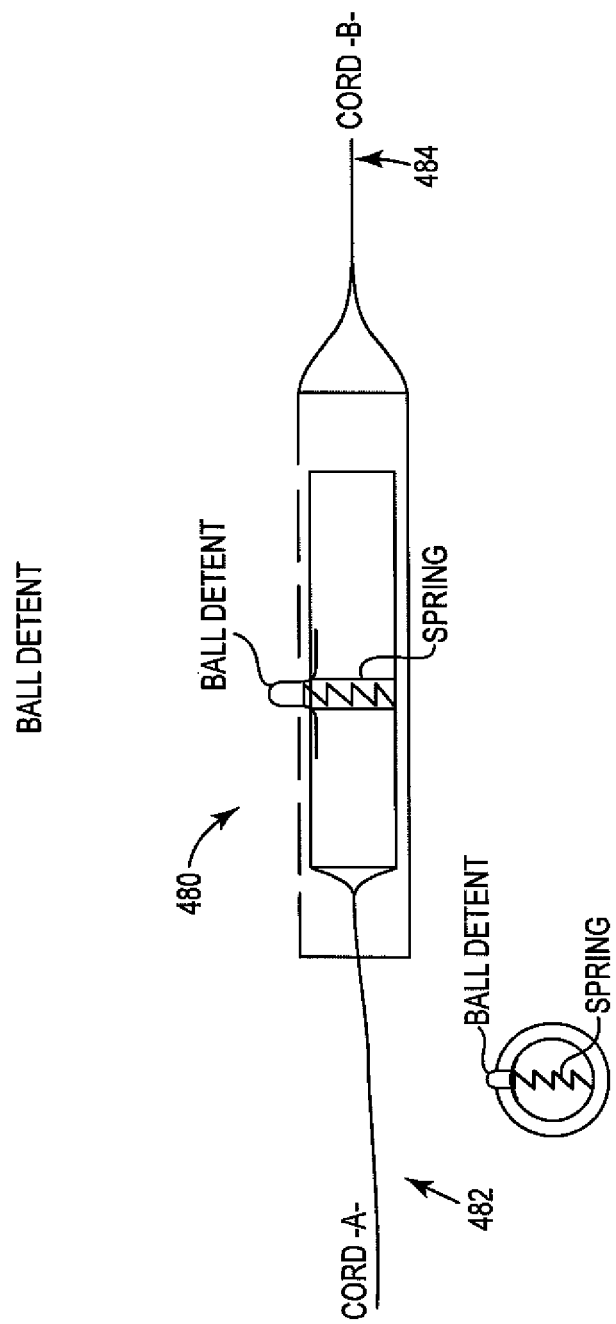

Another alternate engagement structure for adjusting a length and tension of opposing pieces 482 and 484 is shown at FIG. 73. Adjusting mechanism 499 is a ball detent that includes a spring-biased rod-and-tube structure and an opposing array of teeth or alternate frictional structures. The adjusting feature includes one or more cross holes drilled in a tube and a ball/spring attachment on the rod, the ball engaging the frictional structures, to selectively adjust tension and length of implant 480 in two directions. By aligning the ball and the cross hole in the tube, the assembly is locked until the ball is depressed and opposing pieces 484 and 482 can be moved to a different adjustment, the secured by releasing the spring.

Referring to FIG. 74, yet another alternate adjustment structure, method, and device for opposing implants pieces 482 and 484, pre-attached to vagina and sacrum (i.e., a component of sacral anatomy), comprises a semi-rigid helix 503 attached to the sacrum. Disposed in the device is a smooth hole 505 to pass the suture (482). The suture 482 is passed through the helix, through the hole, then back through the helix over itself, to provide for an adjustable, frictional engagement. After initial engagement between suture 482 and helix 502, by pushing up on the vagina, the suture 482 is allowed to move freely through the adjustment hole. The tension and length of the connection provided by implant 480 can be locked into place by pulling on the suture coming out of the vagina/incision.

The aforementioned embodiments of adjustable engagements for opposing implants pieces 482 and 484, pre-attached to a vagina and sacrum (i.e., a component of sacral anatomy), allow a physician to adjust the tension and length of a connection provided by an implant 480, between a vagina and sacrum, when securing the vagina to the sacrum through a single vaginal incision. Some or all of the devices in these embodiments can be made of any biomaterial safe material for implantation (tissue contact greater than 30 days). For example, Stainless Steel, Polycarbonate, Polypropylene, PET, Polyurethane, Silicone, Polysulphone, and Ultem can be used. However any suitable material is within the scope of the invention.

Referring to FIGS. 75A through 75C, various embodiments of devices and methods useful for a transvaginal approach of placing an implant for a treatment of a pelvic condition in a male or female anatomy, e.g., a sacrocolpopexy in a female anatomy, are shown. These embodiments comprise methods and devices for fixation of mesh to a region of sacral anatomy such as an anterior ligament of the sacrum, with direct mechanical fixation to the ligament.

FIGS. 75A through 75C depict an independent component configured to fixate an implant (e.g., mesh) to the sacrum (i.e., a component of sacral anatomy) where the attachment method is not directly connected to the mesh. A staple type device 520 includes a proximal end 522 having a handle and trigger, a shaft 524 (optionally curved as illustrated) that can be placed transvaginally, and a head 526 that can manipulate an end of an implant and an anchor such as a staple 530. Head 526 holds an implant (not shown), separately from an anchor, until the anchor or anchors (e.g., staple or staples) are placed through the implant and into the sacrum, securing the implant to the sacrum. The trigger on handle 522 pulls a small block that drives the anchor staples into the ligament either in a perpendicular orientation, or preferably at a shallow angle. FIG. 75C shows a face of head 526 that can contact a ligament. Staples 530 are engaged at head 526, and upon activation of the trigger will be expelled through mesh and into a ligament, optionally (e.g., preferably) at a shallow angle such as an angle of 60 degrees or 45 degrees relative to a surface of the ligament, to allow a greater length of staple 530 to be inserted into the ligament. FIG. 75D shows a side view and an end view of head 526, with a separate clamp 532 that is capable of holding an end of an implant on a surface of head 526 that will be disposed against a ligament. Clamp 532 can optionally grasp and release mesh 534 to hold implant (e.g., mesh) 534 between head 526 and a ligament, while staple 530 is released from head 530 to pass through implant 534 and into the ligament.

Figure 76A:
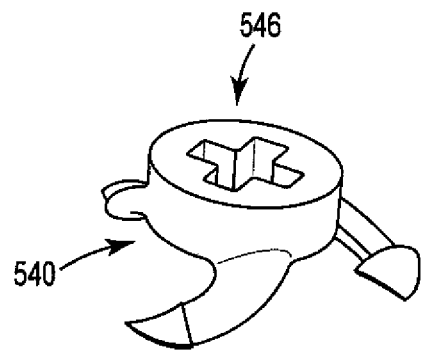
Figure 76B:
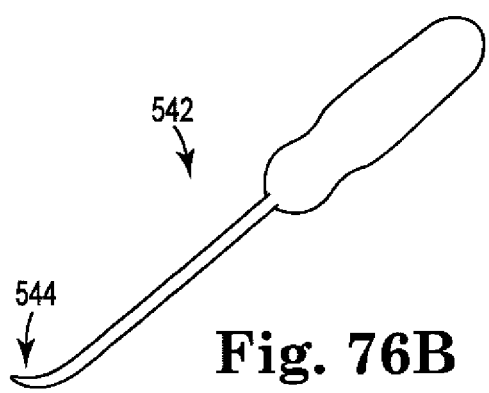
Figure 76C:
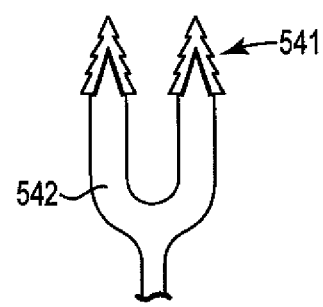

FIGS. 76A, 76B, and 76C depict multi-pronged fixation elements (anchors, or staples) capable of holding an implant to a region of sacral anatomy. FIG. 76A illustrates a useful barbed anchor (staple or "molly") 540 for placement at a ligament such as an anterior longitudinal ligament. See also FIG. 77C. According to one depicted variation, a small turn of a screwdriver-type installation device can be used to turn anchor 540, with slight pressure, to cause anchor 540 to advance (optionally through an implant, and) securely into a ligament (e.g., to anchor an implant). Tool 543 comprising an elongate shaft to allow transvaginal access to a region of sacral anatomy, can be used to place anchor 540 by twisting of and optional placement of pressure onto anchor 540. Preferably anchor 540 can be inserted by twisting, using less than a complete turn of tool 543, such as a half of a complete turn or a quarter of a complete turn. Tip 544 of tool 543 engages screw head 546 of anchor 540. The barbs on the anchoring arms prevent the fixation element from backing out of engaged tissue. This fixation element (anchor) 540 can be operated independently, or it could be attached indirectly or directly to an implant (e.g., mesh). In another alternative an implant can be overmolded or glued to the fixation element (anchor) 540, or the anchor can be overmolded to the implant.

Figure 77A:
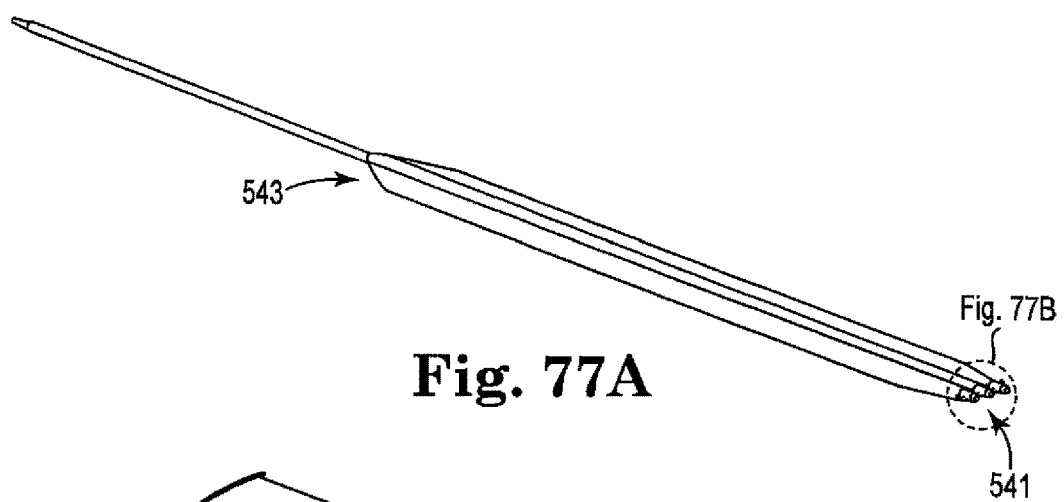
Figure 77B:
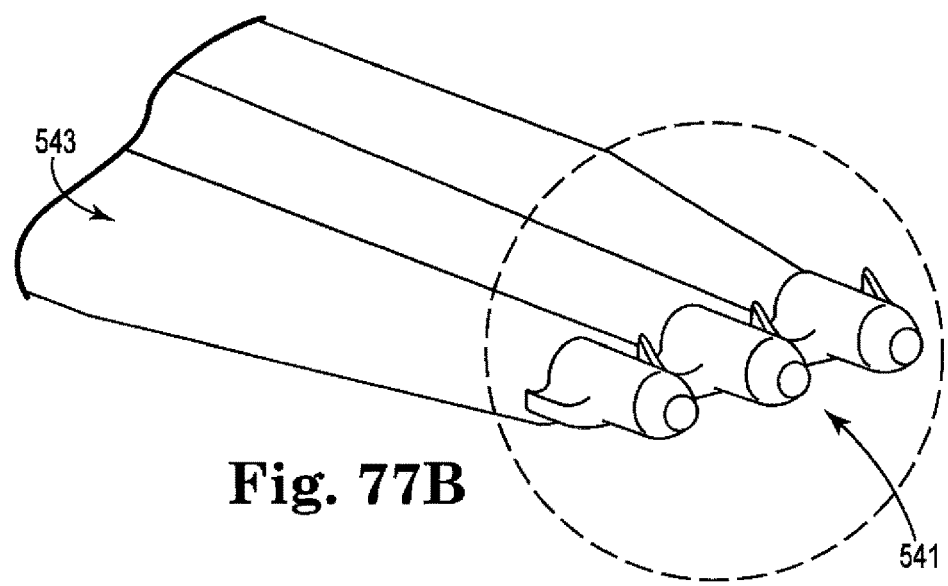
Figure 77C:
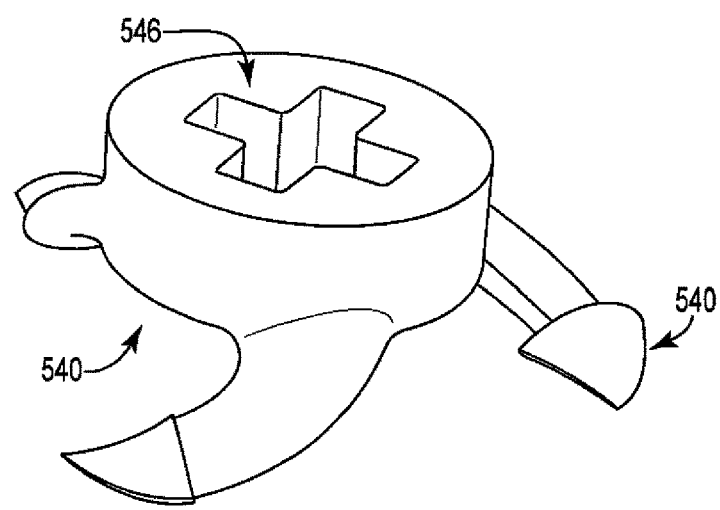

In another depicted variation, at FIGS. 76C, 77A, and 77B, an alternate anchor 541, in the form of a barbed multi-self-fixating-tip-type staple or anchor can be pushed into a ligament (the anchor being optionally attached to or through an implant) by pushing tool 542 having a multi-pronged (e.g. forked) end to engage anchor 541. As shown at FIGS. 77A and 77B, three or more dart-style (self-fixating tip-style) anchors can be secured to an end of an implant 543 in parallel to allow for secure engagement into a ligament. The size of these anchors can be reduced compared to other self-fixating tips, without sacrificing holding power, by use of multiple anchors 541 in parallel. For example a length may be, e.g., less than 7 millimeters, such as from 1 to 5 millimeters or from 1 to 4 millimeters, to allow for perpendicular or shallow angle (an approach angle A1 of 60 degrees, e.g., 45 degrees, or less) approach toward and entry into an anterior longitudinal ligament (see FIGS. 46, 47, and 48, inclusive, and related text).

Mechanically securing an implant (e.g., mesh) to a ligament simplifies a pelvic implant procedure by eliminating the need for the physician to place sutures deep into the vagina in a transvaginal approach. The fixation elements (anchors) can be directly attached to the implant or operated separate from the implant and placed through the implant passing also into the ligament.

The fixation elements of the aforementioned embodiments can be comprised of stainless steel, polypropylene, or other suitable implantable metallics and/or plastics.

Referring to FIGS. 78A and 78B, another embodiment of methods and devices for securing an implant (e.g., mesh) to vaginal tissue, is shown. A vagina is distended by a device (550) inside of the vagina, and an implant (e.g., mesh) 554 is secured to the outer vaginal wall by a set of coil-type screws 552, each with a trailing suture to produce a loop-type suture attachment or stitch. These coil-type screws 552 sit inside of a housing of a tool (not shown) to control the depth and location of the coil as the coil passes through the tissue and implant. As illustrated, two helical coils operate in parallel to place a series of two adjacent loop-type stitches, using two separate and adjacent suture materials, one suture material for each screw 552, each screw and suture placing multiple loop-type stitches along a length of implant to secure the implant to vaginal tissue. The two adjacent screws can turn together in one direction, or in opposite directions. Once the placement is completed, the coils are left in place to hold the mesh to the vaginal wall.

Referring to FIGS. 79A through 79D, using the same distended vaginal state, sutures are tied to an implant (e.g., mesh) 562, in the shape of a "U." A small needle or similar passing device 564 can pass the vaginal wall and the loop (565) at the other end (once passed through the vaginal wall (not shown) and implant) and are secured by a locking feature 566 that is positioned (e.g., molded into) the implant (e.g., mesh) (see FIG. 79C) (e.g., an eyelet, grommet, or similar frictional structure as disclosed in the present application, or elsewhere).

Figure 80:
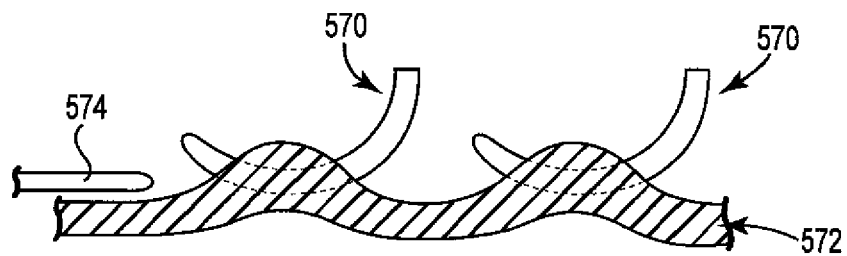

Referring to FIG. 80, an alternate method or approach to passing a suture or connective engagement through tissue of a vagina is depicted. The depicted embodiment uses one or more needles 570 to pull tissue 572 up or displaces it, to allow another (e.g.,) straight object (e.g., straight needle 574) to pass through the lifted vaginal tissue.

Figure 81A:
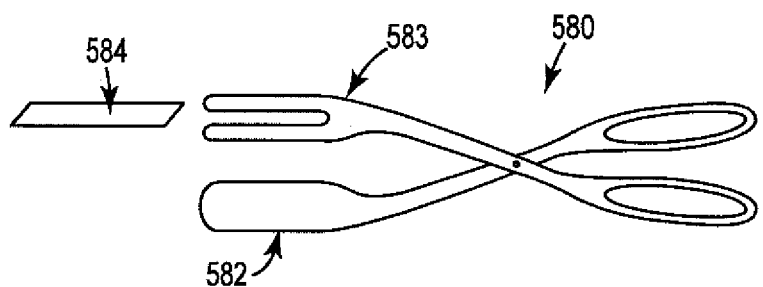
Figure 81B:
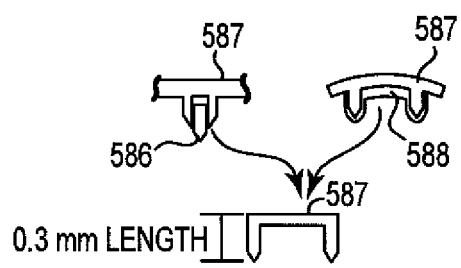

Referring to FIGS. 81A and 81B, pliers 580 and a vaginal distension device 582 (e.g., on one jaw of pliers 580, as illustrated) are used along with a reloading cartridge 584 for the vaginal fixation. The cartridge 584 is pre-loaded into jaw 583, along with an implant (e.g., mesh), staples, and applicator plate 587. The distension portion holds the vaginal tissue in place, and then by squeezing the pliers the implant mesh is secured to the vaginal wall by passage of a suture (e.g., 586 or 588) through the implant and into vaginal tissue. The device is pulled out and a new cartridge is loaded for an additional mesh fixation.

The aforementioned embodiments of attachment of mesh to a vaginal wall can advantageously reduce the time needed to secure the mesh to the vagina, thereby saving approximately 20-50 minutes in a procedure.

The fixation elements of the aforementioned embodiments can be comprised of stainless steel, polypropylene, or other suitable implantable metallics and/or plastics and/or polymers.

Various implants or systems are envisioned for use with the present invention, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382. Accordingly, the above-identified disclosures are fully incorporated herein by reference in their entirety.

Referring generally to FIGS. 82A through 82D, various embodiments of methods and devices for a combination anterior or posterior prolapse repair with other treatments for pelvic floor disorders such as urinary incontinence, pelvic floor decent (levator avulsion), and/or sacral fixation are shown. It is further understood that other conditions and devices are applicable without departing from the scope of the invention. Implant (e.g., mesh) 600 includes a tissue support portion 604, two small arms 602 located at the lateral locations of the tissue support portion 604, and extending laterally, can be anchored to the pelvic floor to support tissue of a pelvic floor (e.g., levator muscle). These anchor/fixation sites may be used to provide further pelvic floor support for levator avulsions or a descending pelvic floor. The anterior or posterior implant portion can also house the levator floor support, apical sacral fixation, and/or urinary sling support.

Figure 82A:
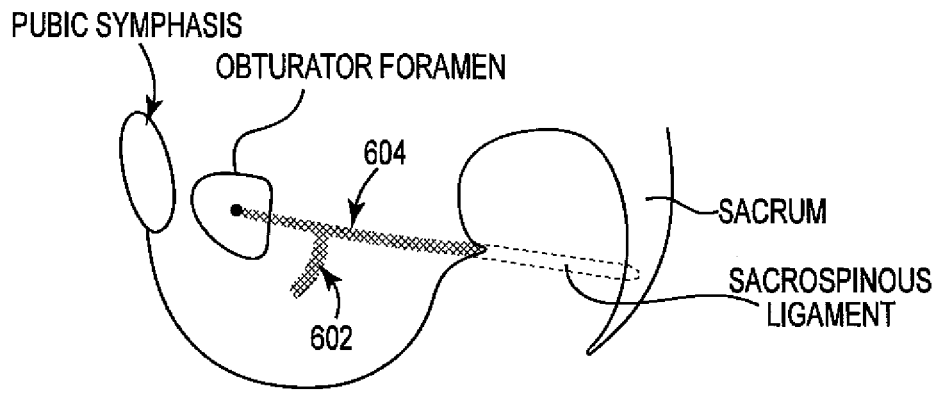
FIGS. 82A-82D depict a combination levator/prolapsed support device in accordance with embodiments of described inventions.
Figure 82B:
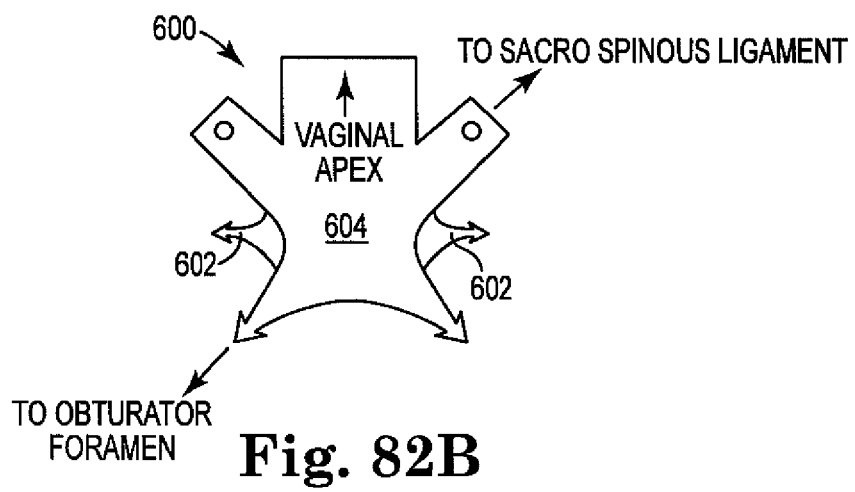
Figure 82C:
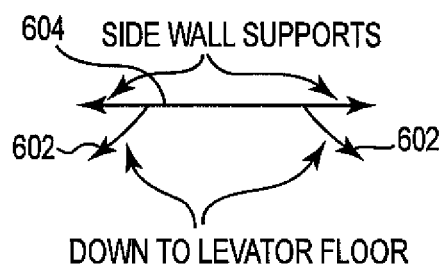
Figure 82D:
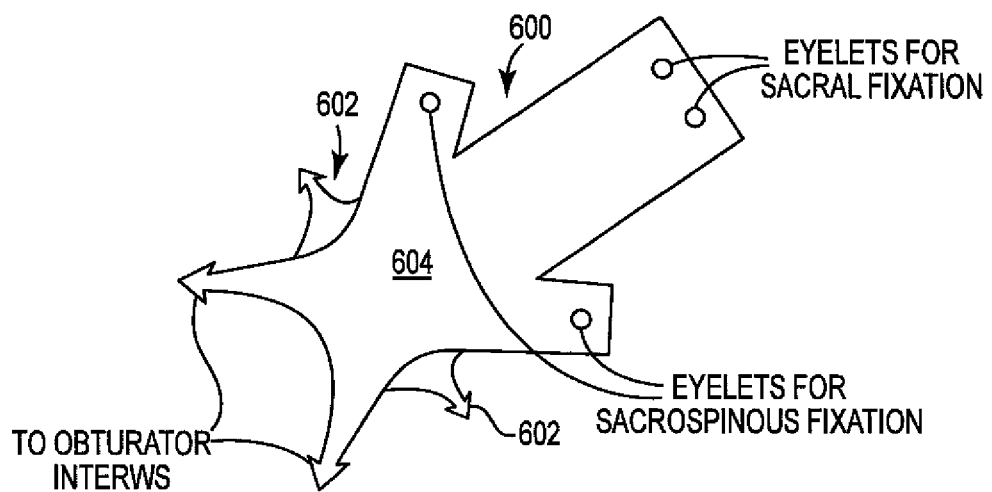

Still referring to FIGS. 82A through 82D, anterior implant 600 can include additional left and right, anterior and posterior extension portions, any of which can be adjustable, to attach to opposing left and right obturator foramen in an anterior direction, and to left and right sacrospinous ligaments in a posterior direction. In specific, a posterior attachment for affixing to a region of sacral anatomy may be adjustable (see FIG. 82D). The anterior prolapse mesh may be integrated with the levator floor support. In addition, it may include the urinary sling for incontinence. Another variant is illustrated at FIG. 82D.

A posterior mesh (not illustrated) similar to anterior implant 600 could share many of the same features as implant 600 but could without the anterior extension portions for fixation to the obturator foramen.

FIGS. 83A through 83D illustrate a transvaginal or laparoscopic method for supporting an the apex of a vagina by fixation and support from a region of sacral anatomy, using an adjustable implant. The depicted example embodiment comprises a "Y" mesh implant 620 having two mesh arms 622. Implant 620 includes a posterior portion 624 for attaching to a sacrum (i.e., a location of sacral anatomy), and two mesh or polymeric rod arms 622 that can be can be routed through an aperture (e.g., locking eyelet) on each of two anterior portions 626, which are attached to vaginal wall tissue to support a vaginal apex. Anterior portions 626 include an anterior area 628 for attachment to a vaginal wall and a posterior area 630 that includes an eyelet 632 for adjustably engaging one each of the two arms 622. With implant 620 secured to a sacrum and each of anterior portions 626 attached to vaginal wall tissue, each arm 622 can be led through one of the eyelets 632. A tool such as tensioning device (640) could be used to push the eyelet further up the arm 622 (which is attached to the sacrum) until a specific tension has been reached. Tool 640 of FIG. 83C includes a tension indicator gauge to measure tension. Tool 642 at FIG. 83D is configured to manipulate the rectum to move the rectum out of the way to provide a clear view of the sacrum.

Figure 84A:
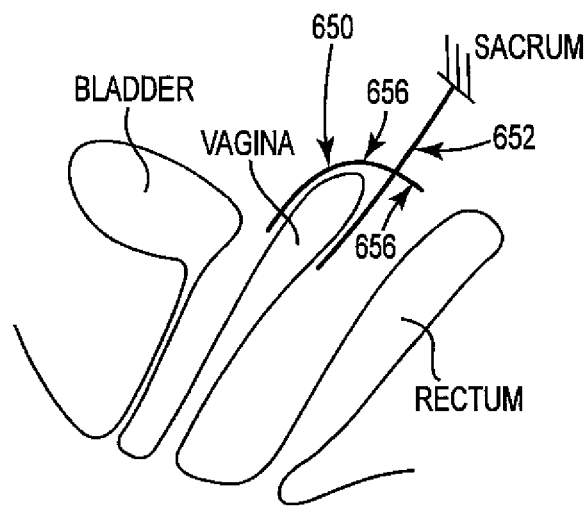
Figure 84B:
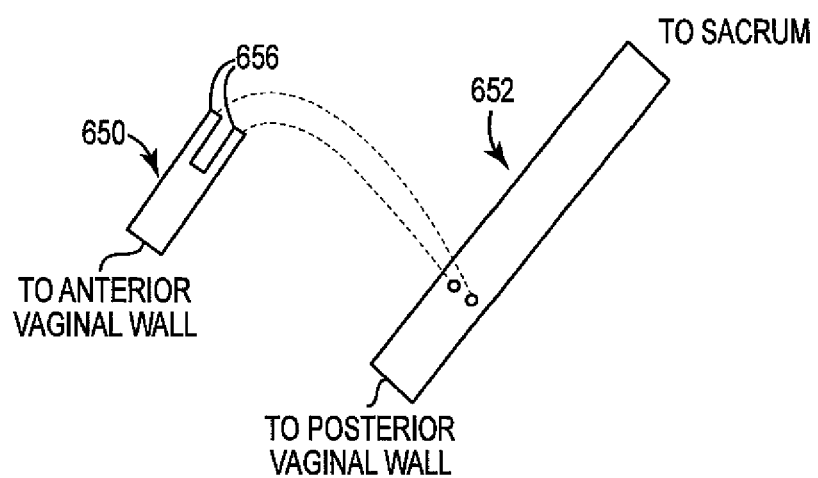

Referring to FIGS. 84A through 84D, an adjustable vaginal apex support device uses an anterior implant (e.g., mesh) 650 and a separate a posterior implant (e.g., mesh) 652 to allow for separate adjustment in vivo to obtain proper support of a vaginal apex. Referring to FIGS. 84A and 84B, anterior and posterior implant portions 650 and 652 are secured to anterior and posterior vaginal walls, and tensioned separately at the vaginal apex with posterior mesh 652 being secured to the sacrum. By selective movement of tabs 656 of anterior mesh 650 through apertures (e.g., grommets or alternate frictional or locking apertures) 658 of posterior mesh 652 tension of the combined mesh implant and positioning and support of the vaginal apex can be adjusted.

Figure 84C:
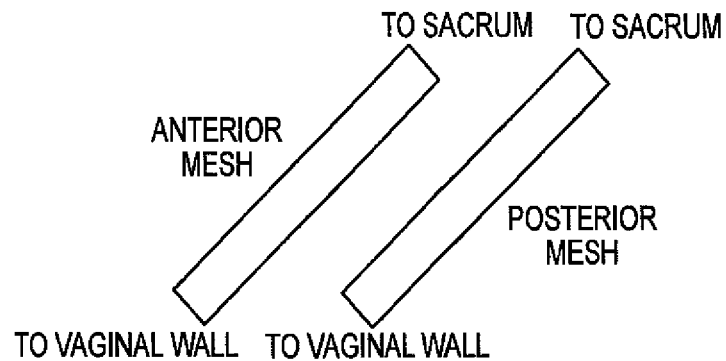

Referring to FIG. 84C, a SCP or related procedure for supporting a vaginal apex can be performed using two separate implants. One implant, the anterior implant, attaches to a region of sacral anatomy (e.g., an anterior longitudinal ligament) at a posterior end, and to a vaginal wall (e.g., an anterior vaginal wall) at an anterior end. The second implant, the posterior implant, attaches to a region of sacral anatomy at a posterior end, and to a vaginal wall (e.g., a posterior vaginal wall) at an anterior end.

Figure 84D:
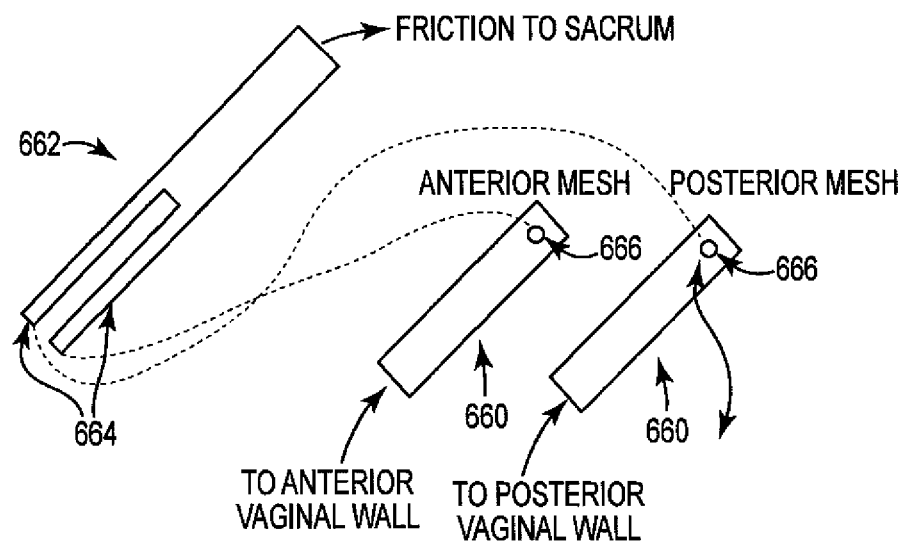

FIG. 84D shows an adjustable implant system similar to that of FIG. 84B, with tab and eyelet features located at opposite positions. Specifically, an adjustable vaginal apex support device uses two anterior implants (e.g., mesh) 660, and a separate a posterior implant (e.g., mesh) 662 to allow for separate adjustment in vivo to obtain proper support of a vaginal apex. The two anterior implants 660 are secured one each to an anterior and a posterior vaginal wall. Posterior implant portion 662 is secured to a region of sacral anatomy, e.g., an anterior longitudinal ligament. Tabs 664 of posterior implant 662 are inserted through eyelets 666 on each of the two anterior implants 660. Each tab can be adjusted through its corresponding eyelet, and tensioned separately at the vaginal apex with posterior implant 662 being secured to the sacrum. By selective movement of tabs 664 of anterior mesh 650 through eyelets (e.g., grommets or alternate frictional or locking apertures) 666 of anterior implants mesh 660, tension of the combined mesh implant and positioning and support of the vaginal apex can be adjusted.

Figure 85A:
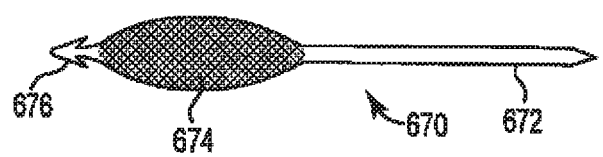
FIGS. 85A, 85B depict a mesh tensioning device and method in accordance with embodiments of described inventions.
Figure 85B:
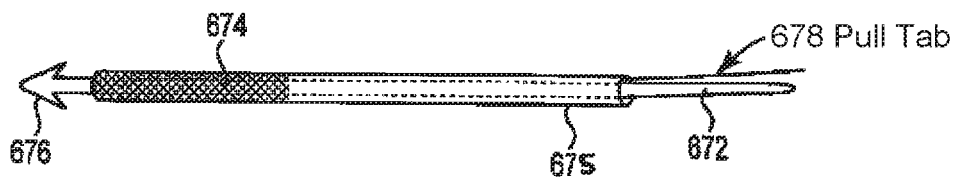

Referring to FIGS. 85A and 85B, a mesh tensioning device and method are shown. Mesh tensioning device 670 can include a polymeric rod 672, an attached mesh portion 674, and an anchor 676 such as (as illustrated) a self-fixating tip. An aperture (e.g., locking eyelet) on an opposing portion of an implant allows adjustment of tension between the implant and tensioning device 670 prior to the mesh locking to the eyelet (not shown). As illustrated at FIG. 85B, device 670 can be disposed to place a small tube 675 over the mesh allowing for the tensioning to vary. Depending on the structure of the locking eyelet and the polymeric rod or mesh portion, increasing tension can be fairly easy, while decreasing tension may be difficult. Tube 675 covers mesh portion 674 and rod 672 to interfere with frictional engagement between mesh portion 674 and rod 672, and a locking eyelet (or other frictional adjustment surface). By preventing frictional engagement between those surfaces, tube 675 permits the tensioning to be adjusted (increased or decreased) until the desired point has been reached. Then the tube can be pulled off the mesh (by pull tab 678) to expose the mesh to the eyelet and secure the position of the eyelet relative to the mesh.

Figure 86A:
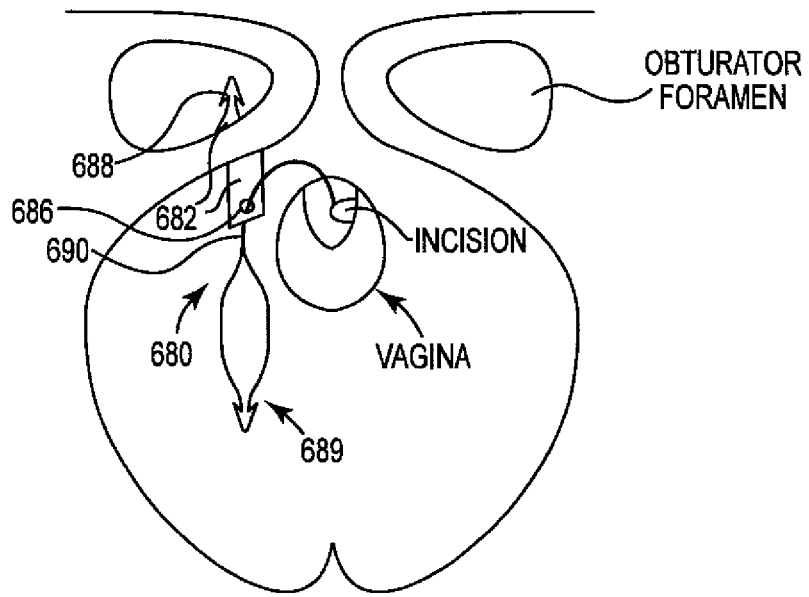
FIGS. 86-87 depict a levator support device in accordance with embodiments of described inventions.
Figures 86B, 86C:
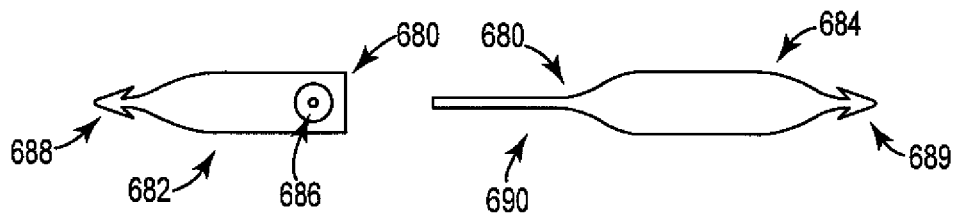

Referring to FIGS. 86A through 86C, methods and devices for permitting a levator ani support through a vaginal incision, as a separate procedure or optionally in combination with tie in with a pelvic procedure as described herein such as a transvaginal mesh repairs. Implant 680 includes a first (anterior) implant 682 and a second (posterior) implant 684. Anterior implant 682 includes an anchor 688 for placement at an obturator foramen, and an eyelet 686. Posterior implant 684 includes an anchor 689 for placement into levator ani muscle, and an extension 690, such as a polymeric rod. The anchors may be any conventional anchor or an anchor as described herein. After placement of the two anchors 688 and 689, tensioning can be accomplished by advancing a portion of posterior implant 684 through eyelet 686, starting with extension 690. The anterior anchor 688 can be placed by any known or developed method, such as by use of a conventional anterior needle. The levator floor anchor 689 location can be placed with a similar type of conventional or developed posterior needle. Then tensioning can be completed by passing extension 690 of implant 684, attached to the pelvic floor, through eyelet 686 of implant 682, attached at the obturator foramen, then adjusting.

Figure 87A:
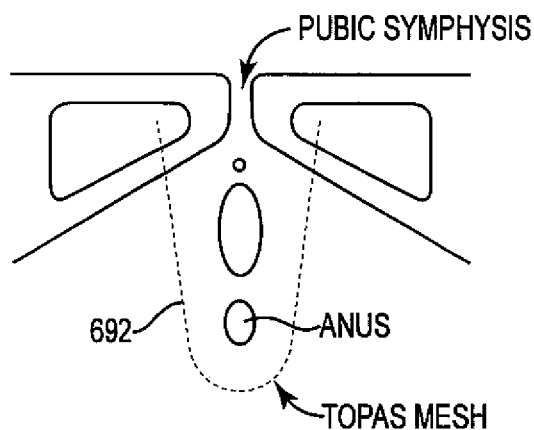
Figure 87B:
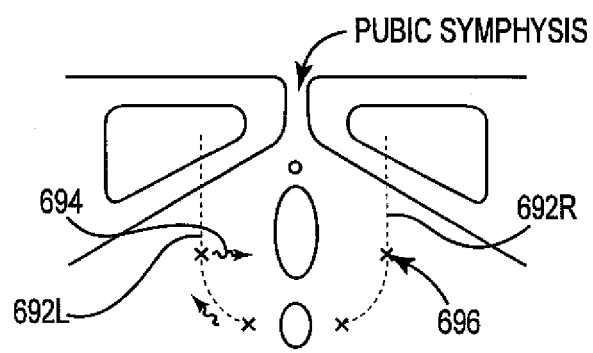

Implants as described herein, for supporting pelvic tissue, can be useful in conjunction with other methods of treating pelvic conditions, such as treating a levator hiatus, anal incontinence, etc. FIG. 87A shows a transvaginal method of treating anal incontinence, or a hiatus, by placing a sling 692 to support an anal sphincter, and attaching the two ends of the sling to anterior locations, such as to each of the right and left obturator foramen. According to FIG. 87B, this method can be improved by using a two slings 692L and 692R (e.g., elongate mesh strips), each attached at an anterior end to an obturator foramen and at a posterior end at a region of a rectum or a sacral anatomy. Each of slings 692L and 692R may optionally include additional means to support a pelvic floor or adjust tension, such as by one or more anchoring feature, or alternately a tension adjusting feature (one on each of the left and right side of the patient) to separately adjust the length or tension the right side and the left side. Referring to FIG. 87B, an anchor 694 can be connected to or extended from either sling 692R or 692L along the length of the sling, which is positioned in an anterior-posterior orientation along a right side or left side of a patient. The anchor 694 can connect the sling 692L or 692R and secured to tissue of a levator, to support the levator. Optional tensioner 696 can be located at a position long a length of a sling 692L or 692R, and can be any of the different tensioners or length-adjusting features described herein or elsewhere. After distal and proximal anchors are placed and a length of a sling 692L or 692R is generally determined, tensioner 696 can be adjusted to provide optimal length and tension of the sling.

The implants and tools are comprised of conventional materials. For example, the mesh can be constructed of polymer materials, such as a thin film or sheet material of polypropylene, polyethylene, fluoropolymers or like compatible materials, both permanent and absorbable.

Various embodiments herein are advantageous because they facilitate reduction of total procedural time if the patient needs a urinary sling, levator floor support, high apical support (fixation to the sacrum), and anterior or posterior prolapse by combining multiple products into one. The pelvic floor support reduces the long term prolapse recurrence as well as improve the patient's sexual function with the high apical support due to the sacral fixation. Moreover, the various tools and methods allow a physician to use a transvaginal approach and achieve a similar tension as what is currently only achievable in a abdominal or laparoscopic approach to the Sacrocolpopexy procedure.

Various implants or systems, features and methods are envisioned for use with the present invention, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382. Accordingly, the above-identified disclosures are fully incorporated herein by reference in their entirety.

Referring generally to FIGS. 100 through 110, various embodiments of tools or systems and methods are shown, specifically involving expansion members (e.g., tubes, retractors, etc.) as also described hereinabove, and variations, derivatives, or modifications of those devices. The following expansion member features and structural embodiments can be derivatives, modifications, or variations of the expansion devices (e.g., tubes, retractors, etc.) that are described and illustrated hereinabove, and as such the descriptions of features of those expansion device embodiments applies to these (following) expansion device embodiments as well; for example, any combination of the structural dimensions features (length, diameter, etc.) and optional functionality features described above for expansion devices can be applied to the following multi-functional tools.

Various portions of a system 710 can be constructed of polymer materials, metal, or other biocompatible or acceptable surgical apparatus materials. Various tissue retractors for use in a transvaginal SCP procedure are generally disclosed in FIGS. 100-110.

Figure 88:
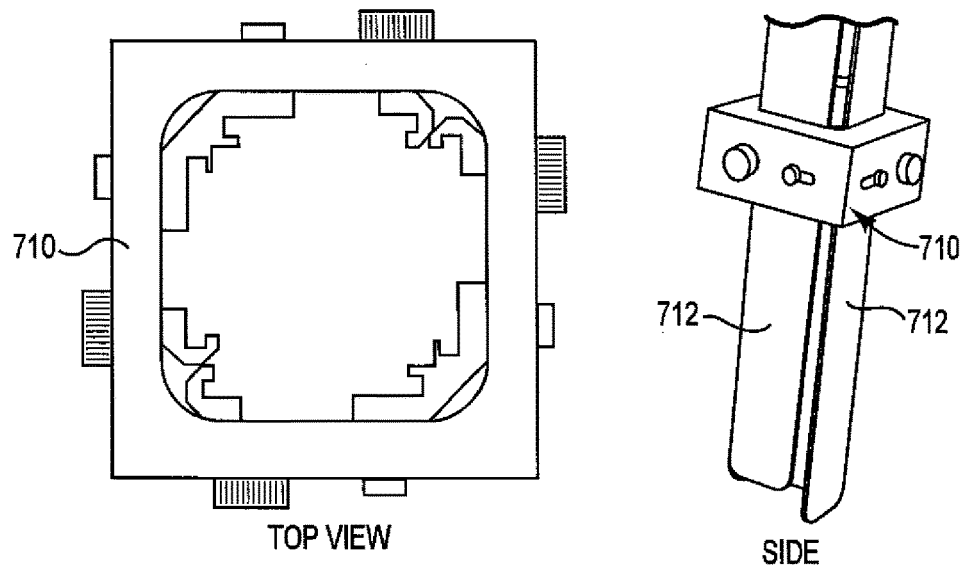
FIGS. 88-97 depict various embodiments of surgical retractor tools, systems or components in accordance with embodiments of described inventions.

FIG. 88 shows a refractor with docking stations for malleable tissue retractors (i.e., malleable refractor arms or spreader features) (see FIG. 27 and related text). As shown in the top view, retractor system 710 includes two fixed corners with features that hold one end of a malleable retractor arm 712 (long flat rectangular piece of malleable plastic or metal such as stainless steel). The other two corners have mobile features that clamp onto the malleable retractor arm. This allows the operator to advance and manipulate each refractor individually.

Figure 89:
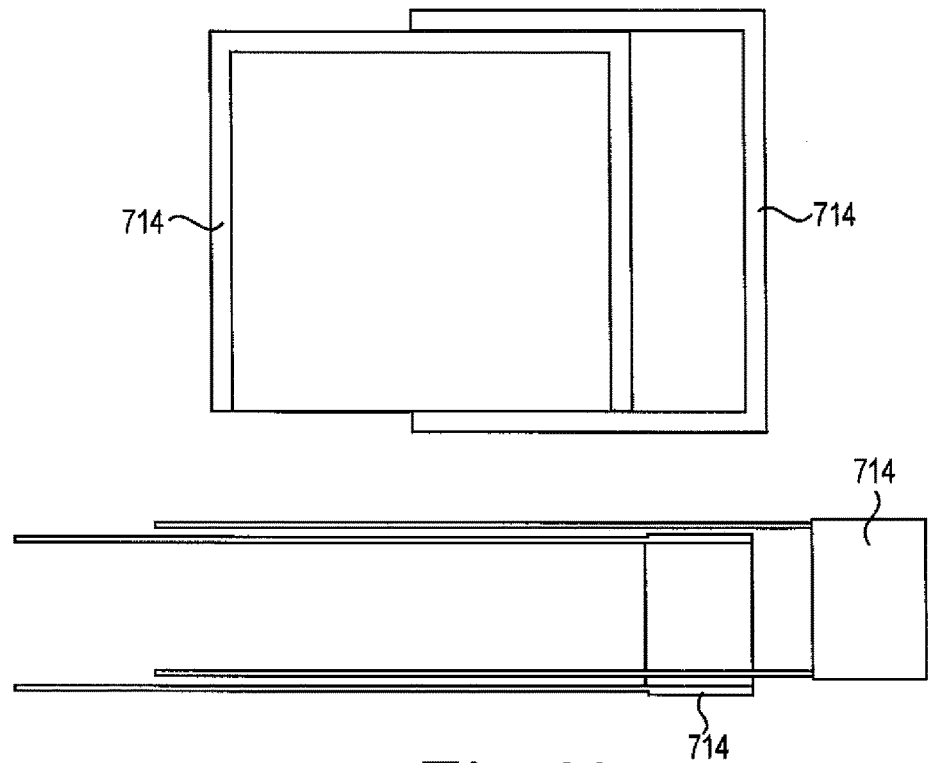

FIG. 89 shows a system 710 with a C-shaped frame 714 to hold and maintain a position of retractor arms 712. The C-shaped from reduces the overall profile of the previous square retractor frame and removes one wall from the frame for additional access. In addition, the profile is shaped to fit inside of itself so a retractor could be moved, removed, or advanced individual of the second retractor.

Figure 90:
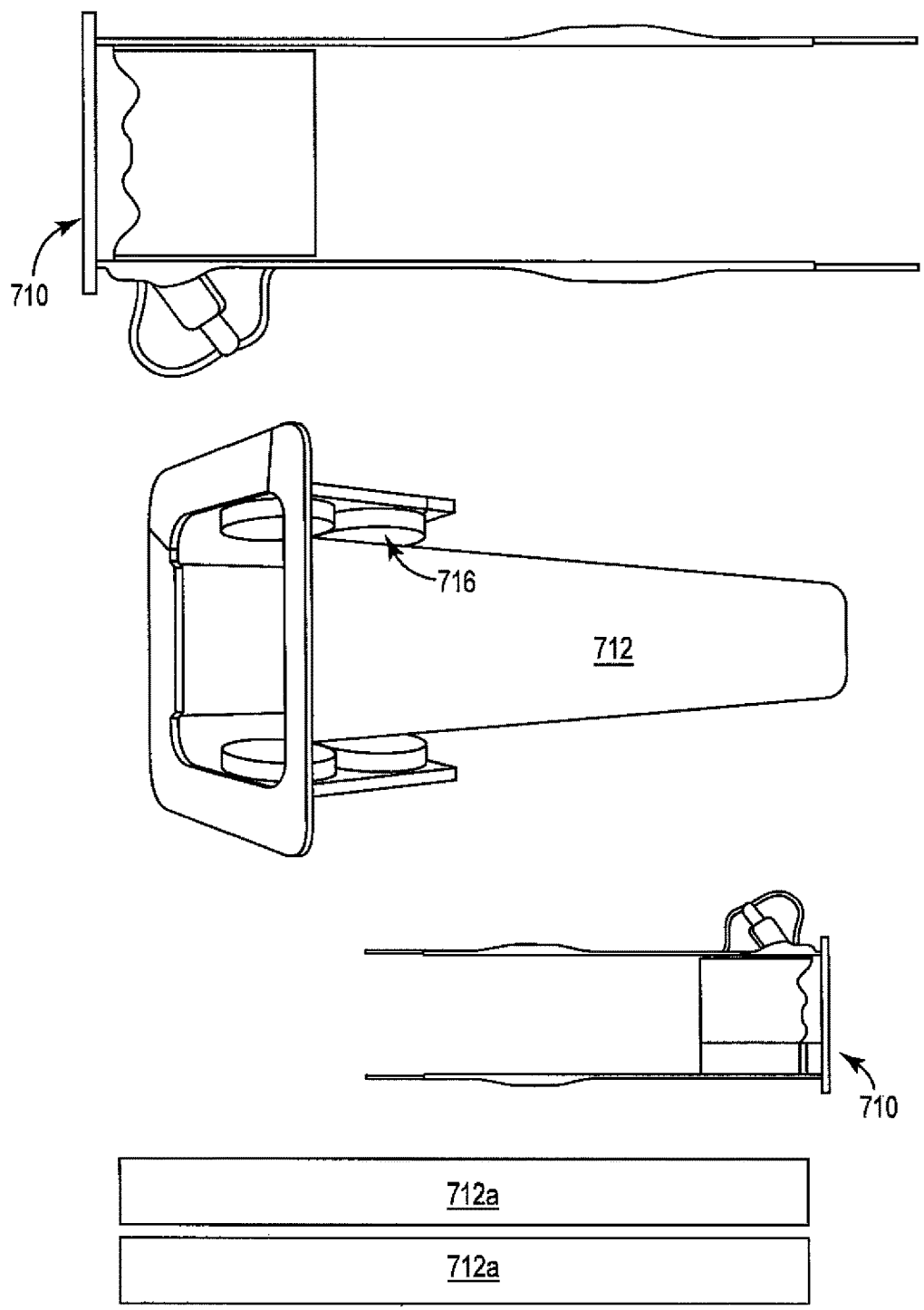

FIG. 90 shows a retractor system 710 with docking stations that use magnets 716 to engage one or more magnetic retractor arms 712*a*. This is a similar concept to that in FIG. 100. The mechanical structure normally used to clamp tissue retractor arms 712 to a proximal frame of system 700, are replaced with magnets 716 and magnetic materials that engage a proximal end of arms 712*a* during a surgical procedure.

Figure 91:
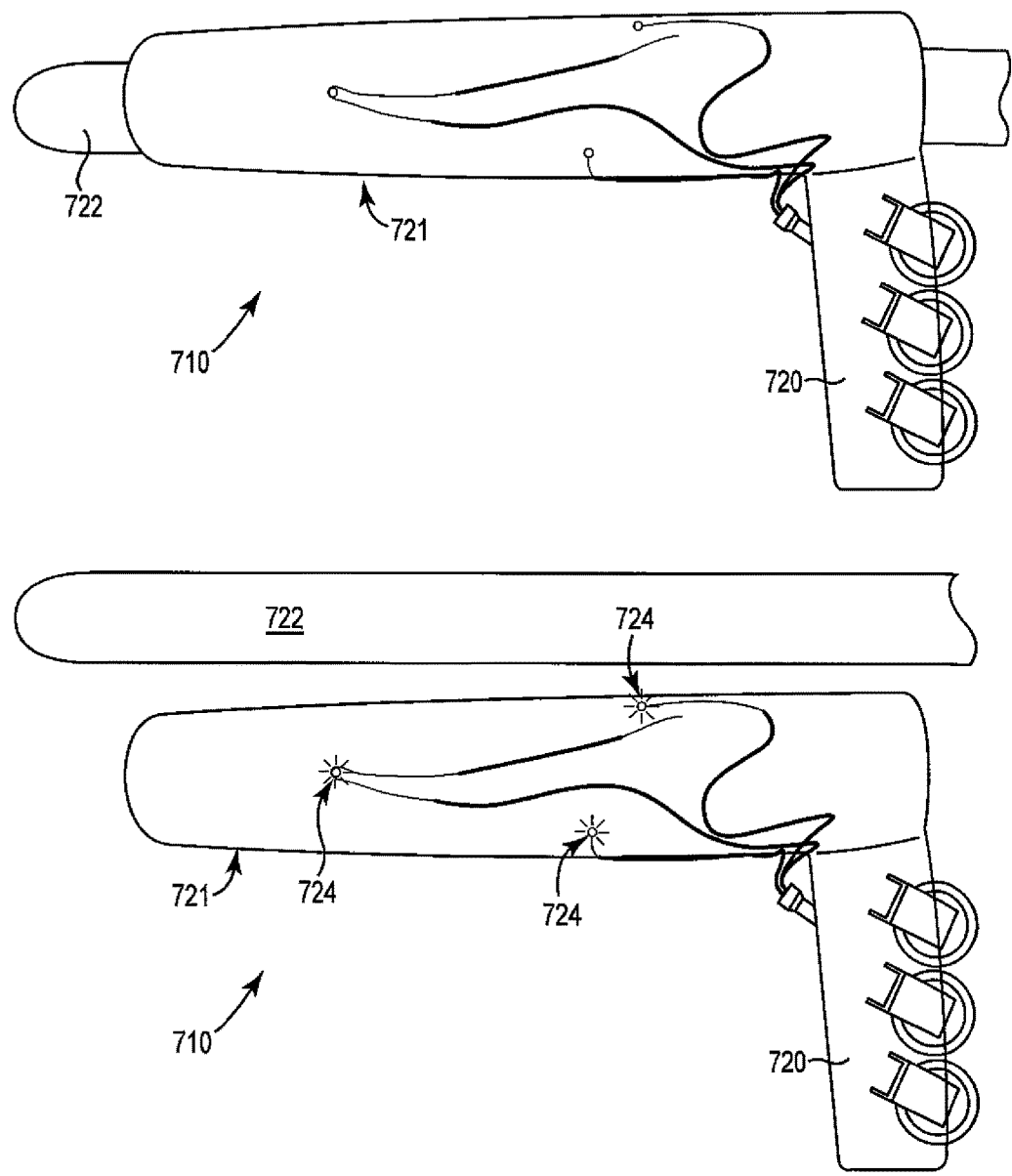

FIG. 91 shows a round retractor with retractor shaft 721, handle 720, lights 724, and introducer 722 (which fits into an internal channel of retractor shaft 721). Introducer 722 functions as a guide for the retractor shaft 721. Once a surgical dissection (e.g., transvaginal) is completed to a point where the retractor is necessary, the introducer 722 can be inserted to a targeted location. The retractor shaft can be placed over the top of the introducer 722 until the target tissue is reached. Lights 724 add additional assistance for visibility. Lights 724 can be fiber optic, LED, LCD, or any other means of generating or conduct light to be emitted from light locations 724. Optionally and as illustrated, shaft 724 can be transparent, or include a lens, to allow light to be transmitted and directed as desired.

Figure 92A:
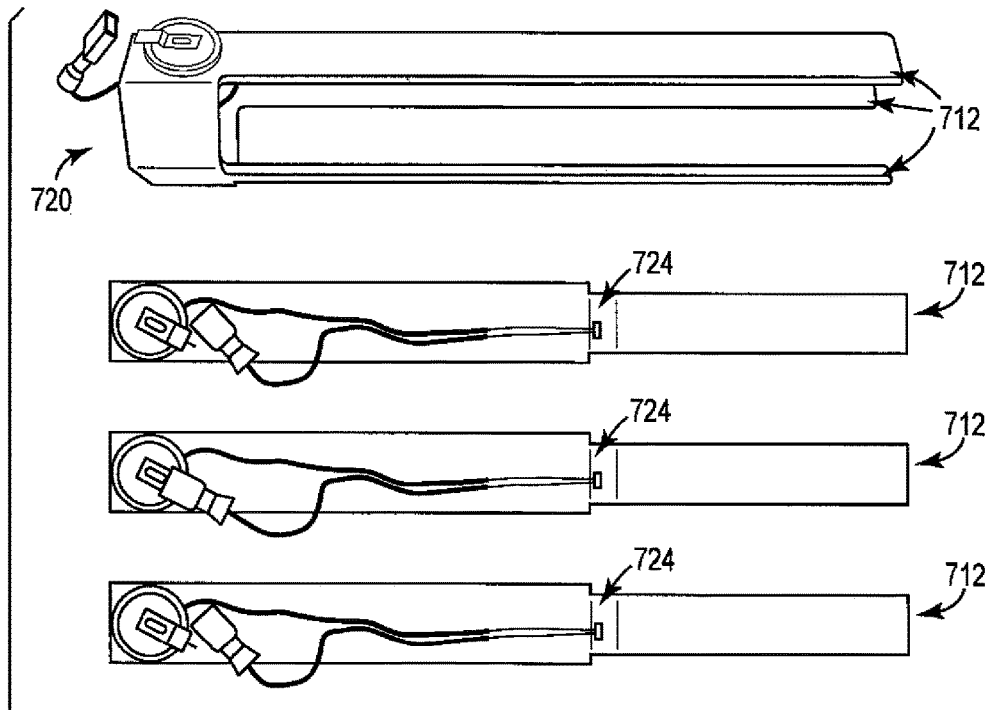
Figure 92B:
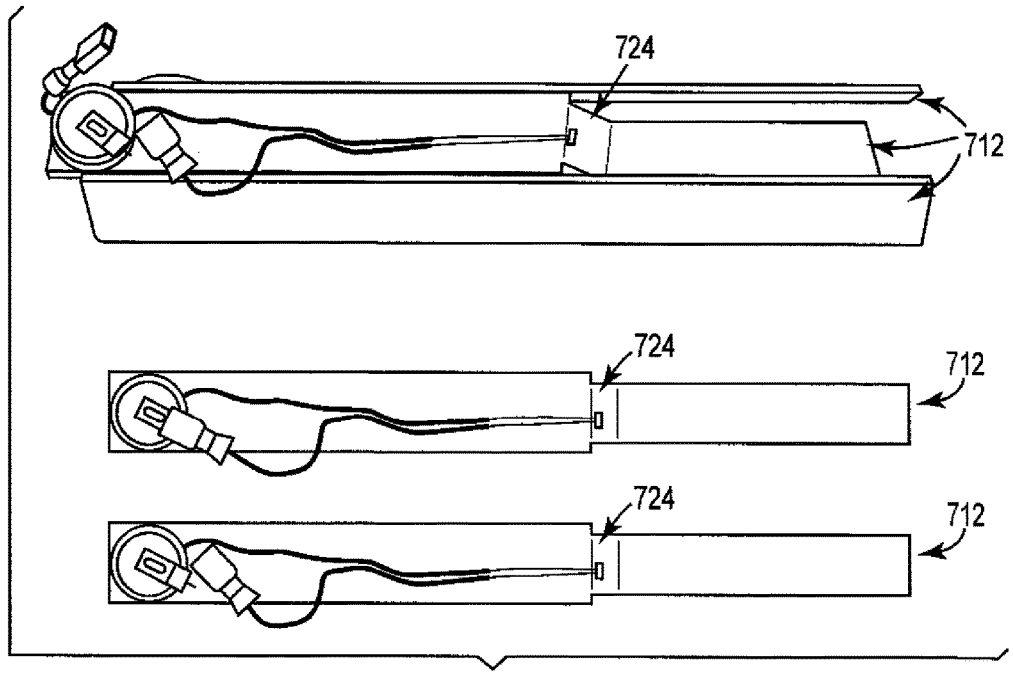

FIGS. 92A and 92B show a collapsible retractor system 710 (as generally described elsewhere herein) with separable or foldable retractor arms 712 for tissue separation and tissue mobility. This retractor system 712 ultimately forms a hexagon when assembled and secured by framing at a proximal end. The retractor system 710 has 3 arms (712) and 3 individual retractor segments. The retractor system 710 with 3 arms 712 is introduced in a non-assembled or folded configuration, then the individual retractors can be unfolded or otherwise assembled while arms 712 are internal to a patient. The pieces can be assembled and interlocked at the main unit (proximal frame). The individual retractor arms 712 allow for tissue to be moved or manipulated while being placed and assembled. To complete the assembly, individual retractor arms 712 lock into place at the proximal end, to prevent collapse. Optionally, system 710 at FIGS. 92A and 92B can include lights 724, which can be fiber optic, LED, LCD, or any other means of generating or conduct light to be emitted from desired light locations. Optionally and as illustrated, arms 712 can be transparent, or include a lens, to allow light to be transmitted and directed as desired. Also optionally, system 710 at FIGS. 92A and 92B can include magnetic engagements for magnetically holding arms 712 at a desired location relative to a proximal frame.

Figure 93A:
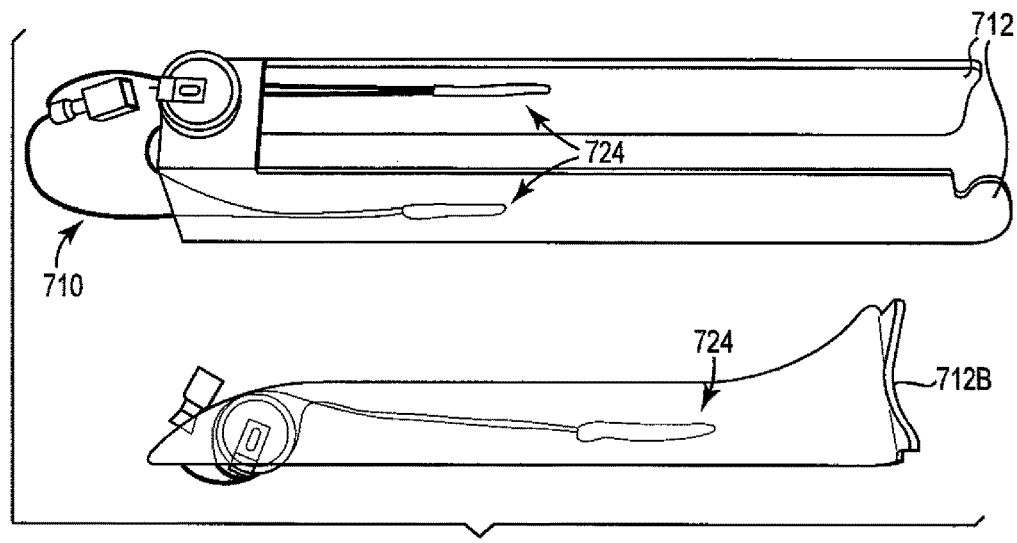
Figure 93B:
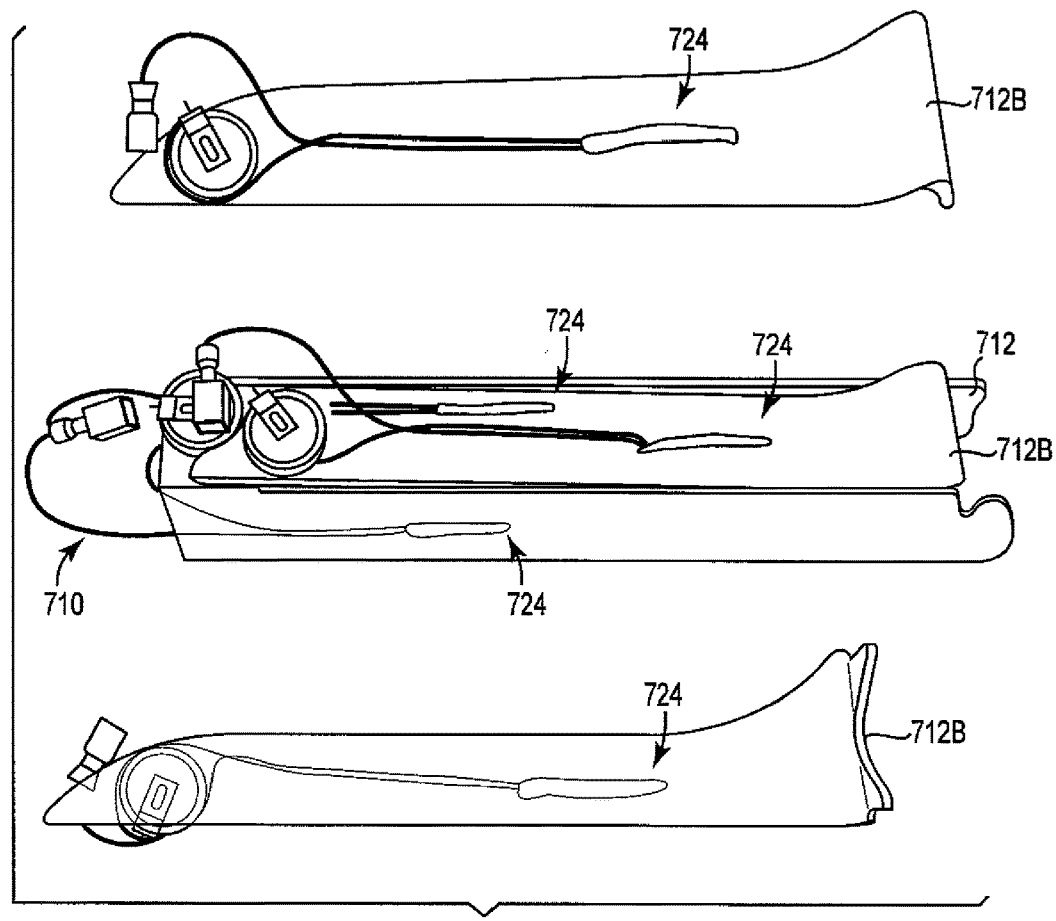

FIGS. 93A and 93B show additional versions of a foldable or collapsible retractor system 710, with separate retractor pieces and retractor arms 712 to hold open a surgical incision. System 710 includes four arms 712, which can include various distal end structures to spread tissue. System 710 of FIGS. 93A and 93B are similar to those of FIG. 92, except that the system of FIG. 93 includes two arms, instead of three as in FIG. 92. In addition, two optional small supports (arms 712B) are configured to slide down the length of retractor arms 712, to help keep the retractor open (preventing collapse). Optionally, system 710 at FIGS. 93A and 93B can include lights 724, which can be fiber optic, LED, LCD, or any other means of generating or conduct light to be emitted from desired light locations. Optionally and as illustrated, arms 712 can be transparent, or include a lens, to allow light to be transmitted and directed as desired. Also optionally, system 710 at FIGS. 93A and 93B can include magnetic engagements for magnetically holding arms 712 at a desired location relative to a proximal frame.

Figure 94A:
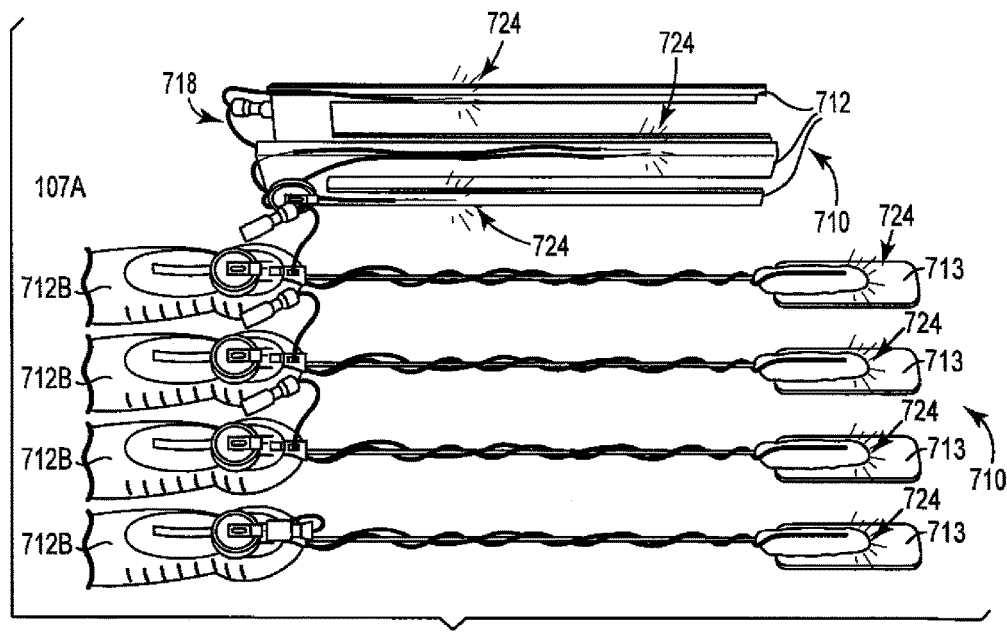
Figure 94B:
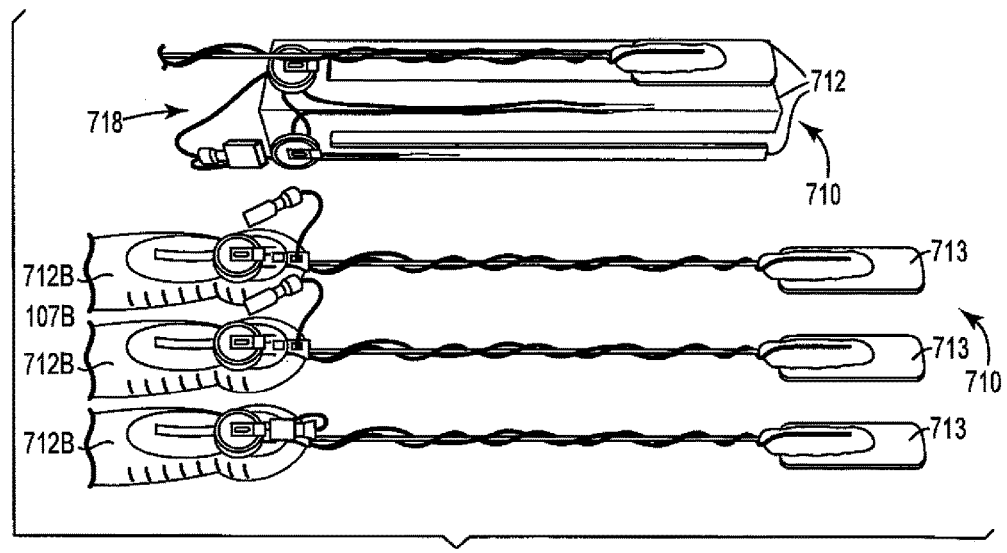

FIGS. 94A and 107B show a collapsible retractor system 700 with separate retractors for tissue mobility, in assembled and non-assembled forms. This is similar to the system of FIGS. 92A and 92B, except that system 700 of FIGS. 94A and 94B includes four individual retractor arms 712 instead of three as in FIGS. 92A and 92B. The main retractor frame (718) houses the four corners (arms 712) while each of separate retractor arms 712B with distal paddles 713 can work inside to move tissue and then snap into place on the main retractor (frame at a proximal end) to hold back tissue as well as to hold the retractor open (preventing collapse). Optionally, system 710 at FIGS. 94A and 94B can include lights 724, which can be fiber optic, LED, LCD, or any other means of generating or conduct light to be emitted from desired light locations.

Figure 95:
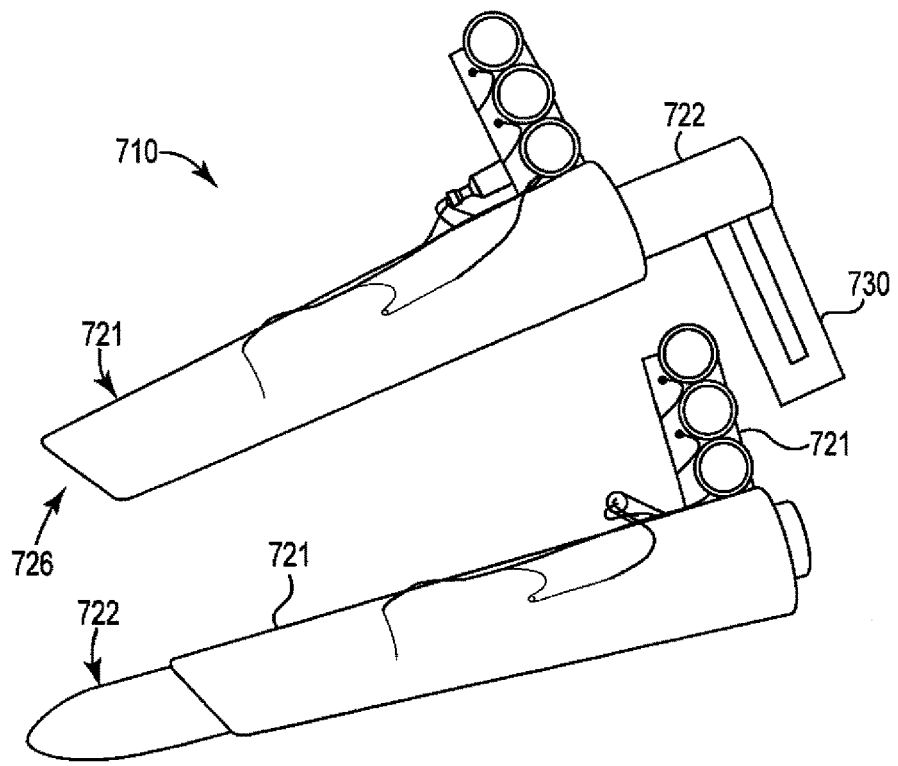

FIG. 95 shows a round retractor with retractor shaft 721, retractor handle 720, lights (not shown), introducer 722 (which fits into an internal channel of retractor shaft 721), and introducer handle 721. System 710 of FIG. 95 is similar to system 710 of FIG. 104 but additionally includes a slanted distal opening surface 726 of shaft 721, so the distal opening of shaft 721 matches a slant, curvature, or orientation of the sacrum when retractor shaft 721 is placed transvaginally to place slanted distal opening of shaft 721 to access a region of sacral anatomy. System 710 of FIG. 95 is similar to system 710 at FIG. 104, except that introducer 722 has a handle 720 for extra security, and the tip of shaft 721 is slanted to match the shape and posture of the sacrum, for improved visualization. Lights (724) are not identified at FIG. 95.

Figure 96:
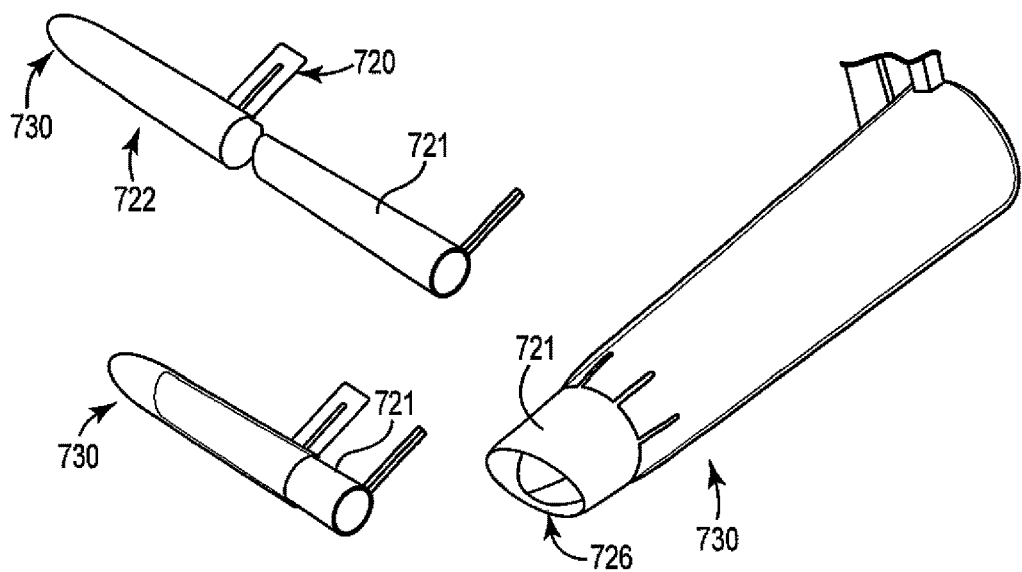

FIG. 96 shows a round introducer 722 with an expandable distal end or tip 730. This is similar system 710 of FIG. 91 except that the introducer 722 is placed outside of shaft 721, instead of inside. Introducer 722 is introduced first with the expandable nose cone 730 creating a path through tissue. Then, a second component (shaft 721) can be inserted into the inner diameter of introducer 722, to open the nose cone, creating a working space, and locking open the cone. As illustrated, shaft 721 can include a slanted distal opening surface 726, so the distal opening 726 of shaft 721 matches a slant, curvature, or orientation of the sacrum when retractor shaft 721 is placed transvaginally to place slanted distal opening 726 f shaft 721 to access a region of sacral anatomy.

Figure 97A:
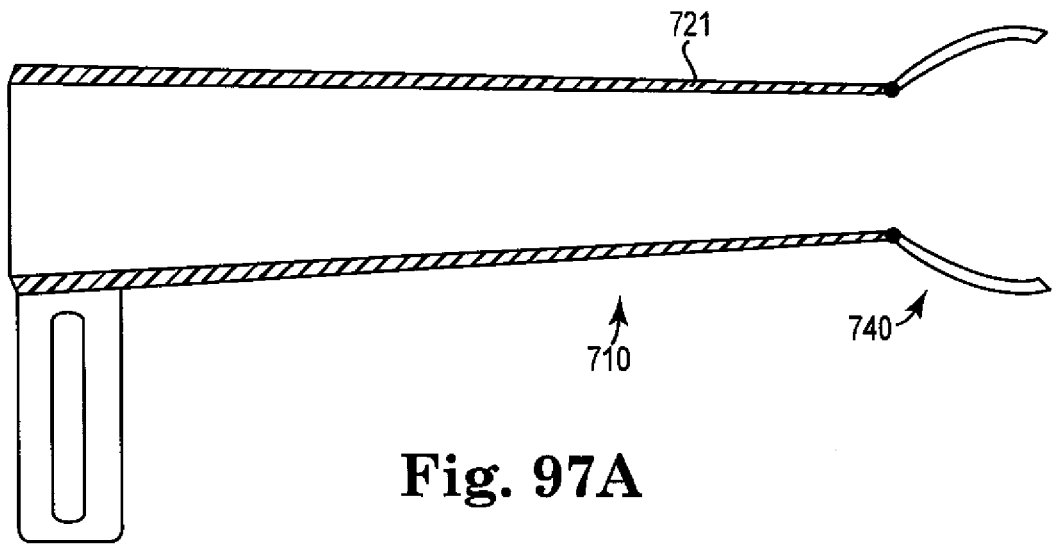
Figure 97B:
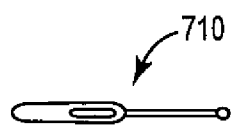
Figure 97C:
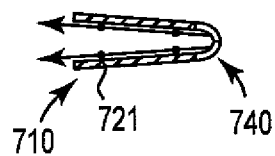

FIG. 97 shows a round refractor with a flexible tip that expands or opens, at the distal end of a refractor shaft 721, by manipulation of an actuator (not shown) at a proximal end. This is similar system 710 of FIG. 96 except the inner component (introducer 721) is not necessary. A separate mechanism opens the distal portion 740 of the retractor shaft 721, to create a working space at desired pelvic anatomy (i.e., a region of sacral anatomy when shaft 721 is placed transvaginally). A small lever or cable can be used to open tip 740 and then an "over center" mechanical lock can keep the tip open without any addition assistance. FIGS. 97B and 97C shown retractor system 710 with distal portion 740 in a closed configuration, for insertion. After insertion transvaginally in this closed configuration, distal portion 740 can be opened as shown at FIG. 97A.

Some potential advantages to the system embodiments of FIGS. 100-110 include that each refractor provides a different method, device, or technique to enhance visibility and operation. As such, time for a pelvic treatment procedure (e.g., SCP procedure) can be reduced through ease of use and direct visualization. Various structures, device, components or portions of the embodiments of FIGS. 100-100 can be constructed of polypropylene, polycarbonate, stainless steel, steel, magnets, epoxy, adhesive, LED, filament bulbs, or other materials or devices known to those of ordinary skill in the art for application given the disclosure provided herein.

FIGS. 98 through 114 show various surgical dissection tools or systems 820, including those adapted for use with known or modified introducer needles. These tools or systems 820 allow for dissection and placement of an implant (e.g., mesh) during a pelvic (e.g., prolapse) repair procedure, including those described herein. The systems 820 allow a physician to access a desired surgical location for surgical implant placement (e.g., a region of sacral anatomy by a transvaginal incision), while integrating features of various tools into one device that is specifically adapted to allow proper dissection for surgical application and for teaching physicians how and where to place mesh that will promote better patient outcomes and recovery. The following tool embodiments and systems can be derivatives, modifications, or variations of the multi-functional tools described and illustrated hereinabove, and as such the descriptions of features of those multi-functional tool embodiments applies to these (following) tools as well; for example, any combination of the structural dimensions features (length, diameter, etc.) and optional functionality features described above for multi-functional tools can be applied to the following multi-functional tools. Any of the previously-described and the following multi-functional tools, such as a two-in-one tool, can allow a physicians to identify a proper depth of tissue to dissect, and an incision of the tissue that will be more precise with minimal blood loss. Proper dissection through a vagina to a vesicovaginal space is very important and has been recognized by physicians as a area of importance in performing procedures such as those pelvic treatment procedures described herein.

Anatomical spaces for such procedures are largely avascular and proper dissection will minimize excessive bleeding and subsequent hemotoma. By laying a mesh implant exteriorly to the vaginal visceral connective tissue capsule, the incidence of mesh erosion and extrusion is minimized. The disclosed systems and tools 820 provide improved methods and systems for a physician to properly dissect down to necessary tissue planes with a disposable device.

Certain advantages to these systems and methods may include: 1) reduce risk of erosion or extrusion of mesh by placing mesh in the proper location; 2) ability of a physician to place a needle first to determine a proper depth for tissue incision before slicing delicate vaginal tissue; 3) reduced blood loss; 4) the use of the device or system can teach a physician the proper tissue dissection for mesh placement and make that dissection easier; 5) provide confidence for physicians that dissection is being done with the lease trauma with confirmation that the correct anatomical compartment is being identified for mesh placement; 6) potential faster learning curve for physicians to safely dissect tissue; 7) potential applications in other areas of medicine such as laparoscopic port placement currently served by the Veress needle or Hassan introducer.

Systems, devices, or components thereof can be constructed of rigid biocompatible materials such as stainless steel. Other known or compatible materials are also envisioned for constructing any or all of the systems, devices or components. The needle could be small in diameter but provided with enough rigidity to allow safe passage through the vaginal tissue, and provided with the potential for cutting the vaginal tissue orthogonal to the needle. Further, the needle could be provided with other features, including features that would promote dissection of tissue with fluid, gas, an expandable balloon, or a mechanical dissector or other feature that could be deployed within the tissue planes to dissect tissue. In addition, the needle could have features that would allow the physician to safely cut down the vaginal tissue with a scalpel or other instrument to allow safe dissection of the tissue.

Figure 98:
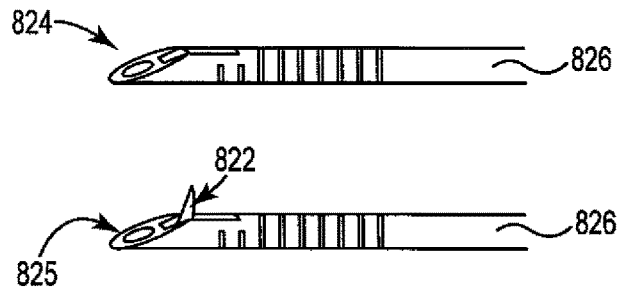

FIG. 98 shows a hydro-dissection needle 820 with a separate, retractable, mechanical cutting element (e.g., blade) 822. The illustrated needle, with shaft 826 and tip 824, includes hydrodissection functionality at tip 824 including a port 825 for fluid inflow to hydrodissect tissue. Optional depth marks can be included to recognize a depth of placement of tip 824 during a procedure. Cutting element 822 can be a mechanical element such as a retractable blade, or another type of non-mechanical cutting element (ultrasonic, cauterization, heat, etc.) separate from the hydrodissection functionality. During use, shaft 826 can be advanced to place tip 824 at a desired tissue plane, and fluid is inflated into the needle to create a dissected pocket. A cutting element 822 can be (optionally extended) and used to cut through vaginal tissue to develop an incision. The needle shaft 826 can include depth marks or indicia to provide visualization and/or ultrasound visualization.

Figure 99:
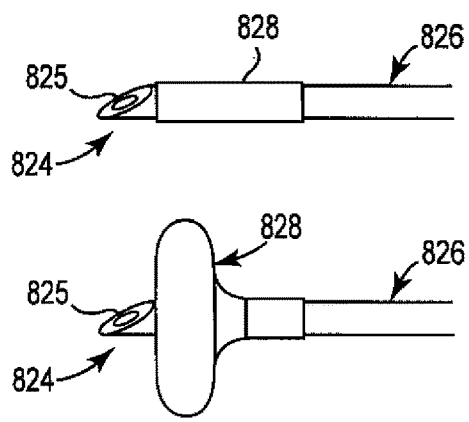

FIG. 99 shows a similar hydro-dissection needle 820 that includes inflatable balloon 828. Needle 820 can be advanced to a proper tissue plane for dissection of vaginal tissue. Needle 820 is used to inflate tissue using saline or other fluids with a syringe or like device (e.g., through a fluid port (not shown) at tip 824). As a tissue plane is developed, a second syringe can inflate balloon 828 to develop the tissue plane to a greater degree. The balloon can be shaped to dissect tissue in a circular or oblong manner. Dissection can be performed by a hydrodissection functionality at tip 825, alternately by a retractable cutting element 822 (not shown), or by any other dissection means or method.

Figure 100:
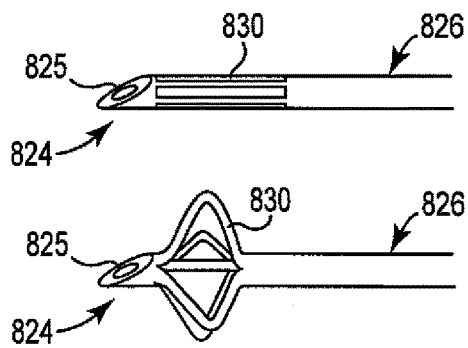
Figure 100B:
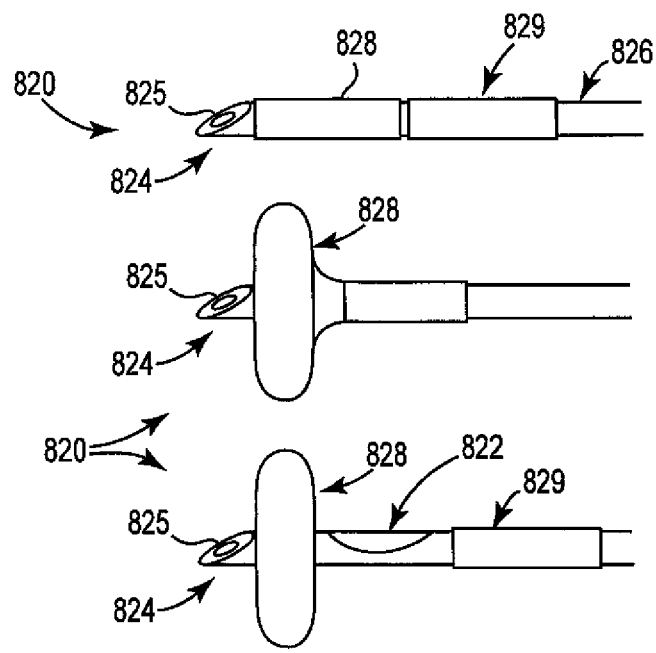

FIG. 100 shows a hydro-dissection needle 820 that is similar to the needle 820 at FIG. 99, with a mechanical dissection means or device (830) as a substitute for balloon 828. Mechanical means 830 can be any mechanical substitute for an inflatable balloon (828) such as an expandable mechanical cage or mechanical arms that extend from shaft 826 to contact and displace tissue laterally. This is similar to the needles 820 described above at FIGS. 98 and 112, with mechanical arms deployable to develop the space for further safe incising of the vaginal tissue.

FIG. 100A shows a hydro-dissection needle 820 with a balloon 828, a retractable cutting element 822, and a retractable sheath 829 that can cover and uncover cutting element 822. The needle can be used to hydro-dissect as described above, with the dissection developed further with the use of a balloon. When the physician is ready to incise the tissue, a sheath is retracted to expose a cutting element to cut the tissue.

Optionally, while not illustrated, any of the hydro-dissection needles 820 described herein can include an integrated scope, optional steering functionality at the distal end, imaging and lighting functionalities, etc. For instance, a transvaginal SCP scope needle design could be applied.

Figure 101:
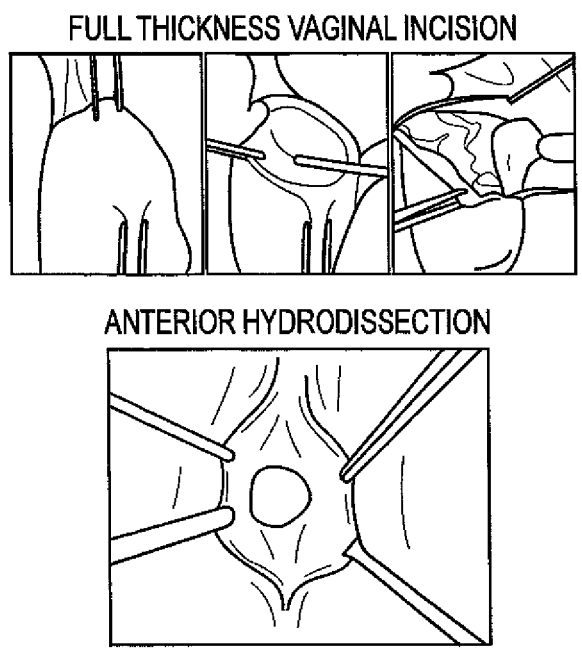
Figure 106:
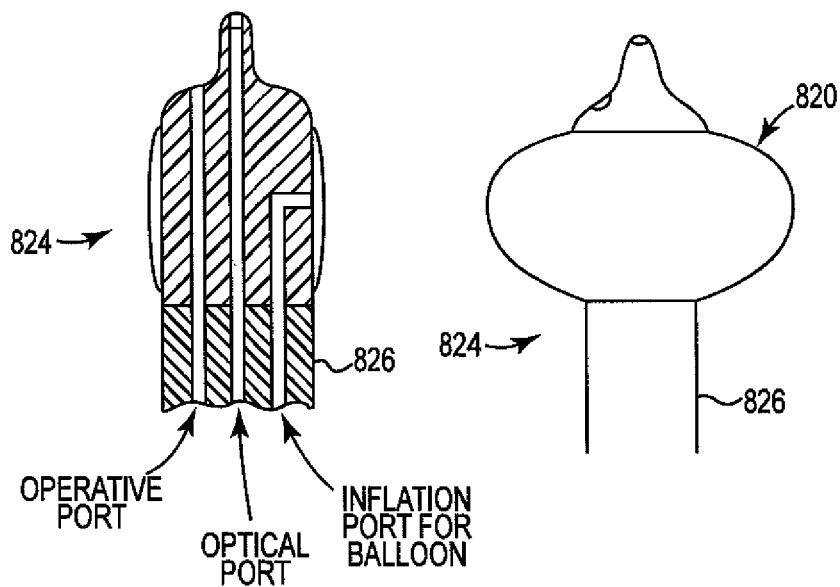
Figure 107:
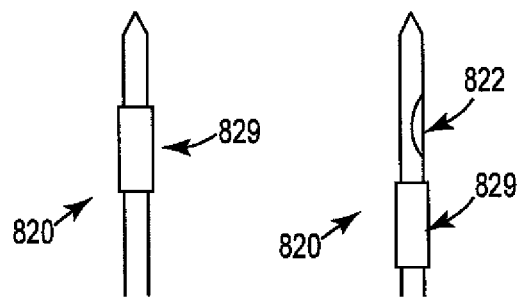

FIG. 101 shows features of one technique that can be used, with a needle 820, to dissect vaginal tissue to improve the ability of physicians to perform the described procedures, providing lower erosion rates, avoiding the vaginal apex, teaching proper techniques, etc.

FIGS. 102 through 108 show embodiments of transvaginal SCP scope needles (i.e., needles having a viewing functionality and distal end steering functionality as described hereinabove) 820 to promote completion of a transvaginal SCP procedure safely through a minimal vaginal incision. As such, no abdominal wounds are required, and potential organ perforation or dissection are avoided to allow for a less invasive surgical option for physicians to treat patients.

Certain advantages to these needles (820), systems and methods are: 1) clear visualization of the needle passage for safe anchoring at the sacrum; 2) ability of the physician to guide the needle and identify potential areas of risk and steer the needle to the proper target anchor site; 3) provide confidence in proper needle passage for a physician not as familiar with the anatomical structures or uncomfortable guiding the needle by "feel"; 4) potential faster learning curve for physicians to safely pass the needle and draws upon other experiences they may have with scopes; 5) potential applications of the scope needle in other areas of medicine.

Alternate embodiments of the present invention may include a needle 820 configured for passage through any area of the body to safely guide (under direct vision) the needle 820 through tissue. The needle 820 is generally any multi-functional tool as described hereinabove, that may include a cutting element at the tip to allow easier passage of a needle tip (824) through tissue, or a cutting element along the needle (shaft 826) length that could optionally be exposed (extended) to slice through the tissue laterally after passage of the needle to a proper depth. The needle 820 could have depth markers along the (shaft 826) length to indicate to the user the exact depth the needle has been passed. The needle tip 824 could have a lumen to pass fluid to hydro-dissect the tissue as tip 824 is passed through tissue. The lumen to pass fluid could be directed at a lens of the scope to clean off the lens as it is passed through the tissue. The needle tip or distal end could have a balloon around it that could be inflated to dissect or distend a body cavity into which the needle distal end has passed. The needle tip or distal end could have an open channel for delivery of an anchor or passage of a suture to allow anchoring or suturing to an anatomical structure.

In general, embodiments of a needle 820 could be constructed of a rigid biocompatible material such as stainless steel or a similar metal or plastic material having a high strength and a high modulus of elasticity. Other constructs and materials are also envisioned for use with embodiments of a needle 820. The needle could further be small in diameter (similar to the Sparc® product sold by American Medical Systems of Minnetonka, Minn.) but with enough rigidity to allow safe passage to a specific anatomical site or structure.

As discussed with the multi-functional tools hereinabove, one or both of an optional fiber optic light source and fiber optic image bundle can be integrated into needle 820. In addition, a needle 820 could have features or devices that would allow delivery of a tissue anchor, a suture, a surgical mesh, a fluid, an expandable balloon, a mechanical dissector, a hook, a stent or other features or devices to anchor or fixate to a tissue structure within the body. The balloon, mechanical dissector, or fluid could be used to allow dissection of remote tissues under visualization to carry on a surgical procedure in the body. The needle 820 could have sufficient rigidity to allow the physician to steer the device or system safely under direct vision to the proper location within the body; alternately or additionally, a distal end may include a steering functionality that can be controlled from a proximal end of the needle 820.

FIG. 102 shows a needle assembly 820 having optical fiber inside (extending along a length of shaft 826 to tip 824), depth marks on shaft 826, and other device components such as handle, needle tip 824, fiber optic imaging and light bundle and connections thereto at the proximal end, and the like.

FIGS. 103 through 107 show various needle tip 824 configurations adapted for use with a needle 820. These needle tip embodiments include combinations of features that include one or more working channel (for any one or more of fluid delivery, delivery and manipulation of an anchor through tip 824, passage of a cutting element to and through tip 824, or any other useful purpose), optical channel, lenses, sheaths, balloons, a flow port (for passage or collection of fluid), cutting blades, and the like.

Figure 108:
FIG. 108 depicts an optical needle system for vaginal delivery of anchors to the sacrum through visual means or devices, in accordance with embodiments of described inventions.

FIG. 108 shows an exemplary optical needle system for vaginal delivery of anchors to the sacrum (i.e., a region of sacral anatomy such as an anterior longitudinal ligament) through visual means or devices to allow support of the vaginal cuff. For instance, a gas or liquid line can be provided to inflate tissue areas for visualization, flushing, hydro-dissection, or an combination of these. A camera and light source can also be provided in operative communication with the optical needle device, shaft 826, and tip 824.

FIGS. 109 through 116 show various anchors, systems, and methods for facilitating or performing sacral tissue fixation (i.e., fixation of an implant to a region of sacral anatomy). In a SCP procedure, fixation to the sacrum is a useful feature of the procedure, allowing for immediate apical support of the vagina once the surgery has been completed. The following embodiments of fixation devices (anchors) and methods generally provide a one-handed operation that can securely fixate an anchor and associated implant (e.g., mesh) to a sacrum, and uses the strength of the anterior longitudinal ligament for the retention strength instead of a bone.

Figure 109:
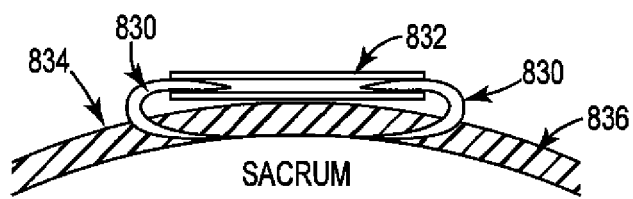
Figure 110:
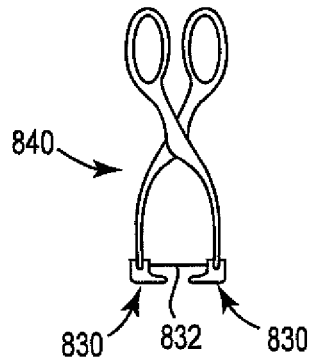

The embodiment illustrated at FIGS. 109 and 110 include re-positionable anchors that include two opposing hooks 830 held together by springs or polymer 832, used to secure an implant (e.g., mesh) 834 to a region of sacral anatomy such as an anterior longitudinal ligament 836. To initially place these anchor structures, the distance between the opposing hooks 830 is increased by stretching tubing or spring 832, e.g., using a pliers or other installation device, e.g., a multi-functional tool such as a needle 820 as described herein, capable of reaching transvaginally to a region of sacral anatomy. Then the hooks 830 are introduced to a surface of ligament tissue 836 and hooks 830 can be are pushed together to secure a strong hold on ligament 836, also securing implant 834 to ligament 836. The springs (or polymer) ensure that the hooks maintain a hold on ligament 836 and mesh 843. If initial placement of the anchor is not as desired, the anchor can be removed by using the same placement tool and stretching hooks 830 apart, re-positioning the anchor at a different tissue location, and releasing the anchor so hooks 830 enter tissue at that different tissue location. FIG. 110 shows a pliers 840 that can be used to engage hooks 830 of an anchor, pull hooks 830 apart to stretch spring or polymer 832, and place the anchor with stretched spring or polymer at tissue (e.g., a ligament) and release the anchor to secure an implant (e.g., 834) to the tissue.

Embodiments shown at FIGS. 111 through 116 and 115 and 116 use a pinching of tissue between 852 jaws of an anchor 850 in a manner that is similar to that of pair of forceps or tweezers, with optional one-way ratcheting or locking closing movement. An anchor 850 can include opposing jaws 852, and optional ratcheting structures (853) that allow the jaws to be closed with ratcheting but not opened. Tissue can be squeezed between two opposing faces or jaws 852 of an anchor, and pressure can be maintained on the anchor (opposing jaws 852) by any desired structural features, such as an outer ring, an integrated ratcheting feature (FIGS. 28 and 29) 854, the use of a malleable material (metal or polymer) that stays closed upon squeezing and closing the jaws together, etc. FIGS. 111-113 show a pinching concept with locking ring 854. Ring 854 can slide on to a proximal side of anchor 850 upon closing jaws 852, such as by advancement of an outer tube 851 surrounding shaft 849.

Figure 114:
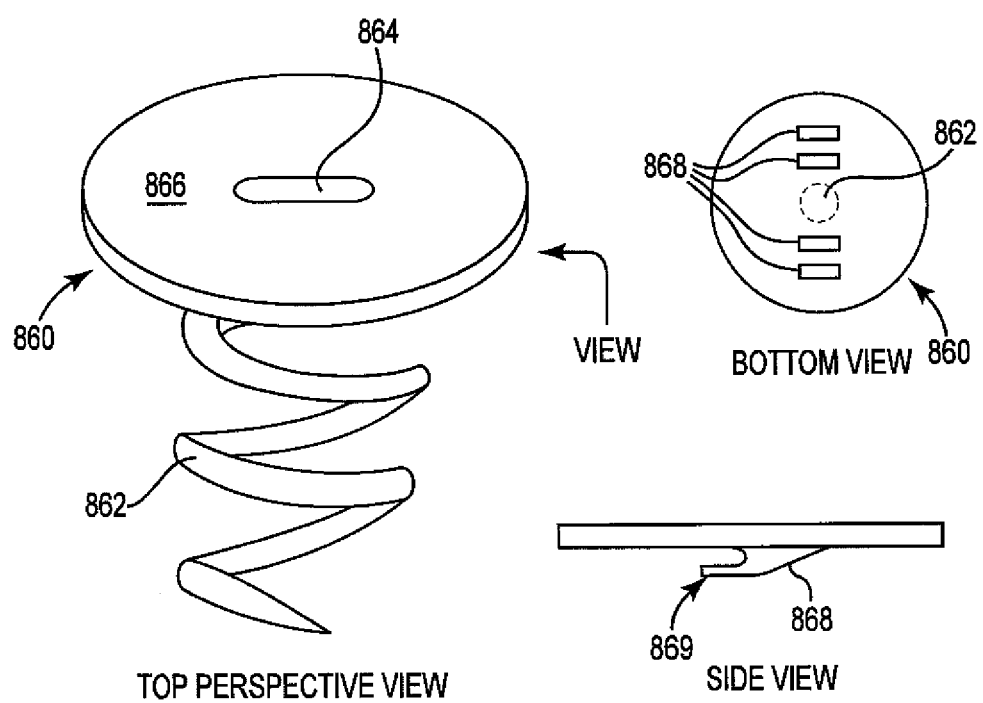
Figure 115:
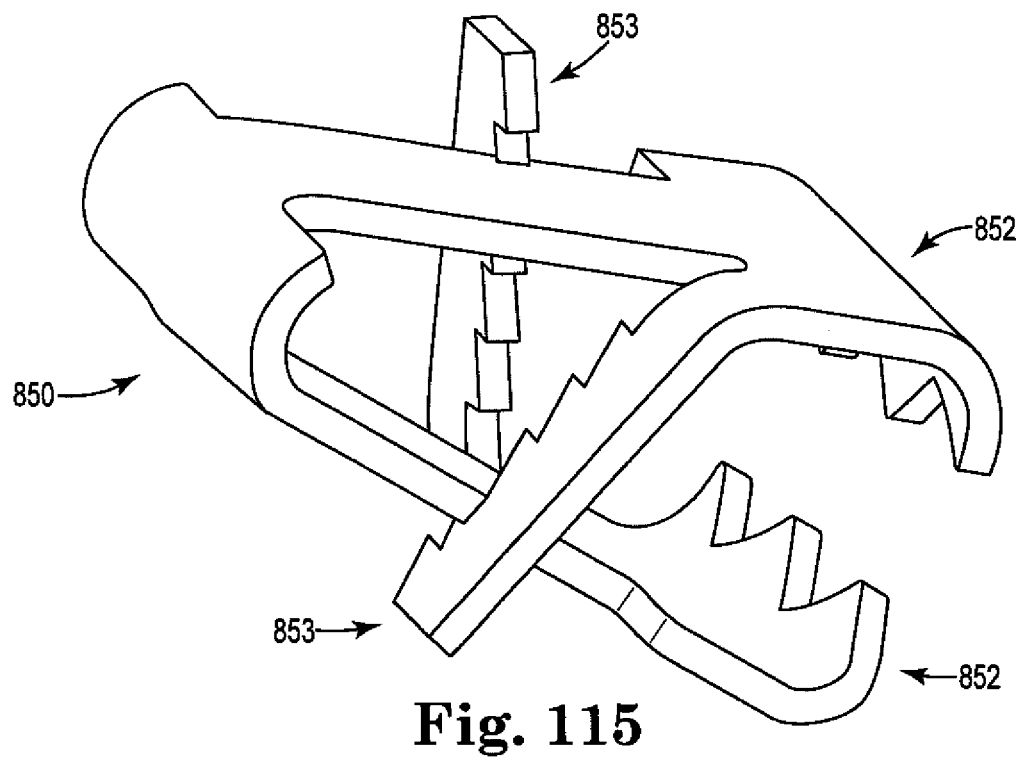
Figure 116:
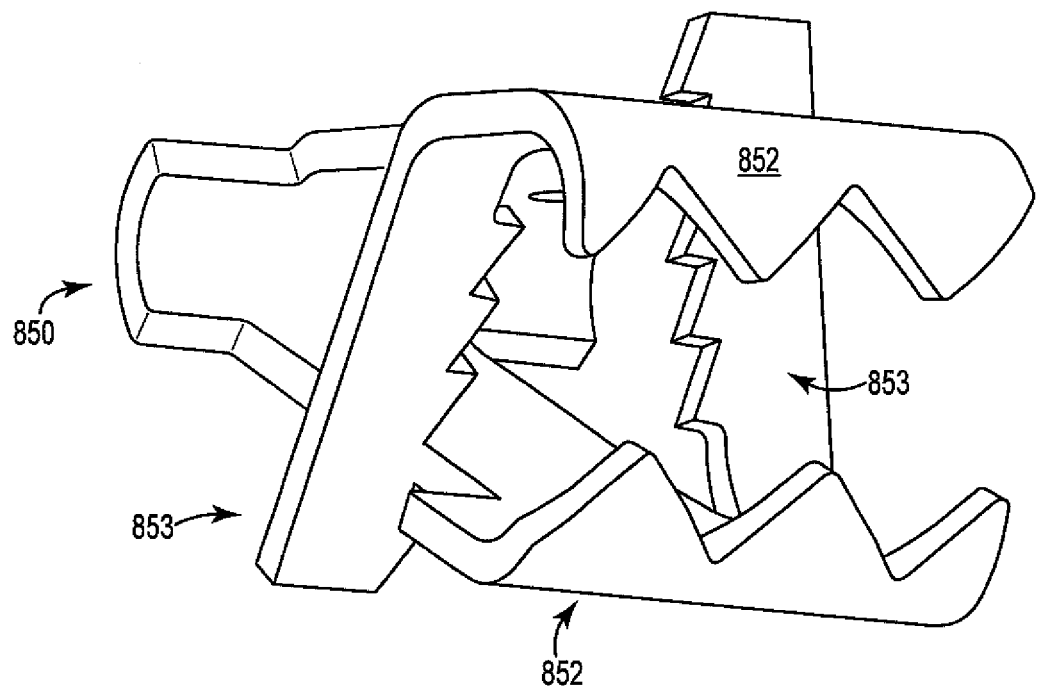

FIG. 114 shows a coil tissue fixation (anchor) incorporating a molded screw that can be inserted into tissue in one direction, and includes an anti-rotation feature to prevent reverse rotation. Previous concepts have proven to have excellent fixation strength, but the one fear is the ability to have the anchor back out of the tissue. These anti-rotation features lock on the mesh preventing the tissue anchor from working its way out of the tissue. In specific, anchor 860 includes screw head 866, slot 864 to allow rotation, helical screw 862, and anti-rotation hooks or barbs 868 on the underside of screw head 866. By rotating anchor 860 in a direction to drive screw 862 into tissue, hooks or barbs 868 are brought to contact a surface of the tissue; barbs 868 can be any counter-rotation-preventive structure located on the underside of screw head 866, to prevent counter-rotation, and may in preferred embodiments include a tapered profile with a sharp or enlarged trailing edge 869 that inhibits movement in a direction that is the reverse of the direction used to drive screw 862 into tissue.

Various devices and components of the above-described anchor embodiments can be constructed of any useful material such as stainless steel, silicone, polyurethane, polycarbonate, polypropylene, or like known or compatible materials. Further, the sizes of the components can vary greatly. For instance, the embodiments can target a 1 cm by 1 cm area with less than 1 cm in height.

Figure 117:
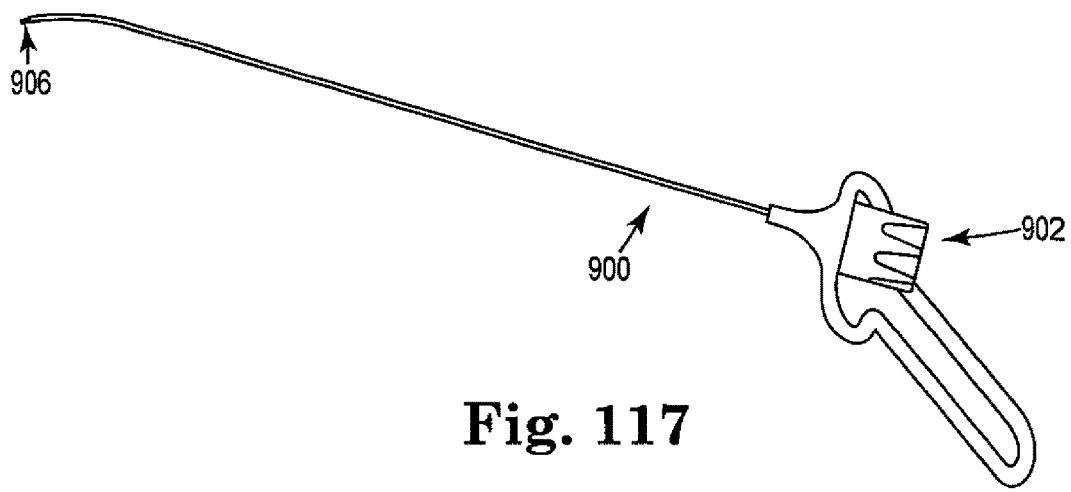
FIGS. 117-119 depict various sacral fixation drivers or systems in accordance with embodiments of described inventions.
Figure 118:
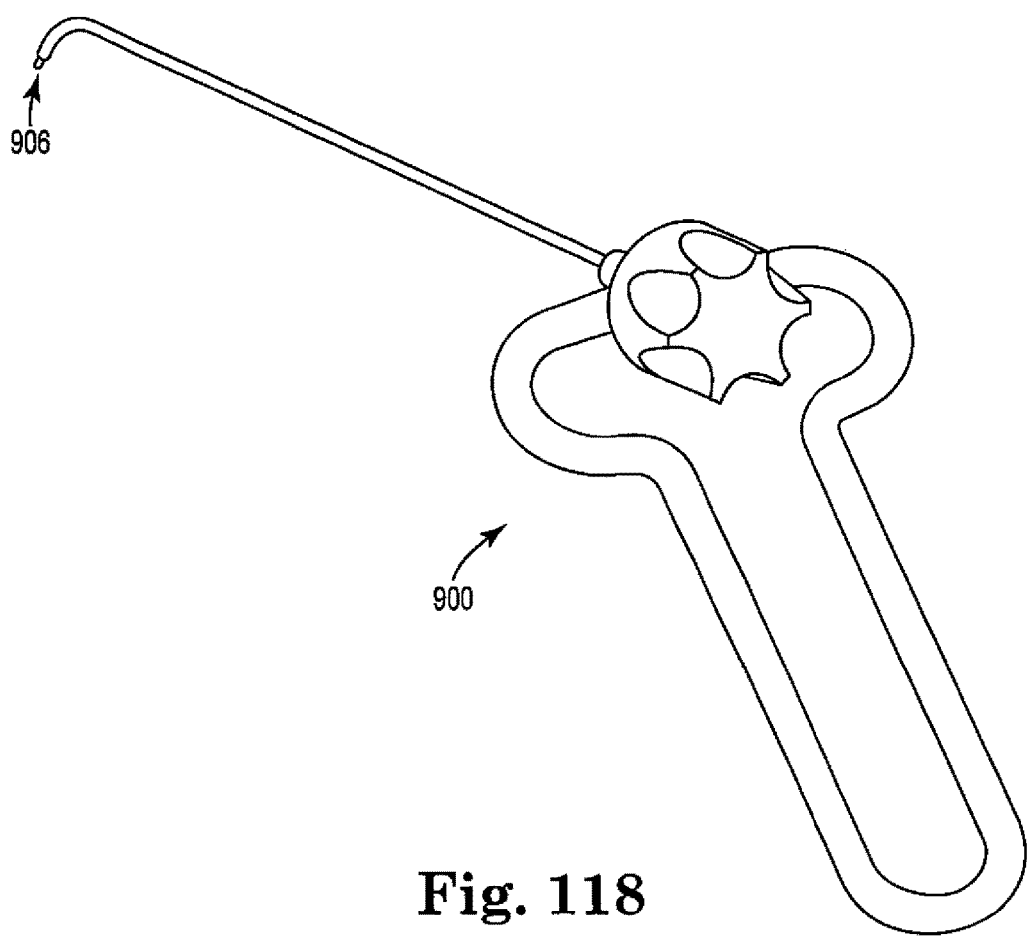
Figure 119:
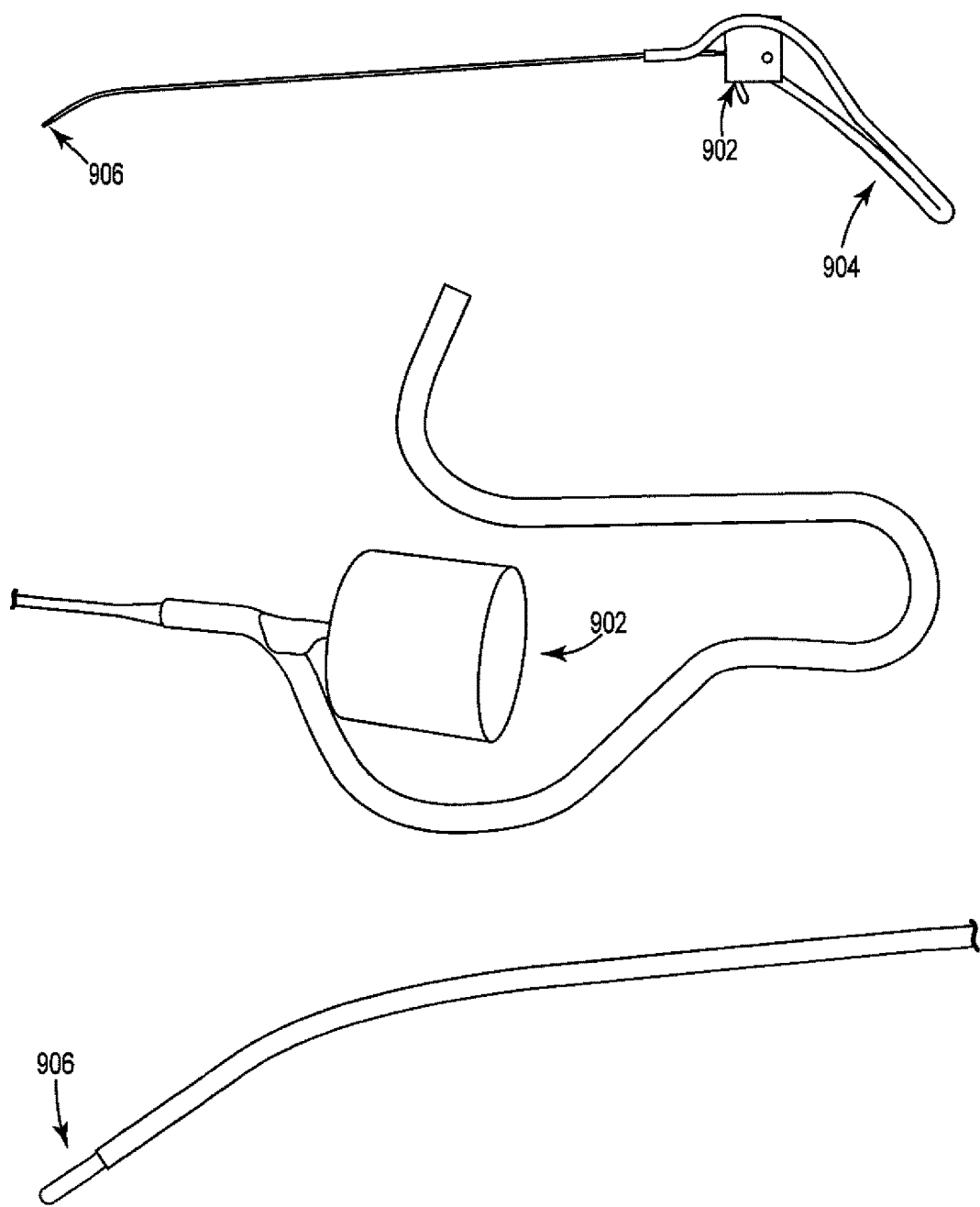
Figure 120:
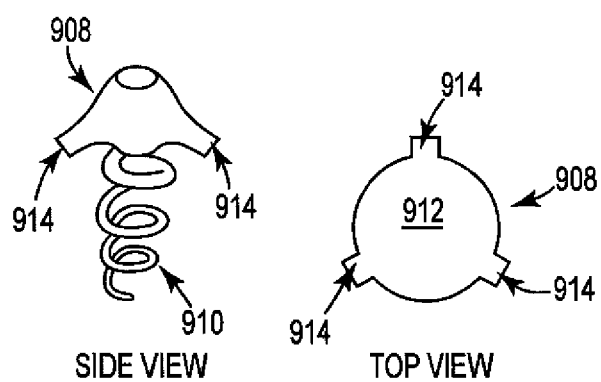
FIGS. 120-124 depict a sacral tissue fixation mesh for use in an SCP procedure in accordance with embodiments of described inventions.
Figure 121:
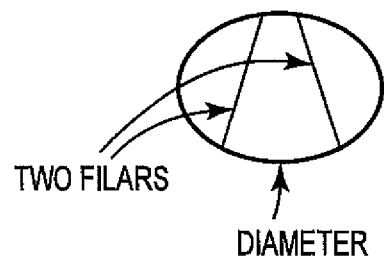
Figure 122:
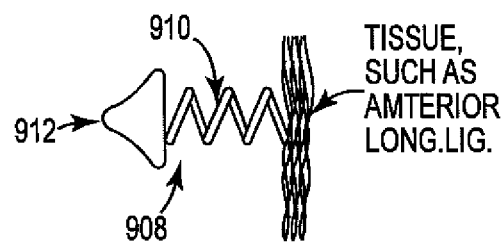
Figure 123:
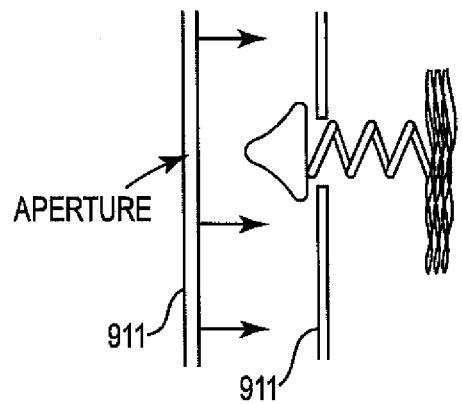
Figure 124:
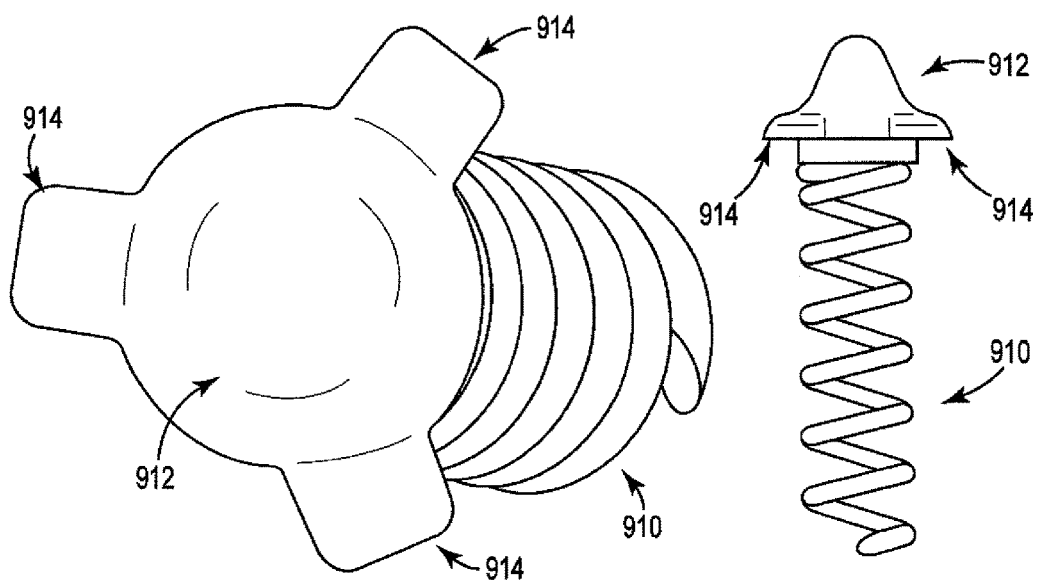

Referring generally to FIGS. 117 through 119, various embodiments of a sacral fixation element (anchor) driver or system are disclosed. A system can be a single-handed tool used to drive an anchor (e.g., a screw, helical, or coil anchor) into tissue at a region of a sacrum. The drive tool 900 or system can be reversible for left or right handed physicians. The system can include an interface that provides tactile feedback on how tight the fixation element is attached. A knob 902 and grip (handle 904) are provided such that by first loading an anchor onto tip 906, the device operation is completed. Then the device is held similar to a drill motor or other hand operated device. The thumb controls the rotation force that drives the coil to drive an anchor into tissue, e.g., transvaginally.

In alternate embodiments of a drive tool 900, a polymer outer tube, such as polycarbonate and a metal rod or other materials, can be attached to an external stand off that would allow the physician to cauterize the pre-sacral vessels if necessary (like an endoscope device with an insulated handle and a small metallic stand off for electrocautery). By combining the feature of a cauterization function with a drive function into a single device, an anchor fixation procedure can be simplify and can eliminate or consolidate steps or equipment for the physician.

The embodiments of FIGS. 120 through 124 show a sacral tissue fixation element (anchor) 908, for use in a pelvic implant procedure such as SCP procedure, prolapse, etc., in a male or female patient. Such embodiments allow for: fixation of a helical screw or coil portion 910, and cap 912 to tissue prior to attaching the implant (e.g., mesh), double checking by the operator of the fixation strength prior to attaching the implant; greater degree of coil location control in tissue (when using more than one coil) due to the number of pores in the mesh; use of a device (e.g., 900) for electrocautery because the driver is on the outside of the coil portion 910 and can make contact with coil portion 910; and prevention of coil portion 910 from backing out by locking onto the mesh due to prong feature 914 of the cap 912.

In use, anchor 908 can be used according to the following unique method of placing the anchor 908, separate from and not attached with or associated with an implant at the time of attachment. The placement, depth, and degree of strength of the secure placement can be tested and if desired the anchor 908 can be removed and replaced at a better location. After the integrity and position of anchor 908 is satisfactory, an aperture of an implant (e.g., mesh) 911 can be placed over cap 912 to secure the implant to cap 912, anchor 908, and the tissue.

Due to the configuration and functionality of cap 912, cap 912 can be made smaller or larger than coil portion 910. Regardless, the cap can secure to an implant through an aperture. In addition, the operator can see the engagement of anchor 908 with tissue, with greater ease, because the amount of material in the working area when completing the procedure is reduced by not including the implant. Various materials, such as stainless steel, polyurethane, polycarbonate, polypropylene and like materials can be employed with the system, or structures or components thereof.

Figure 125:
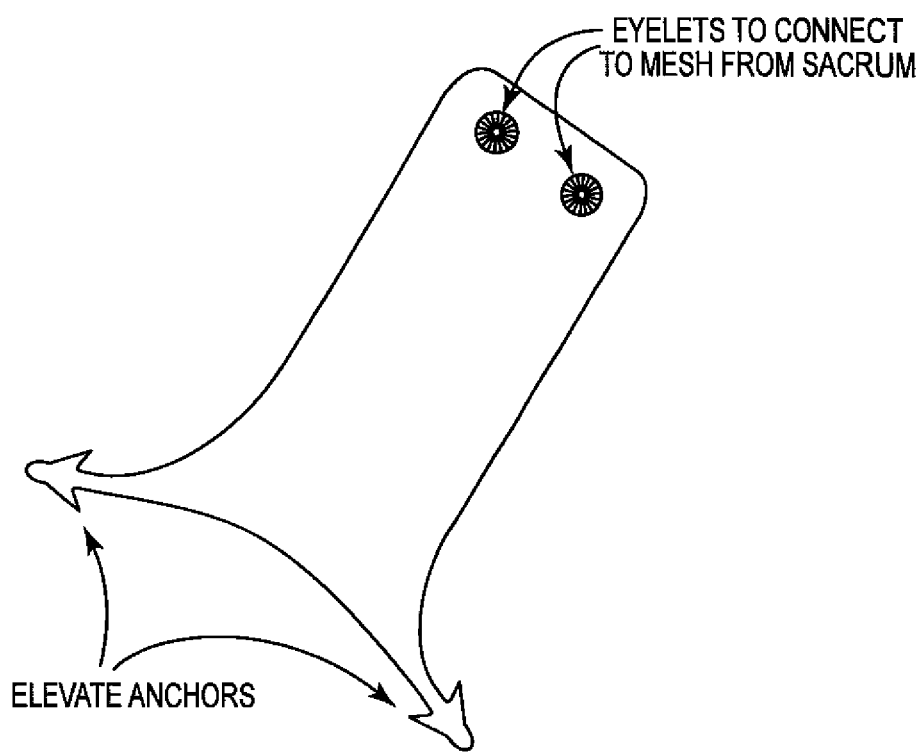
FIG. 125 depicts a SCP mesh with anchors.

An implant embodiment of FIG. 125 can include a SCP mesh with anchors or "self-fixating tips" similar to those of the Elevate® product sold by American Medical Systems of Minnetonka, Minn. In a SCP procedure, it is important for the mesh to lay flat to prevent mesh bunching and folding, a feature promoted by the present invention.

The disclosed device or system reduces the number of sutures on the vagina to ensure flatness, utilizes anterior repair anchors for a more complete/robust anterior repair, and utilizes the sacral promontory for vault suspension. The anterior repair anchoring is combined with the vault suspension technique and system to improve mesh support. The anterior repair anchors can hold the mesh flat to prevent bunching as well as provide anterior support for preventing future cystocele occurrences. Various known and compatible materials, such as polypropylene, can be used to construct all of parts of the system.

Figure 126:
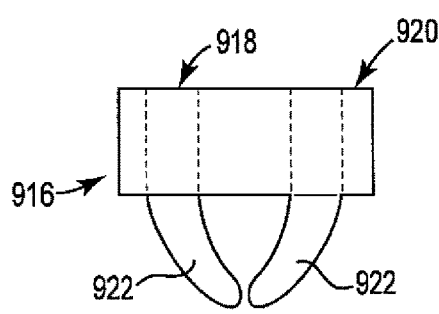
FIGS. 126-127 depict a sacral tissue fixation for mesh in a pelvic procedure (e.g., SCP) in accordance with embodiments of described inventions.
Figure 127:
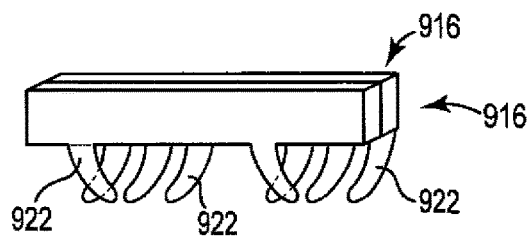
Figure 128:
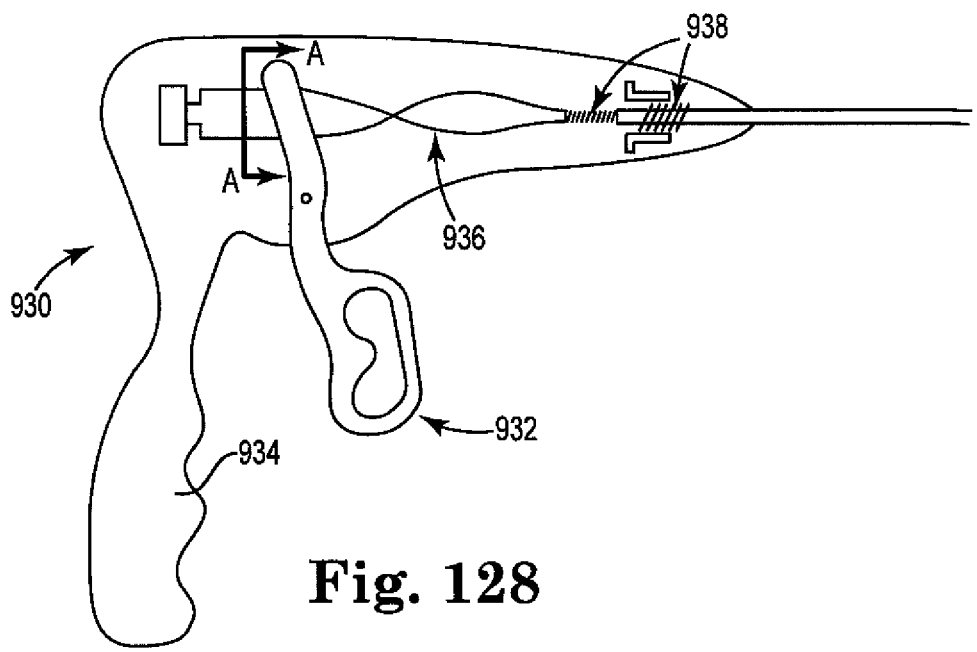
FIGS. 128-132 depict ratcheting coil drivers for use in various procedures, including a SCP procedure, in accordance with embodiments of described inventions.
Figures 129, 130:
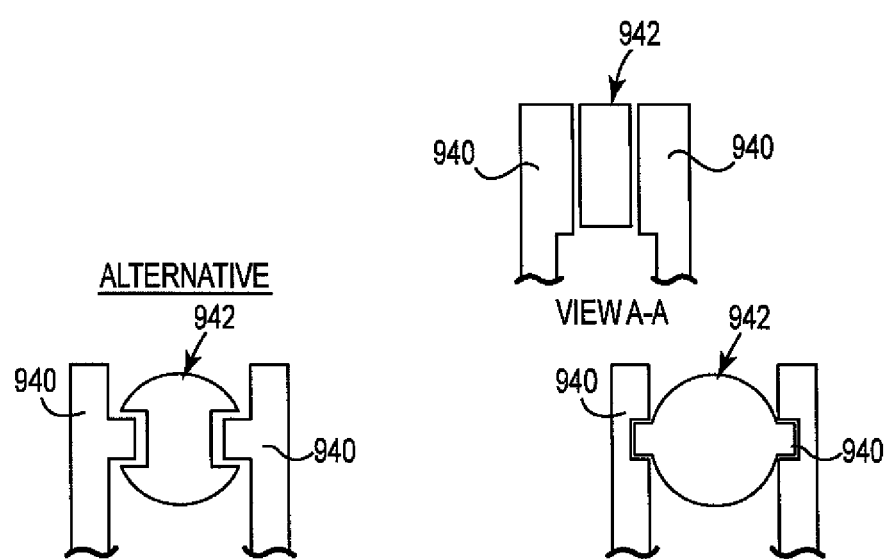

Referring to FIGS. 126 and 127, a sacral tissue fixation element (anchor) 916 for mesh is provided. The system can be used with a SCP procedure for fixation of anchor 916 and an associated implant (e.g., mesh) to an anterior longitudinal ligament. The disclosed anchor and method embodiments allow for a small amount of motion to secure an anchor to tissue, the opportunity to check the strength of the tissue hold prior to releasing the installation device, and a high strength for withstanding a high degree of normal force. With a small amount of motion with this system, an increased ability to double check the strength of the hold prior to releasing is provided, thus improving the physician's confidence in the fixation. The device or system can be constructed all, or in part, of known and compatible materials, such as stainless steel, polyurethane, polycarbonate, polypropylene and the like.

Referring to FIGS. 126 and 127, fixation to an anterior ligament can involve challenges related to: ligament thickness, fat and other tissue in the way of ligament tissue; applied force by operator; and a small working area. Anchor 916 (which can be associated or attached to an implant, not shown) includes inner tube 918, outer tube 920, and rotating graspers 922. Rotation of the inner and outer tubes brings graspers 922 together similar to an action of tweezers. Once a tube has been rotated and tissue has been captured between the graspers 922, then a rod or similar positive lock can hold the graspers together.

Figure 131:
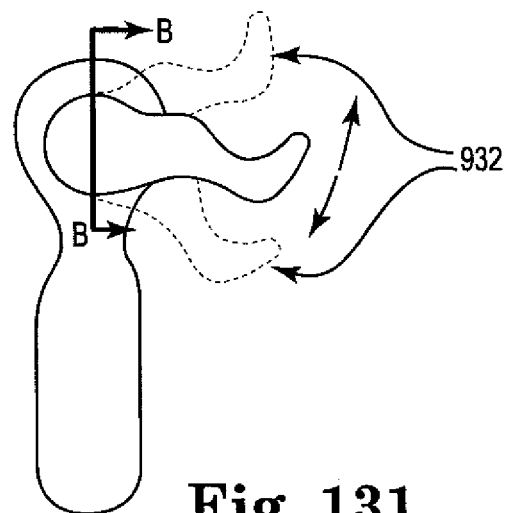
Figure 132:
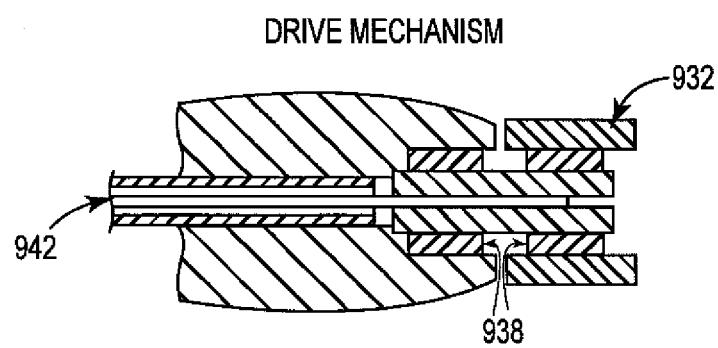

Referring to FIGS. 128 through 132, embodiments of a ratcheting anchor (screw or coil) driver for use in various procedures, including a SCP procedure, are illustrated. The driver 930 can be manually, hand-operated by movement of trigger 932 relative to handle 934. An anchor that includes an anti-reverse rotation system is provided to prevent the fixation screw/coil (anchor) from backing out during operation. Linear by movement of trigger 932 motion is transferred into a rotational device or means via a twisted bar 936 or similar construct. Two one-way coils 938 keep the motion going in one direct to properly drive the anchor and prevent reverse motion. Alternately, rotation motion can be used to drive the anchor. The rotational motion can be controlled to only drive the coil in one direction. In another alternative, a frictional trigger 940 can drive a shaft or drive rod 942 or flat bar 942. FIGS. 131 and 132 show an embodiment whereby trigger 932 moves up and down to rotate an anchor for driving the anchor into tissue (e.g., of a ligament).

An advantage of such drivers is that the ratcheting feature allows the operator to use a single hand to control the fixation device, while other conventional tools or devices rely on a two-handed operation and manual rotation of the screw (no anti-reversal feature). As such, an optimal design is provided for sacral fixation to successfully drive an anchor while preventing damage that may otherwise be caused by placing the anchor with another driver.

Figure 133:
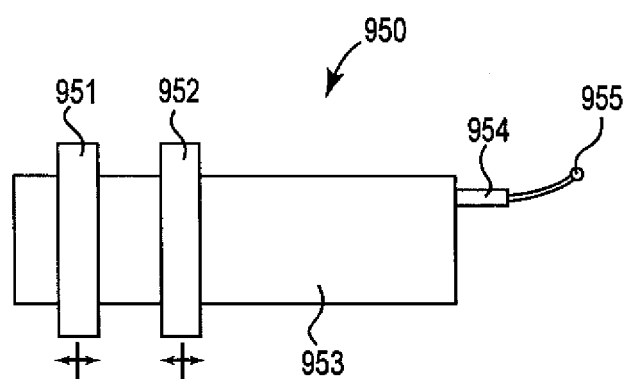
FIGS. 133-134 depict active tissue retractors for use in transvaginal SCP procedures in accordance with embodiments of described inventions.
Figure 134:
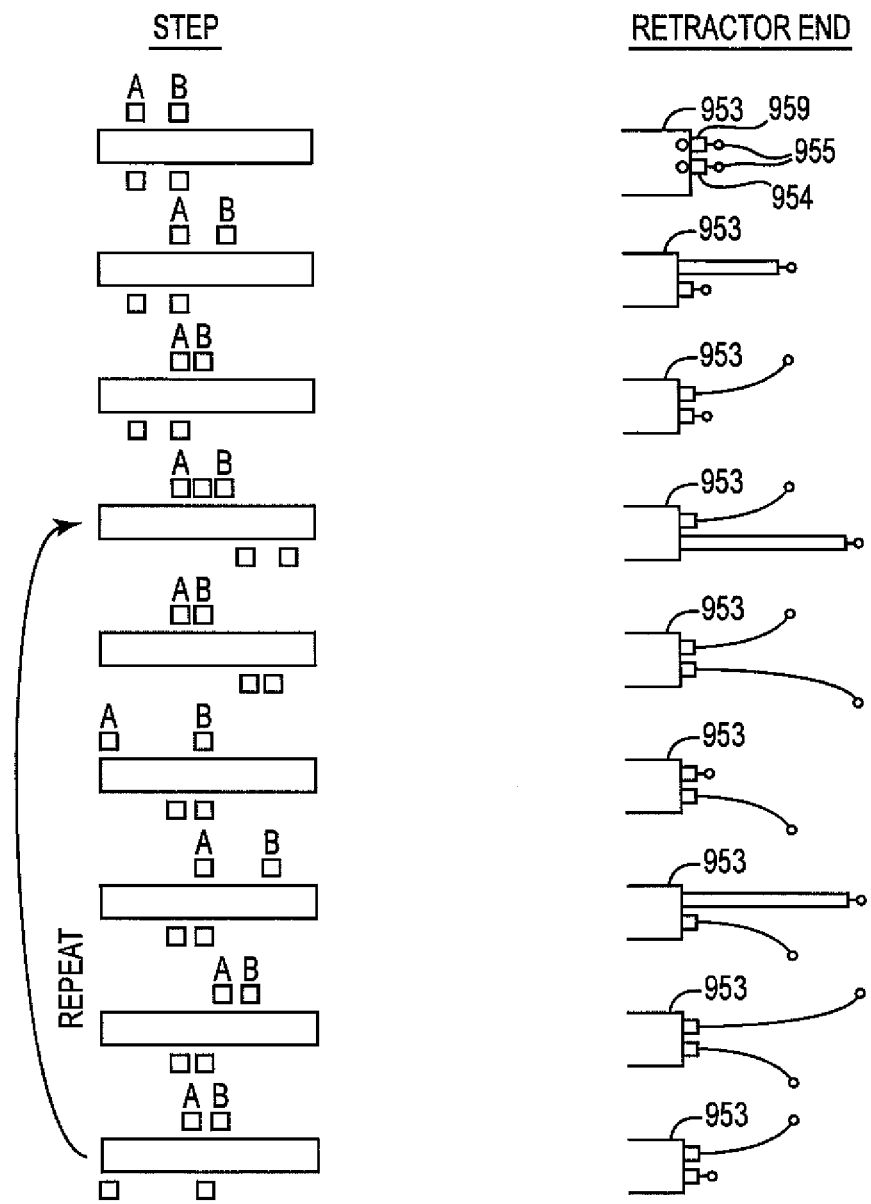

Referring to FIGS. 133 and 134, embodiments of an active tissue retractor for use in transvaginal SCP procedures is disclosed. In general, two separate hand controls are provided. With these controls, the physician can retract, advance and move tissue independent of each control and the main retractor sight tube body.

FIG. 133 shows an active retractor that allows tissue to be moved as the retractor is advanced into a surgical incision toward a surgical site. The device includes two separate controls, each of which retracts, advances, and controls the depth and rate of advancement. System 950 includes a rod handle 951 (to control a retractor rod 955 by extending or retracting the rod), tube handle 952 (to control a tube 954 by extending or retracting the tube 954), sight tube (e.g., for light, visualization, or both) 953, another tube 954 within site tube 953, and a tissue retractor rod 955 within tube 954. Desirably, system 950 includes a sufficient number of separate and separately operable tubes 954 and retractor rods 955 to provide multiple effective movement of tissue near a surgical site, to provide assess to the site for performing a surgical procedure. For example, FIG. 134 illustrates a system having two each of a combined tube 954 and retractor rod 955 structure.

With tube 953 installed transvaginally, one or more retractor rod 955 at a distal end, can be extended from a distal end of system 950 by use of rod handle 952, to a location near a near surgical site, and can be bent outward to push tissue away from a working area at the end of tube 953. Tubes 954 over the rods 955 assist to straighten the retractor rods 955 and bend them slightly inward to advance them beyond the opposite set of retractors.

Including the sight tube 953 and retractor rods into the a single device or system, while making the device or system active, will assist physicians in getting to a targeted tissue site easier and more safely. By moving tissue away from a surgical site, visibility increases, the amount of dissection is reduced, and increased visibility to decrease the potential for damaging critical nerves or vessels is provided. Various modes of operation are provided with FIG. 133. FIG. 134 depicts various steps and the corresponding retractor end positions (positions of a system of two separate tubes 954 and retractor rods 955).

Various structures, device, components or portions of the embodiments of these and other embodiments can be constructed of polypropylene, polycarbonate, stainless steel, steel, magnets, epoxy, adhesive, LED, filament bulbs, or other materials or devices known to those of ordinary skill in the art for application given the disclosure provided herein.

Various tools, systems and methods as disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2002/151762 and 2002/147382, can be employed with the present invention. Accordingly, the above-identified disclosures are fully incorporated herein by reference in their entirety.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A method of performing pelvic surgery to support a vaginal apex, the method comprising:
providing an adjustable multi-piece implant including a first piece having planar implant material including a first anterior end, a second piece including planar implant material including a second anterior end, a third piece including planar implant material including a posterior end, a first adjustment mechanism configured to connect the first piece and the third piece in a manner to allow movement between the first piece and the third piece when connected, and a second adjustment mechanism configured to connect the second piece and the third piece in a manner to allow movement between the second piece and the third piece when connected, the first adjustment mechanism including a first polymeric rod arm;
placing a tube over a mesh portion of the first piece and the first polymeric rod arm;
placing the first anterior end of the first piece, separate from the third piece, in contact with a first side of a vagina;
placing the second anterior end of the second piece, separate from the third piece, in contact with a second side of the vagina;
placing the posterior end of the third piece, separate from the first piece and the second piece, in contact with an anterior longitudinal ligament;
connecting the first piece to the third using the first adjustment mechanism; and
removing the tube from the first piece and the first polymeric rod arm;
connecting the second piece to the third piece using the second adjustment mechanism.

2. The method according to claim 1, wherein the posterior end of the third piece comprises an anchor, the method further comprises securing the anchor to the anterior longitudinal ligament.

3. The method according to claim 2, wherein the anchor is secured to the anterior longitudinal ligament by approaching the anterior longitudinal ligament at an approach angle of less than 60 degrees and pushing the anchor into the anterior longitudinal ligament.

4. The method according to claim 2, wherein the anchor is secured to the anterior longitudinal ligament by approaching the anterior longitudinal ligament at an approach angle of less than 60 degrees and pulling the anchor into the anterior longitudinal ligament.

5. The method according to claim 1, wherein the method of performing pelvic surgery to support a vaginal apex is a sacral colpopexy.

6. The method according to claim 1, wherein the first piece is mesh, and the third piece is mesh, the third piece being separate from the first piece.

7. The method according to claim 1, wherein the first anterior end of the first piece is mesh and the posterior end of the third piece is mesh, the first anterior end of the first piece being separate from the posterior end of the third piece.

8. The method according to claim 1, wherein the first adjustment mechanism also includes a first aperture disposed on the first piece, the second adjustment mechanism comprising a second polymeric rod arm, and a second aperture disposed on the second piece, the method further comprising:
moving the first polymeric rod arm through the first aperture; and
moving the second polymeric rod arm through the second aperture.

9. The method according to claim 1, wherein the second adjustment mechanism is selected from at least one of a suture, a one-way or two-way adjustable grommet, a one-way barb, a spring-biased rod, or a tube structure.

10. The method according to claim 1, wherein the first anterior end of the first piece is connected to vaginal tissue in a region of the vaginal apex with at least one of a suture, an anchor, a clamp, a staple, or a biological adhesive.

11. The method according to claim 1, wherein the posterior end of the third piece is connected to the anterior longitudinal ligament with at least one of a suture, an anchor, a clamp, a staple, or a biological adhesive.

12. The method according to claim 1, wherein the first adjustment mechanism also includes a first aperture, the second adjustment mechanism comprising a second polymeric rod arm and a second aperture, the first and second polymeric rod arms are located on the third piece, and the first and second apertures are located on the first and second pieces, respectively, and
wherein adjusting a length of the implant comprises moving the first and second polymeric rod arms through the first and second apertures, respectively.

13. The method according to claim 1, wherein the planar implant material is at least one of an elastic mesh, a strip, or a tape.

* * * * *